(12) United States Patent
Jeong et al.

(10) Patent No.: US 11,634,430 B2
(45) Date of Patent: Apr. 25, 2023

(54) HETEROCYCLIC COMPOUND AND ORGANIC LIGHT EMITTING ELEMENT COMPRISING SAME

(71) Applicant: LG CHEM, LTD., Seoul (KR)

(72) Inventors: Kyung Seok Jeong, Daejeon (KR); Minseung Chun, Daejeon (KR); Wanpyo Hong, Daejeon (KR); Jin Joo Kim, Daejeon (KR); Hongsik Yoon, Daejeon (KR); Joongsuk Oh, Daejeon (KR)

(73) Assignee: LG CHEM, LTD., Seoul (KR)

( * ) Notice: Subject to any disclaimer, the term of this patent is extended or adjusted under 35 U.S.C. 154(b) by 889 days.

(21) Appl. No.: 16/475,221

(22) PCT Filed: Apr. 27, 2018

(86) PCT No.: PCT/KR2018/004956
§ 371 (c)(1),
(2) Date: Jul. 1, 2019

(87) PCT Pub. No.: WO2018/199699
PCT Pub. Date: Nov. 1, 2018

(65) Prior Publication Data
US 2019/0359633 A1    Nov. 28, 2019

(30) Foreign Application Priority Data

Apr. 27, 2017    (KR) .................. 10-2017-0054504

(51) Int. Cl.
| | | |
|---|---|---|
| *H01L 51/54* | (2006.01) | |
| *C07D 498/04* | (2006.01) | |
| *H01L 51/00* | (2006.01) | |
| *H01L 51/50* | (2006.01) | |

(52) U.S. Cl.
CPC ........ *C07D 498/04* (2013.01); *H01L 51/0061* (2013.01); *H01L 51/0069* (2013.01); *H01L 51/0071* (2013.01); *H01L 51/0072* (2013.01); *H01L 51/0094* (2013.01); *H01L 51/5056* (2013.01); *H01L 51/0073* (2013.01); *H01L 51/5012* (2013.01)

(58) Field of Classification Search
None
See application file for complete search history.

(56) References Cited

U.S. PATENT DOCUMENTS

| | | |
|---|---|---|
| 2014/0175395 A1 | 6/2014 | Kim et al. |
| 2016/0028014 A1 | 1/2016 | Kim et al. |
| 2016/0351816 A1 | 12/2016 | Kim et al. |
| 2016/0351818 A1 | 12/2016 | Kim et al. |
| 2017/0062729 A1 | 3/2017 | Cha et al. |
| 2017/0342318 A1 | 11/2017 | Kim et al. |

FOREIGN PATENT DOCUMENTS

| | | |
|---|---|---|
| EP | 3266848 A1 | 1/2018 |
| JP | 10-95972 A | 4/1998 |
| KR | 20000051826 A | 8/2000 |
| KR | 10-2014-0080205 A | 6/2014 |
| KR | 10-2015-0130206 A | 11/2015 |
| KR | 10-2016-012066 A | 2/2016 |
| KR | 10-2016-0040198 A | 4/2016 |
| KR | 10-2016-0081531 A | 7/2016 |
| KR | 10-2016-0095827 A | 8/2016 |
| KR | 10-2016-0141359 A | 12/2016 |
| KR | 10-2016-0141360 A | 12/2016 |

*Primary Examiner* — Andrew K Bohaty
(74) *Attorney, Agent, or Firm* — Dentons US LLP

(57) ABSTRACT

The present specification provides a heterocyclic compound of Chemical Formula 1, and an organic light emitting device comprising the same. The heterocyclic compound used as a material of an organic material layer of an organic light emitting device provides enhanced efficiency, low driving voltage, and enhanced lifetime properties of the organic light emitting device.

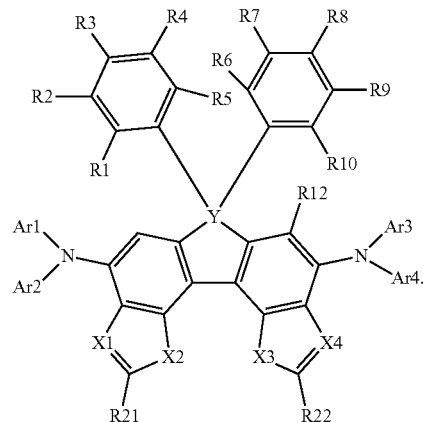

17 Claims, 1 Drawing Sheet

【FIG. 1】
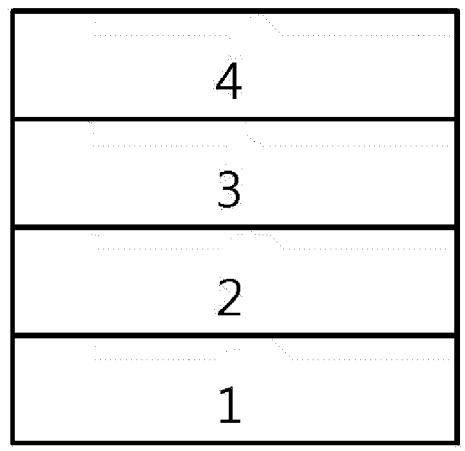
【FIG. 2】
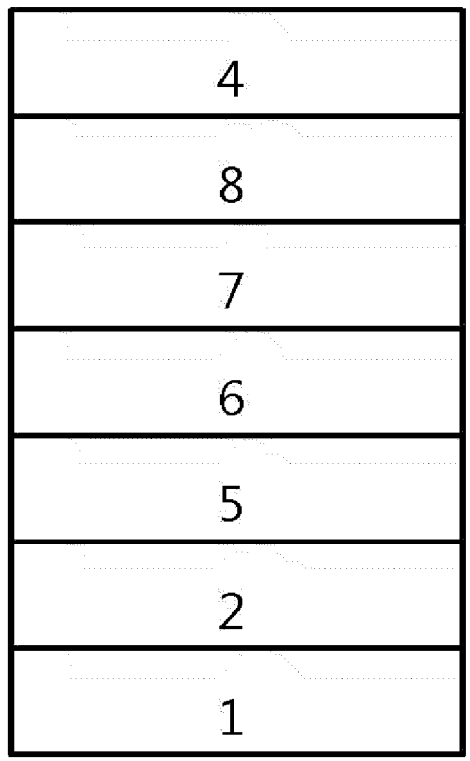

HETEROCYCLIC COMPOUND AND ORGANIC LIGHT EMITTING ELEMENT COMPRISING SAME

TECHNICAL FIELD

The present application is a National Phase entry pursuant to 35 U.S.C. § 371 of PCT/KR2018/004956, filed on Apr. 27, 2018, and claims priority to and the benefit of Korean Patent Application No. 10-2017-0054504, filed on Apr. 27, 2017, the disclosures of which are incorporated herein by reference in their entirety.

The present specification relates to a heterocyclic compound and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification describes a heterocyclic compound and an organic light emitting device including the same.

Technical Solution

One embodiment of the present specification provides a heterocyclic compound represented by the following Chemical Formula 1.

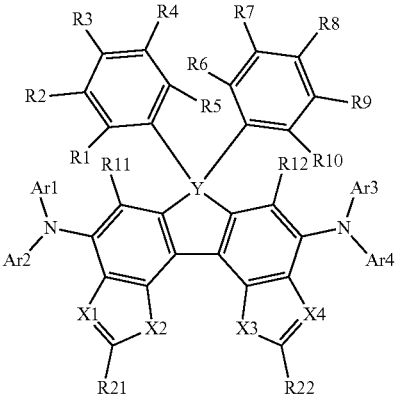

[Chemical Formula 1]

In Chemical Formula 1,

Y is C or Si,

R11 and R12 are the same as or different from each other, and each independently hydrogen; deuterium; a cyano group; a halogen group; a silyl group; a boron group; a substituted or unsubstituted alkyl group; a substituted or unsubstituted alkoxy group; a substituted or unsubstituted cycloalkyl group; a substituted or unsubstituted aryl group; a substituted or unsubstituted alkylamine group; a substituted or unsubstituted arylamine group; a substituted or unsubstituted heteroarylamine group; or a substituted or unsubstituted heterocyclic group, X1 and X4 are the same as or different from each other, and each independently CR, P or N, X2 and X3 are the same as or different from each other, and each independently CR'R", O, S, PRa, PORb or NRc, and R, R', R", Ra, Rb, Rc, R21, R22, Ar1 to Ar4 and R1 to R10 are the same as or different from each other, and each independently hydrogen; deuterium; a cyano group; a halogen group; a silyl group; a boron group; a substituted or unsubstituted alkyl group; a substituted or unsubstituted alkoxy group; a substituted or unsubstituted cycloalkyl group; a substituted or unsubstituted aryl group; a substituted or unsubstituted alkylamine group; a substituted or unsubstituted arylamine group; a substituted or unsubstituted heteroarylamine group; or a substituted or unsubstituted heterocyclic group, or adjacent substituents bond to each other to form a substituted or unsubstituted ring.

Another embodiment of the present specification provides an organic light emitting device including a first electrode; a second electrode provided to face the first electrode; and one or more organic material layers provided between the first electrode and the second electrode, wherein one or more layers of the one or more organic material layers include the heterocyclic compound represented by Chemical Formula 1.

Advantageous Effects

A heterocyclic compound described in the present specification can be used as a material of an organic material layer of an organic light emitting device. A heterocyclic compound according to at least one embodiment is capable of enhancing efficiency, obtaining a low driving voltage and/or enhancing lifetime properties in an organic light emitting device. Particularly, a compound described in the present specification can be used as a material of hole injection, hole transfer, hole injection and hole transfer, electron blocking, light emitting, hole blocking, electron transfer or electron injection.

DESCRIPTION OF DRAWINGS

FIG. 1 is a diagram illustrating an organic light emitting device formed with a substrate (1), an anode (2), a light emitting layer (3) and a cathode (4).

FIG. 2 is a diagram illustrating an organic light emitting device formed with a substrate (1), an anode (2), a hole injection layer (5), a hole transfer layer (6), a light emitting layer (7), an electron transfer layer (8) and a cathode (4).

1: Substrate
2: Anode
3: Light Emitting Layer
4: Cathode
5: Hole Injection Layer
6: Hole Transfer Layer
7: Light Emitting Layer
8: Electron Transfer Layer

MODE FOR DISCLOSURE

Hereinafter, the present specification will be described in detail.

The present specification provides a heterocyclic compound represented by Chemical Formula 1. When using the heterocyclic compound represented by Chemical Formula 1 in an organic material layer of an organic light emitting device, efficiency of the organic light emitting device is enhanced, and a low driving voltage and excellent lifetime properties are obtained as well.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of the substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

Examples of the substituents are described below, however, the substituents are not limited thereto.

The term "substituted or unsubstituted" in the present specification means being substituted with one, two or more substituents selected from the group consisting of deuterium; a halogen group; a cyano group; a silyl group; a boron group; a substituted or unsubstituted alkyl group; a substituted or unsubstituted cycloalkyl group; a substituted or unsubstituted alkoxy group; a substituted or unsubstituted alkylamine group; a substituted or unsubstituted heteroarylamine group; a substituted or unsubstituted arylamine group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present specification, examples of the halogen group may include fluorine (F), chlorine (Cl), bromine (Br) or iodine (I).

In the present specification, the silyl group may be represented by a chemical formula of $-SiR_aR_bR_c$, and $R_a$, $R_b$ and $R_c$ may each be hydrogen; a substituted or unsubstituted alkyl group; or a substituted or unsubstituted aryl group. Specific examples of the silyl group may include a trimethylsilyl group; a triethylsilyl group; a t-butyldimethylsilyl group; a vinyldimethylsilyl group; a propyldimethylsilyl group; a triphenylsilyl group; a diphenylsilyl group; a phenylsilyl group and the like, but are not limited thereto.

In the present specification, the boron group may be represented by a chemical formula of $-BR_aR_b$, and $R_a$ and $R_b$ may each be hydrogen; a substituted or unsubstituted alkyl group; or a substituted or unsubstituted aryl group. Specific examples of the boron group may include a trimethylboron group, a triethylboron group, a t-butyldimethylboron group, a triphenylboron group, a phenylboron group and the like, but are not limited thereto.

In the present specification, the alkyl group may be linear or branched, and although not particularly limited thereto, the number of carbon atoms is preferably from 1 to 40. According to one embodiment, the number of carbon atoms of the alkyl group is from 1 to 20. According to another embodiment, the number of carbon atoms of the alkyl group is from 1 to 10. According to another embodiment, the number of carbon atoms of the alkyl group is from 1 to 6. Specific examples of the alkyl group may include a methyl group, an ethyl group, a propyl group, an n-propyl group, an isopropyl group, a butyl group, an n-butyl group, an isobutyl group, a tert-butyl group, a sec-butyl group, a 1-methylbutyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 4-methylhexyl group, a 5-methylhexyl group and the like, but are not limited thereto.

In the present specification, the alkoxy group may be linear, branched or cyclic. The number of carbon atoms of the alkoxy group is not particularly limited, but is preferably from 1 to 40. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy and the like, but are not limited thereto.

The alkyl group, the alkoxy group and other substituents including an alkyl group part described in the present specification include both linear and branched forms.

In the present specification, the cycloalkyl group is not particularly limited, but preferably has 3 to 60 carbon atoms, and according to one embodiment, the number of carbon atoms of the cycloalkyl group is from 3 to 40. According to another embodiment, the number of carbon atoms of the cycloalkyl group is from 3 to 20. According to another embodiment, the number of carbon atoms of the cycloalkyl group is from 3 to 6. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkylamine group preferably has, although not particularly limited thereto, 1 to 40 carbon atoms. Specific examples of the alkylamine group may include a methylamine group, a dimethylamine group, an ethylamine group, a diethylamine group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include monocyclic aryl groups, polycyclic aryl groups, or both monocyclic aryl groups and polycyclic aryl groups.

Specific examples of the arylamine group may include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group and the like, but are not limited thereto.

In the present specification, examples of the heteroarylamine group may include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a polycyclic heterocyclic group. The heteroarylamine group including two or more heterocyclic groups may include monocyclic heterocyclic groups, polycyclic heterocyclic groups, or both monocyclic heterocyclic groups and polycyclic heterocyclic groups.

In the present specification, the aryl group is not particularly limited, but preferably has 6 to 60 carbon atoms, and may be a monocyclic aryl group or a polycyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof may include a phenyl group, a biphenyl group, a terphenyl group and the like, but are not limited thereto. Examples of the polycyclic aryl group may include a naphthyl group, an anthracenyl group, a phenanthrenyl group, a pyrenyl group, a perylenyl group, a triphenyl group, a chrysenyl group, a fluorenyl group and the like, but are not limited thereto.

In the present specification, the fluorenyl group may be substituted, and two substituents may bond to each other to form a spiro structure.

When the fluorenyl group is substituted, spirofluorenyl groups such as

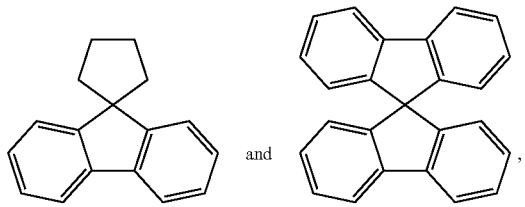

and substituted fluorenyl groups such as

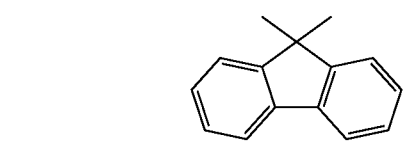

(9,9-dimethylfluorenyl group) and

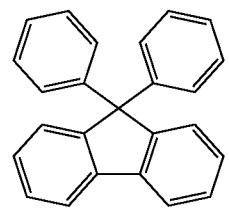 [SMILES: c1ccc(C2(c3ccccc3)c3ccccc3-c3ccccc32)cc1]

(9,9-diphenylfluorenyl group) may be included. However, the structure is not limited thereto.

In the present specification, the heterocyclic group is a heterocyclic group including one or more of N, O, P, S, Si and Se as a heteroatom, and although not particularly limited thereto, the number of carbon atoms is preferably from 2 to 60. According to one embodiment, the number of carbon atoms of the heterocyclic group is from 2 to 30. Examples of the heterocyclic group may include a pyridyl group, a pyrrole group, a pyrimidyl group, a pyridazinyl group, a furanyl group, a thiophenyl group, an imidazole group, a pyrazole group, an oxazole group, an isoxazole group, a thiazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a thiazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzothiazole group, a benzoxazole group, a benzimidazole group, a benzothiophene group, a benzofuranyl group, a dibenzothiophenyl group, a dibenzofuranyl group, a carbazole group, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzimidazoquinazoline group, a benzimidazophenanthridine group or the like, but are not limited thereto.

In the present specification, descriptions on the heterocyclic group provided above may be applied to the heteroaryl group except for being aromatic.

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the "ring" in the substituted or unsubstituted ring formed by adjacent groups bonding to each other means a substituted or unsubstituted hydrocarbon ring; or a substituted or unsubstituted heteroring.

In the present specification, the hydrocarbon ring may be aromatic, aliphatic or a fused ring of aromatic and aliphatic, and may be selected from among the examples of the cycloalkyl group or the aryl group except for those that are not monovalent.

In the present specification, descriptions on the aryl group may be applied to the aromatic hydrocarbon ring except for being monovalent.

In the present specification, the heteroring includes one or more atoms that are not carbon, that is, heteroatoms, and specifically, the heteroatom may include one or more atoms selected from the group consisting of O, N, Se, S, Si and the like. The heteroring may be monocyclic or polycyclic, aromatic, aliphatic or a fused ring of aromatic and aliphatic, and may be selected from among the examples of the heteroaryl group except for those that are not monovalent.

In one embodiment of the present specification, R1 to R10 are the same as or different from each other, and each independently hydrogen; deuterium; a substituted or unsubstituted alkyl group; or a substituted or unsubstituted aryl group, or adjacent substituents bond to each other to form a substituted or unsubstituted ring.

In another embodiment, R1 to R10 are the same as or different from each other, and each independently hydrogen; deuterium; a substituted or unsubstituted alkyl group having 1 to 20 carbon atoms; or a substituted or unsubstituted aryl group having 6 to 20 carbon atoms, or adjacent substituents bond to each other to form a substituted or unsubstituted ring.

In another embodiment, R1 to R10 are the same as or different from each other, and each independently hydrogen; deuterium; a substituted or unsubstituted methyl group; a substituted or unsubstituted ethyl group; a substituted or unsubstituted propyl group; a substituted or unsubstituted phenyl group; or a substituted or unsubstituted naphthyl group, or adjacent substituents bond to each other to form a substituted or unsubstituted ring.

In another embodiment, R1 to R10 are the same as or different from each other, and each independently hydrogen; deuterium; a methyl group; an ethyl group; a propyl group; a phenyl group; or a naphthyl group, or adjacent substituents bond to each other to form a substituted or unsubstituted ring.

In another embodiment, R1 to R10 are the same as or different from each other, and each independently hydrogen; deuterium; a methyl group; an ethyl group; a propyl group; a phenyl group; or a naphthyl group, or R5 and R6 bond to each other to form a substituted or unsubstituted ring.

According to another embodiment, R1 to R4 and R7 to R10 are hydrogen, and R5 and R6 bond to each other to form a pentagonal ring.

In another embodiment, R5 and R6 bond to each other to form a substituted or unsubstituted ring.

According to another embodiment, R5 and R6 bond to each other to form a pentagonal ring.

In one embodiment of the present specification, Chemical Formula 1 may be represented by the following Chemical Formula 2 or Chemical Formula 3.

[Chemical Formula 2]

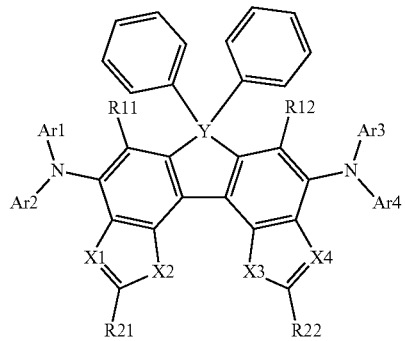

[Chemical Formula 3]

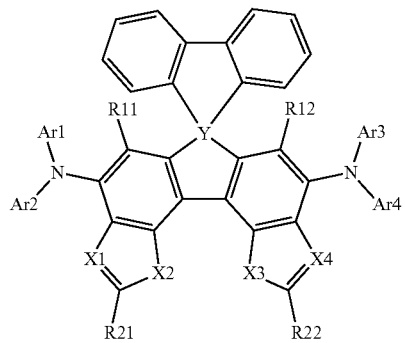

In Chemical Formulae 2 and 3

Ar1 to Ar4, R11, R12, X1 to X4, Y, R21 and R22 have the same definitions as in Chemical Formula 1.

According to one embodiment of the present specification, Ar1 to Ar4 are the same as or different from each other, and each independently hydrogen; deuterium; a substituted or unsubstituted aryl group; or a substituted or unsubstituted heteroaryl group.

According to one embodiment of the present specification, Ar1 to Ar4 are the same as or different from each other, and each independently a substituted or unsubstituted aryl group; or a substituted or unsubstituted heteroaryl group.

In another embodiment, Ar1 to Ar4 are the same as or different from each other, and each independently a substituted or unsubstituted aryl group having 6 to 30 carbon atoms; or a substituted or unsubstituted heteroaryl group having 2 to 30 carbon atoms.

According to another embodiment, Ar1 to Ar4 are the same as or different from each other, and each independently a substituted or unsubstituted aryl group having 6 to 30 carbon atoms; or a substituted or unsubstituted heteroaryl group having 2 to 30 carbon atoms including one or more of O, S and N as a heteroelement.

According to another embodiment, Ar1 to Ar4 are the same as or different from each other, and each independently a substituted or unsubstituted phenyl group; a substituted or unsubstituted biphenyl group; a substituted or unsubstituted naphthyl group; a substituted or unsubstituted phenanthrenyl group; or a substituted or unsubstituted dibenzofuranyl group.

In another embodiment, Ar1 to Ar4 are the same as or different from each other, and each independently a phenyl group unsubstituted or substituted with a halogen group, a cyano group, a silyl group or an alkyl group; a biphenyl group unsubstituted or substituted with a halogen group, a cyano group, a silyl group or an alkyl group; a naphthyl group unsubstituted or substituted with a halogen group, a cyano group, a silyl group or an alkyl group; a phenanthrenyl group unsubstituted or substituted with a halogen group, a cyano group, a silyl group or an alkyl group; or a dibenzofuranyl group unsubstituted or substituted with a halogen group, a cyano group, a silyl group or an alkyl group.

According to another embodiment, Ar1 to Ar4 are the same as or different from each other, and each independently a phenyl group unsubstituted or substituted with fluorine (F), a cyano group, a trimethylsilyl group, a methyl group or a butyl group; a biphenyl group unsubstituted or substituted with fluorine (F), a cyano group, a trimethylsilyl group, a methyl group or a butyl group; a naphthyl group unsubstituted or substituted with fluorine (F), a cyano group, a trimethylsilyl group, a methyl group or a butyl group; a phenanthrenyl group unsubstituted or substituted with fluorine (F), a cyano group, a trimethylsilyl group, a methyl group or a butyl group; or a dibenzofuranyl group unsubstituted or substituted with fluorine (F), a cyano group, a trimethylsilyl group, a methyl group or a butyl group.

In one embodiment of the present specification, R11 and R12 are the same as or different from each other, and each independently hydrogen; deuterium; or a substituted or unsubstituted alkyl group.

In another embodiment, R11 and R12 are the same as or different from each other, and each independently hydrogen; deuterium; or a substituted or unsubstituted alkyl group having 1 to 20 carbon atoms.

In another embodiment, R11 and R12 are the same as or different from each other, and each independently hydrogen; deuterium; a substituted or unsubstituted methyl group; a substituted or unsubstituted ethyl group; or a substituted or unsubstituted butyl group.

According to another embodiment, R11 and R12 are the same as or different from each other, and each independently hydrogen; deuterium; a methyl group; an ethyl group; or a t-butyl group.

According to another embodiment, R11 and R12 are hydrogen.

In one embodiment of the present specification, X1 and X4 are the same as or different from each other, and each independently CR, P or N.

In one embodiment of the present specification, X2 and X3 are the same as or different from each other, and each independently CR'R", O, S, PRa, PORb or NRc.

In one embodiment of the present specification, R, R', R", Ra, Rb and Rc are the same as or different from each other, and each independently hydrogen; deuterium; a substituted or unsubstituted alkyl group; or a substituted or unsubstituted aryl group.

In another embodiment, R, R', R", Ra, Rb and Rc are the same as or different from each other, and each independently hydrogen; deuterium; a substituted or unsubstituted alkyl group having 1 to 20 carbon atoms; or a substituted or unsubstituted aryl group having 6 to 30 carbon atoms.

According to another embodiment, R, R', R", Ra, Rb and Rc are the same as or different from each other, and each independently hydrogen; deuterium; a substituted or unsubstituted methyl group; a substituted or unsubstituted ethyl group; a substituted or unsubstituted butyl group; a substituted or unsubstituted phenyl group; a substituted or unsubstituted biphenyl group; or a substituted or unsubstituted naphthyl group.

According to another embodiment, R, R', R", Ra, Rb and Rc are the same as or different from each other, and each independently hydrogen; deuterium; a methyl group; an ethyl group; a butyl group; a phenyl group; a biphenyl group; or a naphthyl group.

In one embodiment of the present specification, X1 and X4 are the same as or different from each other, and each independently CR or N.

According to another embodiment, X1 and X4 are N.

In one embodiment of the present specification, X2 and X3 are the same as or different from each other, and each independently O or S.

According to another embodiment, X2 and X3 are O.

In another embodiment, X1 and X4 are N, and X2 and X3 are O.

In one embodiment of the present specification, Chemical Formula 1 may be represented by the following Chemical Formula 4 or Chemical Formula 5.

[Chemical Formula 4]

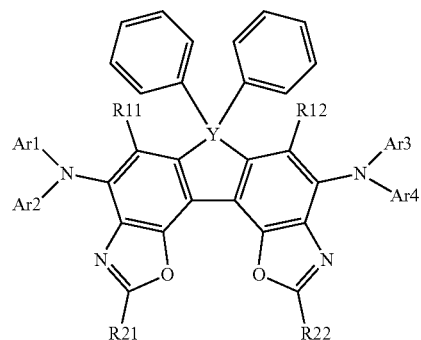

[Chemical Formula 5]

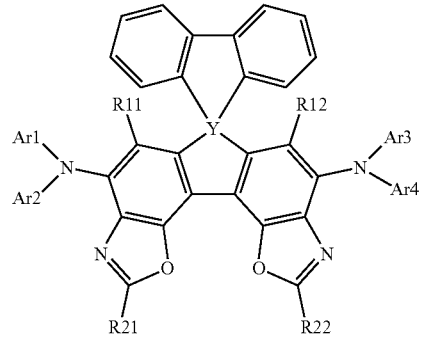

In Chemical Formulae 4 and 5,

Ar1 to Ar4, R11, R12, Y, R21 and R22 have the same definitions as in Chemical Formula 1.

In one embodiment of the present specification, Chemical Formula 1 may be represented by the following Chemical Formula 6 or Chemical Formula 7.

[Chemical Formula 6]

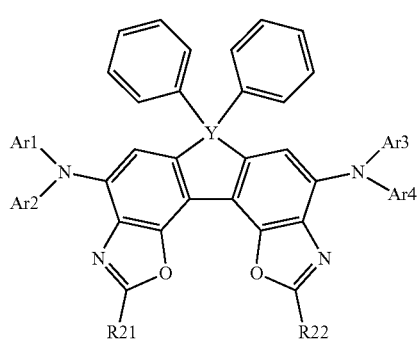

[Chemical Formula 7]

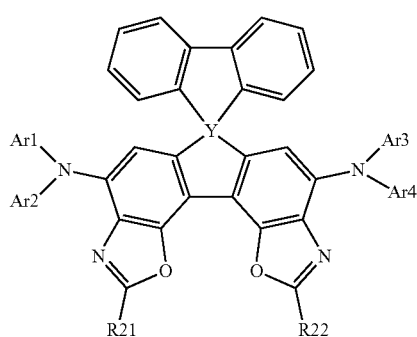

In Chemical Formulae 6 and 7,

Ar1 to Ar4, R21, R22 and Y have the same definitions as in Chemical Formula 1.

In one embodiment of the present specification, Chemical Formula 1 may be represented by any one of the following Chemical Formula 8 to Chemical Formula 11.

[Chemical Formula 8]

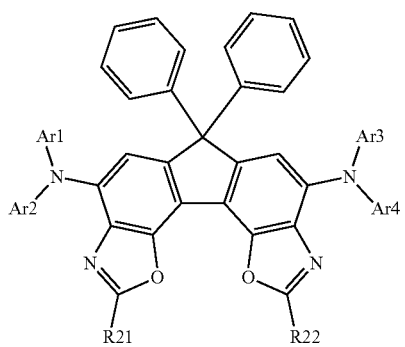

[Chemical Formula 9]

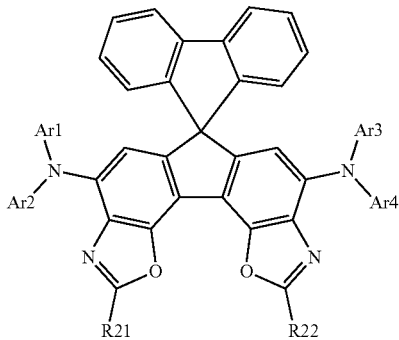

[Chemical Formula 10]

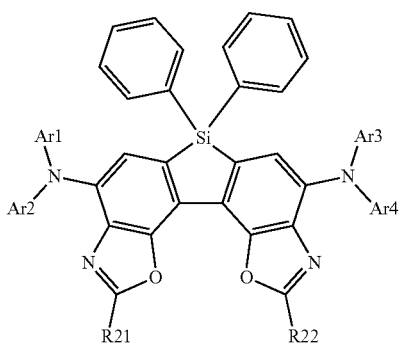

[Chemical Formula 11]

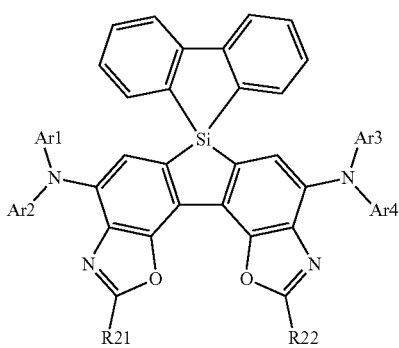

In Chemical Formulae 8 to 11,

Ar1 to Ar4, R21 and R22 have the same definitions as in Chemical Formula 1.

In one embodiment of the present specification, R21 and R22 are the same as or different from each other, and each independently hydrogen; deuterium; a substituted or unsubstituted alkyl group; a substituted or unsubstituted cycloalkyl group; a substituted or unsubstituted aryl group; or a substituted or unsubstituted heterocyclic group.

According to another embodiment, R21 and R22 are the same as or different from each other, and each independently a substituted or unsubstituted alkyl group; a substituted or unsubstituted cycloalkyl group; or a substituted or unsubstituted aryl group.

In another embodiment, R21 and R22 are the same as or different from each other, and each independently a substituted or unsubstituted alkyl group having 1 to 10 carbon atoms; a substituted or unsubstituted cycloalkyl group having 3 to 30 carbon atoms; or a substituted or unsubstituted aryl group having 6 to 30 carbon atoms.

In another embodiment, R21 and R22 are the same as or different from each other, and each independently a substituted or unsubstituted methyl group; a substituted or unsubstituted propyl group; a substituted or unsubstituted butyl group; a substituted or unsubstituted cyclohexyl group; a substituted or unsubstituted phenyl group; a substituted or unsubstituted fluorenyl group; a substituted or unsubstituted biphenyl group; or a substituted or unsubstituted naphthyl group.

According to another embodiment, R21 and R22 are the same as or different from each other, and each independently a methyl group unsubstituted or substituted with a halogen group, a cyano group, an alkyl group or an alkoxy group; a propyl group unsubstituted or substituted with a halogen group, a cyano group, an alkyl group or an alkoxy group; a butyl group unsubstituted or substituted with a halogen group, a cyano group, an alkyl group or an alkoxy group; a cyclohexyl group unsubstituted or substituted with a halogen group, a cyano group, an alkyl group or an alkoxy group; a phenyl group unsubstituted or substituted with a halogen group, a cyano group, an alkyl group or an alkoxy group; a fluorenyl group unsubstituted or substituted with a halogen group, a cyano group, an alkyl group or an alkoxy group; a biphenyl group unsubstituted or substituted with a halogen group, a cyano group, an alkyl group or an alkoxy group; or a naphthyl group unsubstituted or substituted with a halogen group, a cyano group, an alkyl group or an alkoxy group.

According to another embodiment, R21 and R22 are the same as or different from each other, and each independently a methyl group; an isopropyl group; a tert-butyl group; a cyclohexyl group; a phenyl group unsubstituted or substituted with fluorine (F), a cyano group, a methyl group or a methoxy group; a fluorenyl group unsubstituted or substituted with fluorine (F), a cyano group, a methyl group or a methoxy group; a biphenyl group unsubstituted or substituted with fluorine (F), a cyano group, a methyl group or a methoxy group; or a naphthyl group unsubstituted or substituted with fluorine (F), a cyano group, a methyl group or a methoxy group.

In one embodiment of the present specification, Chemical Formula 1 may be represented by any one of the following structures.

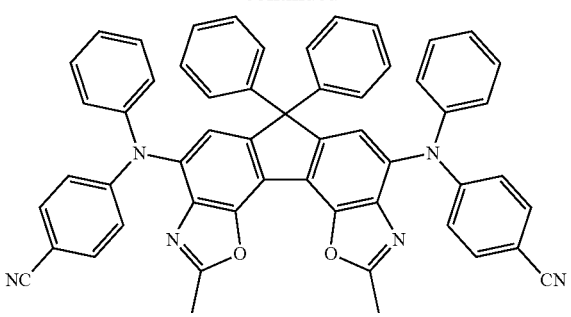

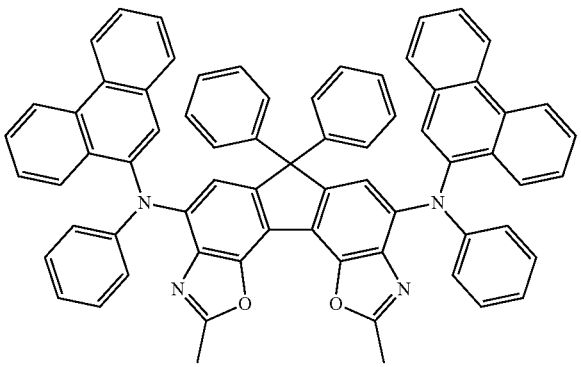

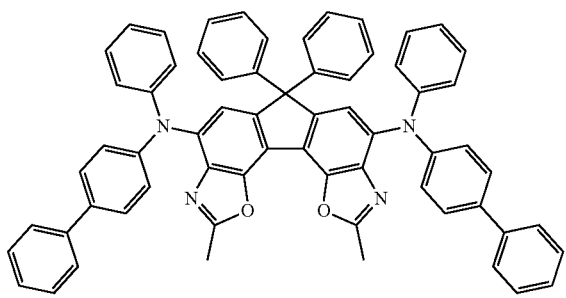

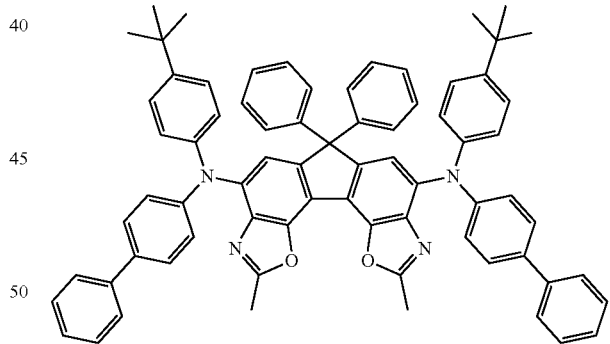

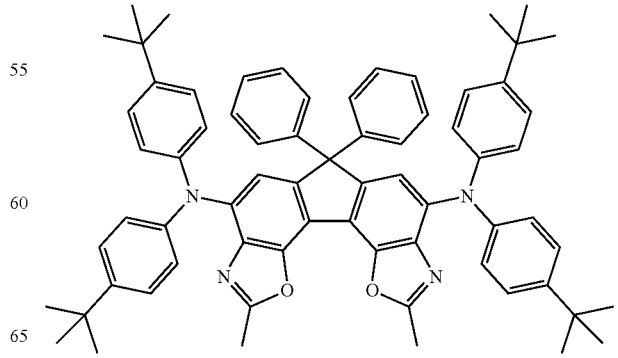

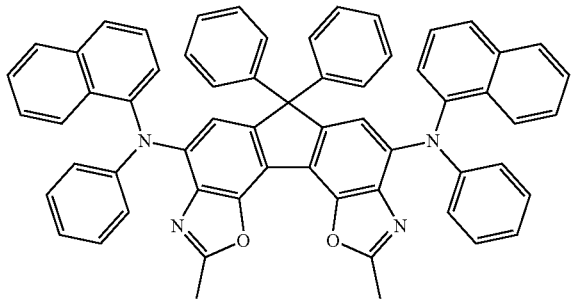
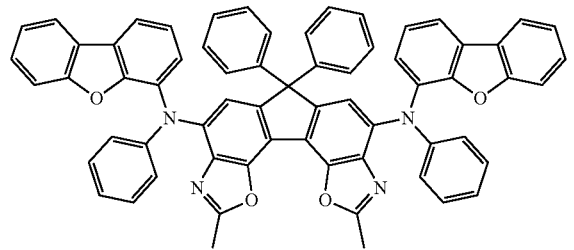
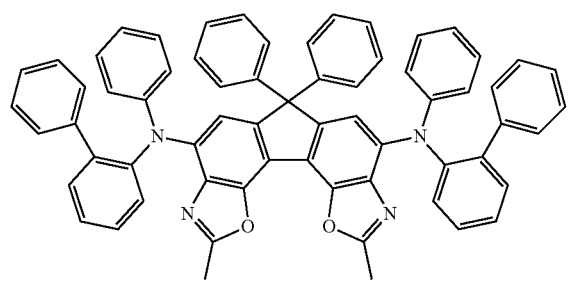
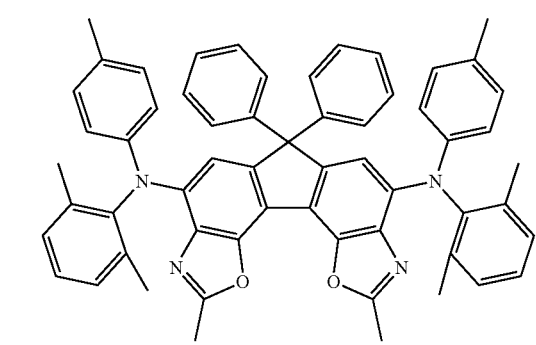
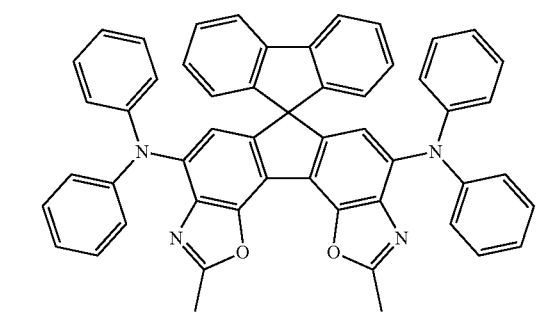
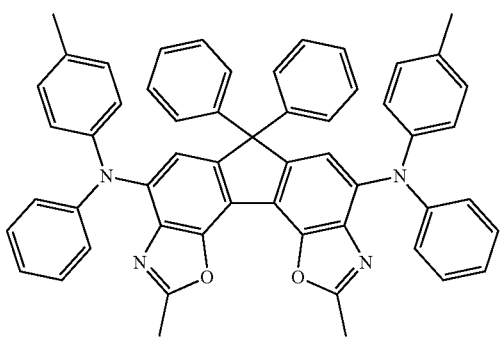
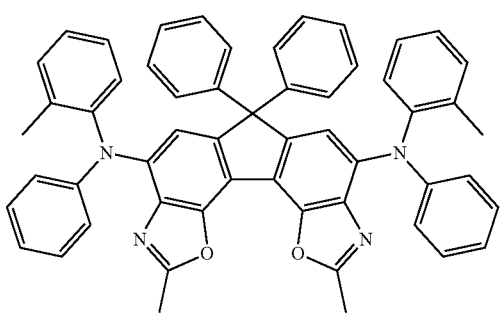
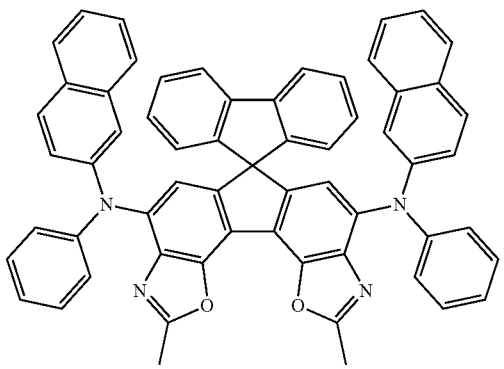
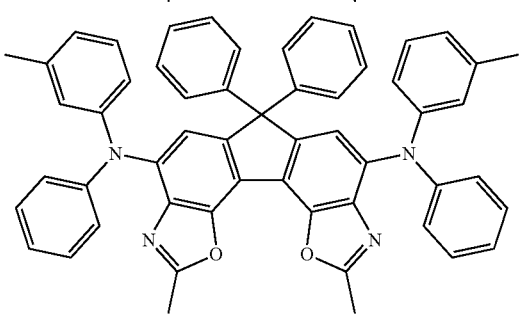
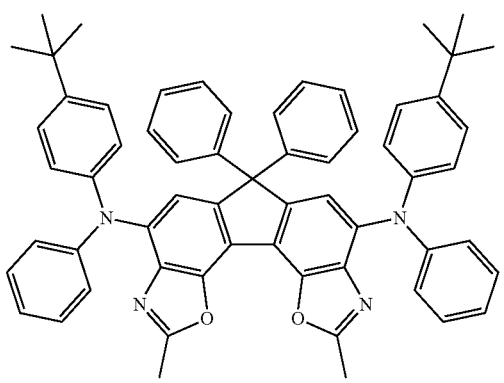 [SMILES: Cc1nc2c(N(c3ccccc3)c3ccc(C(C)(C)C)cc3)cc3c(c2o1)-c1c(cc(N(c2ccccc2)c2ccc(C(C)(C)C)cc2)c2nc(C)oc12)C3(c1ccccc1)c1ccccc1]

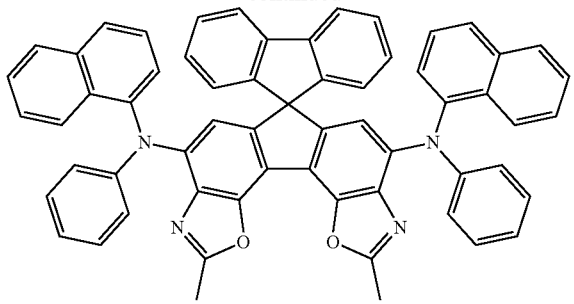
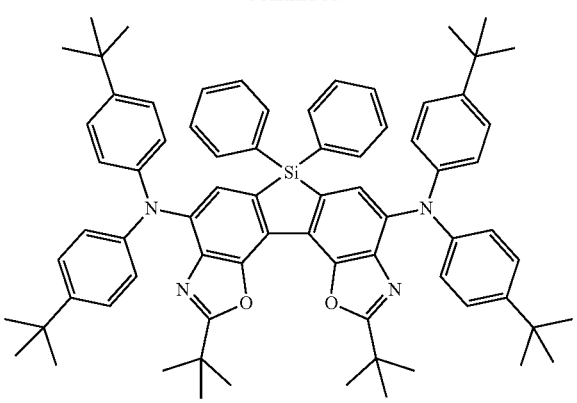
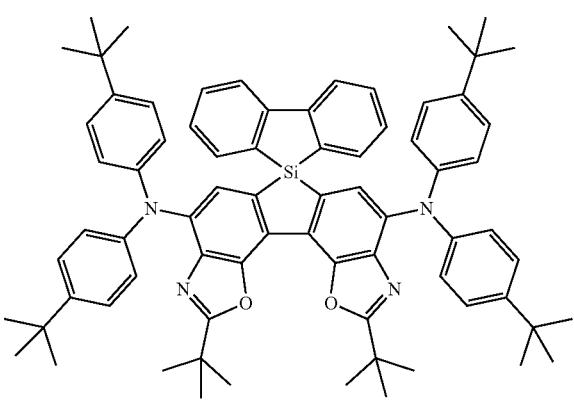
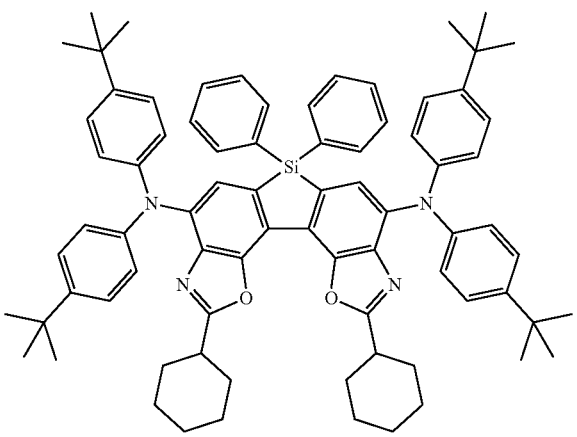
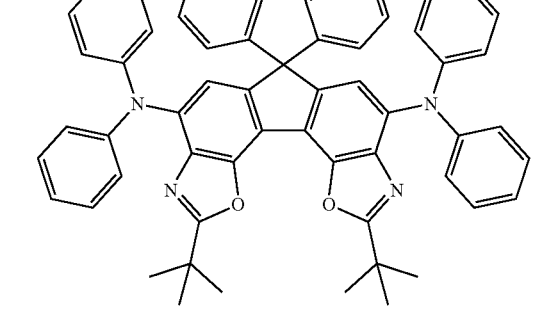

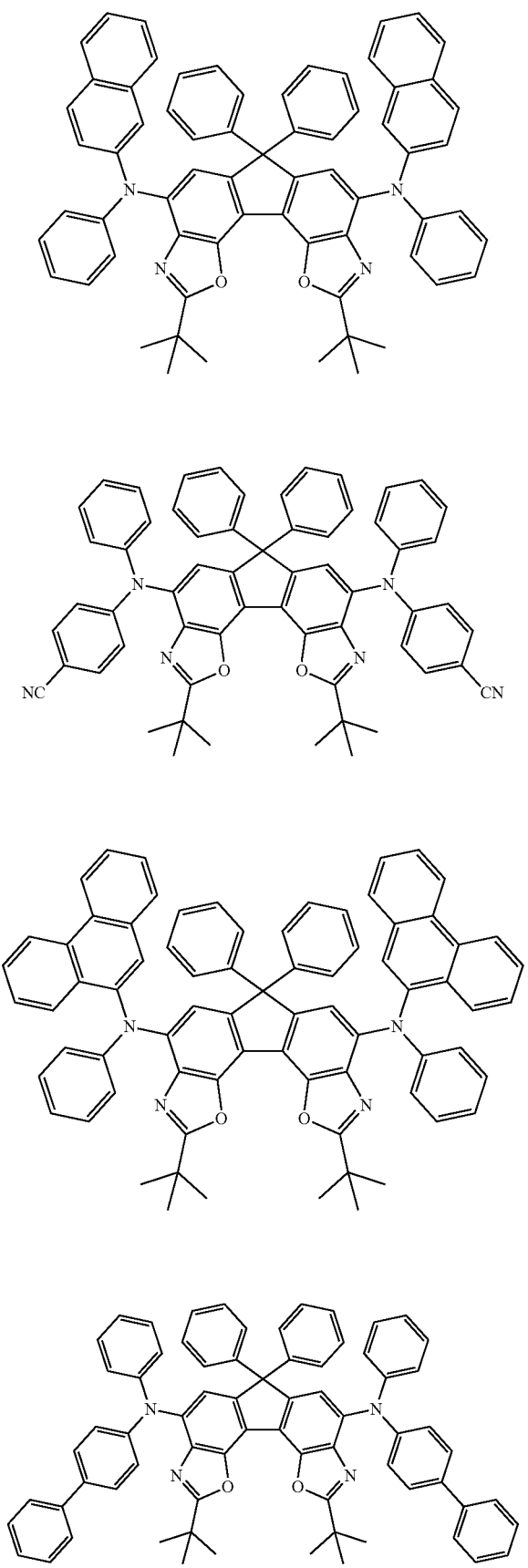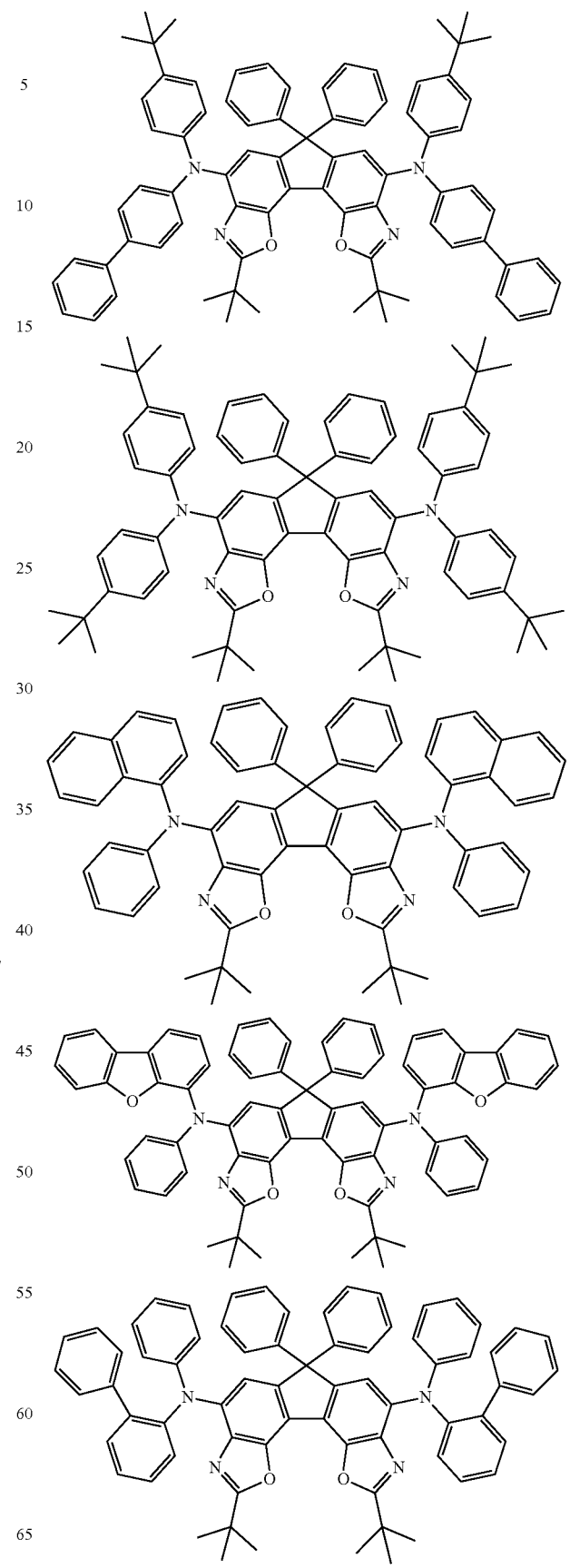

21
-continued
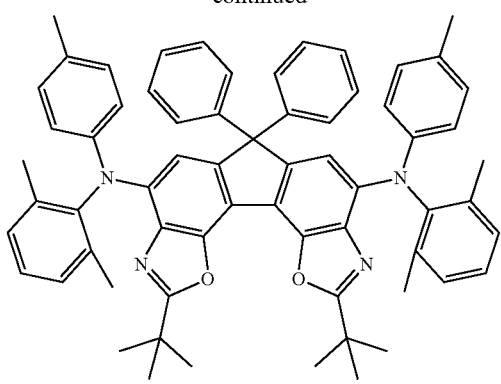
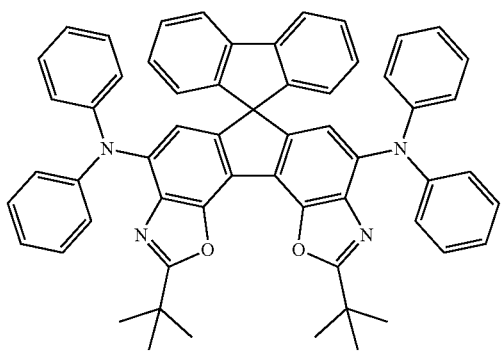
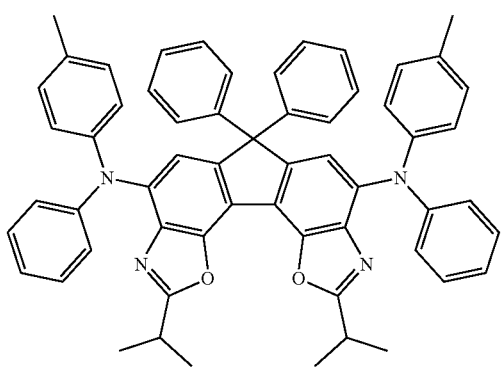
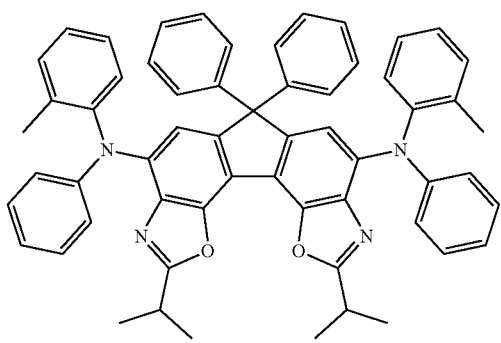
22
-continued
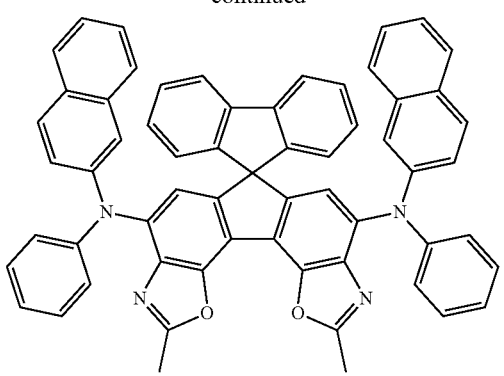
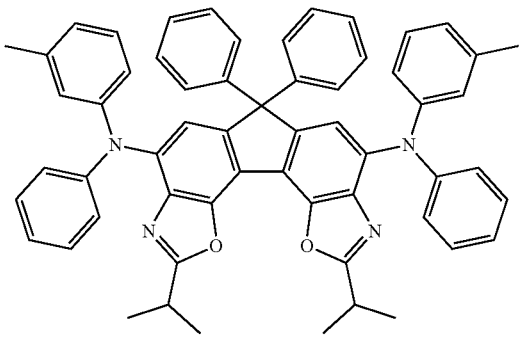
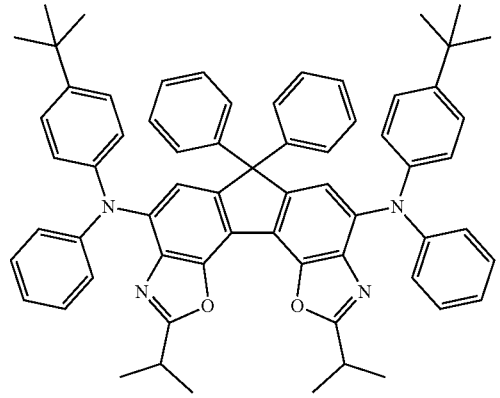
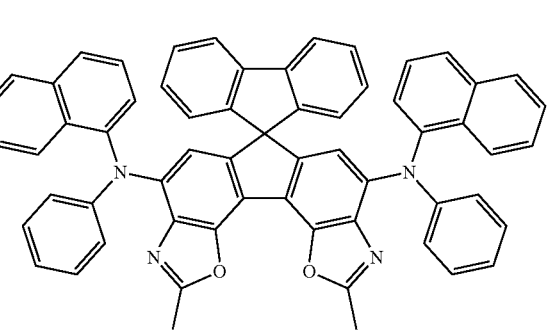

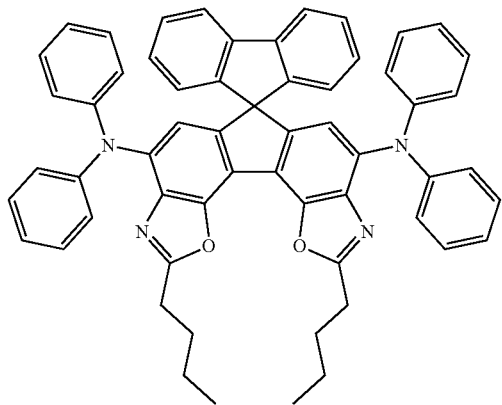
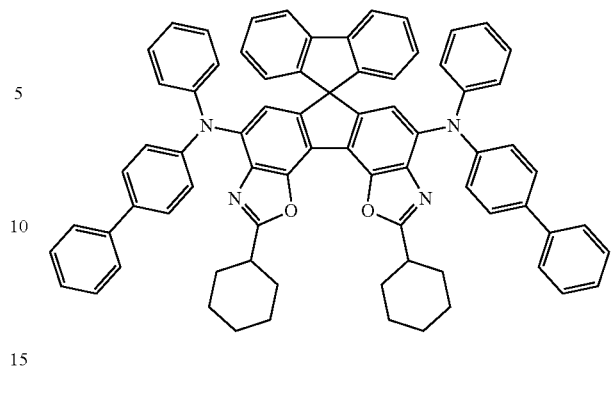
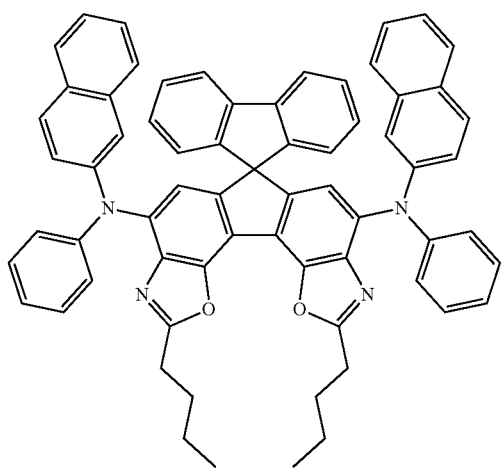
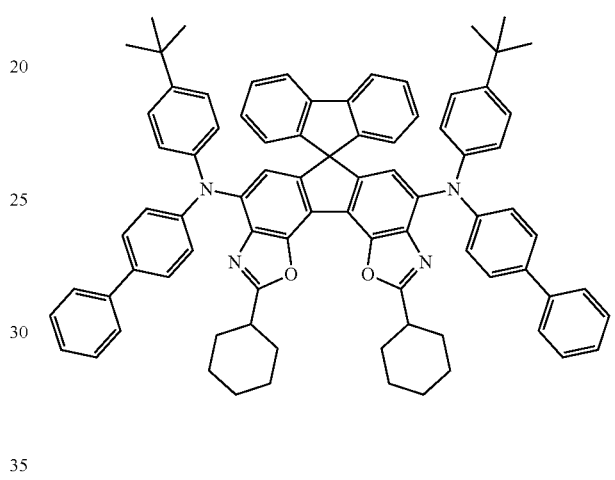
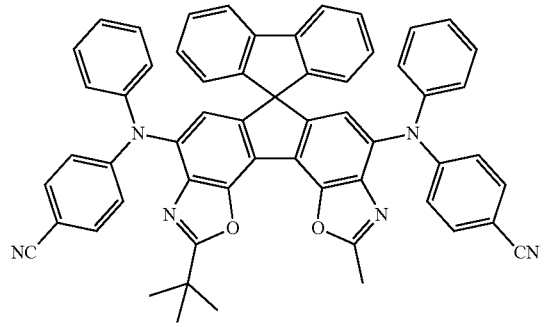
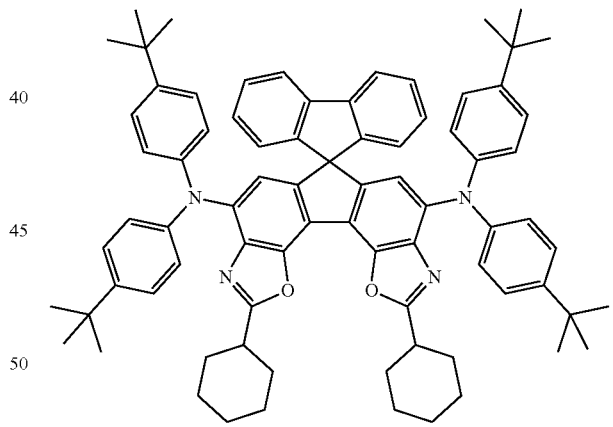
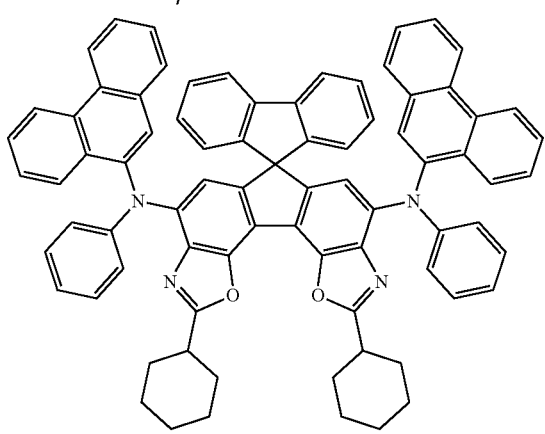
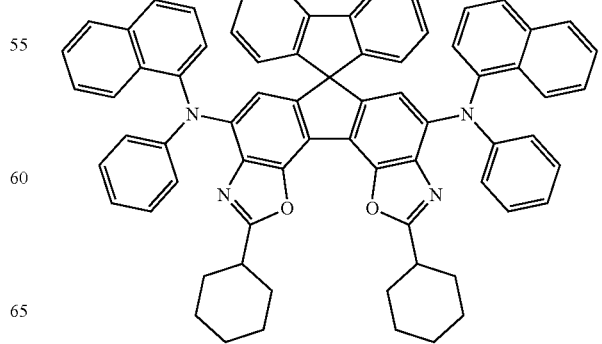

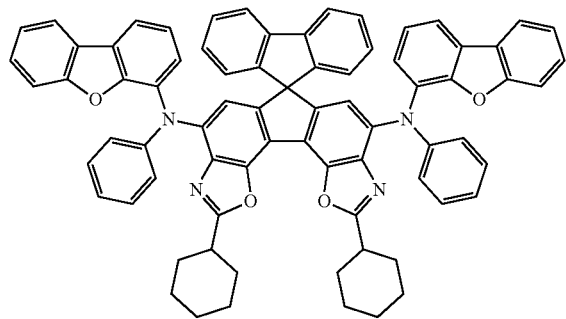
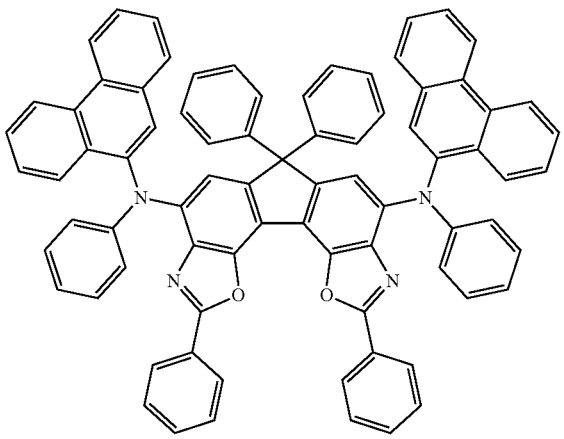
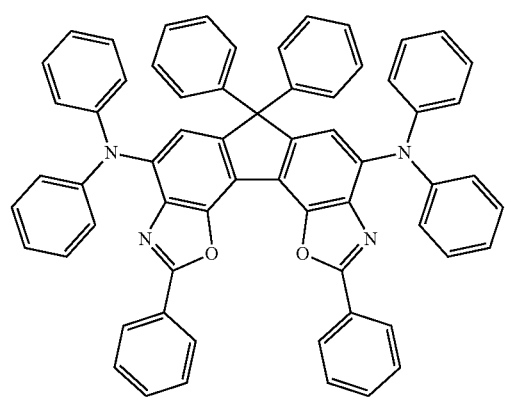
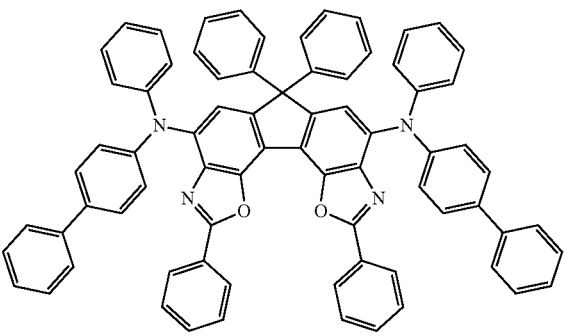
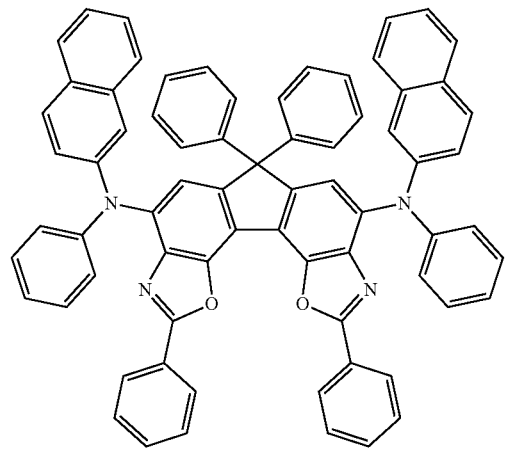
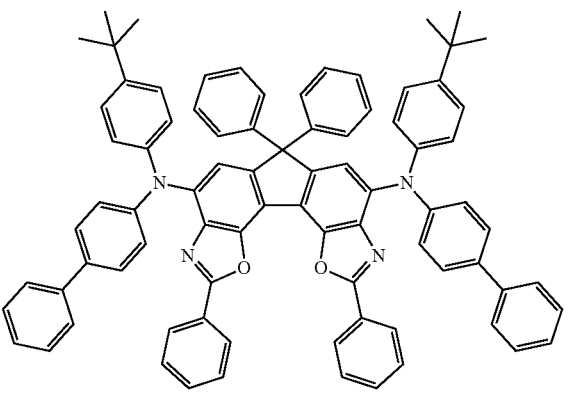
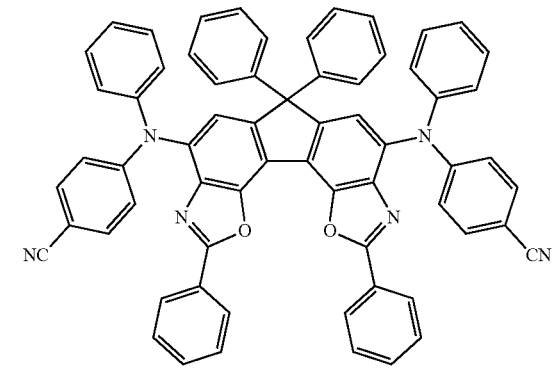
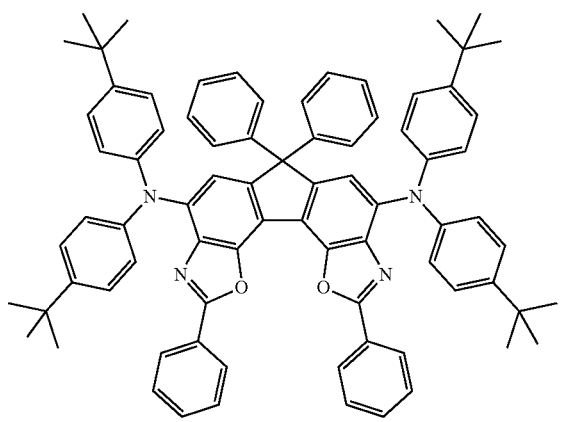

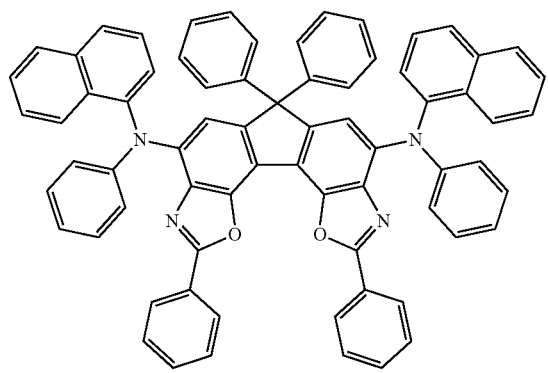
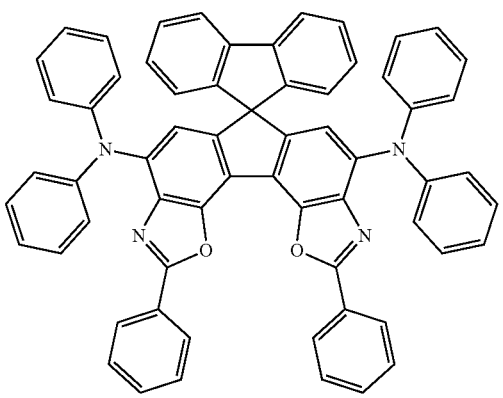
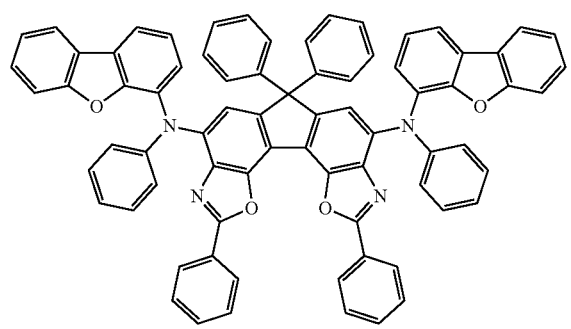
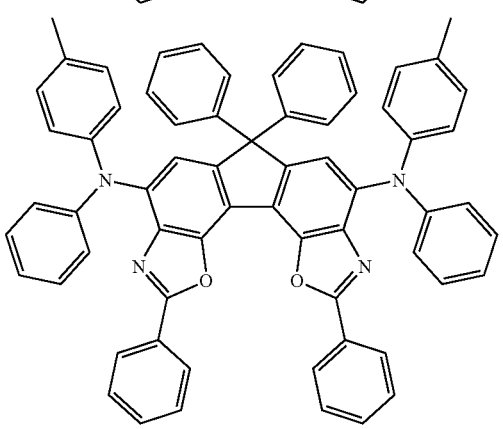
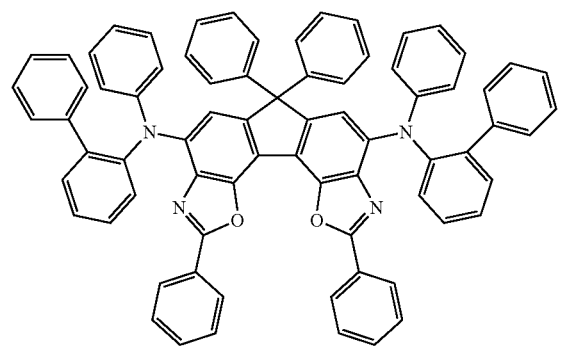
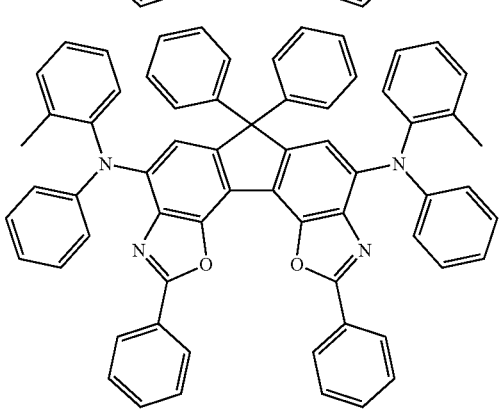
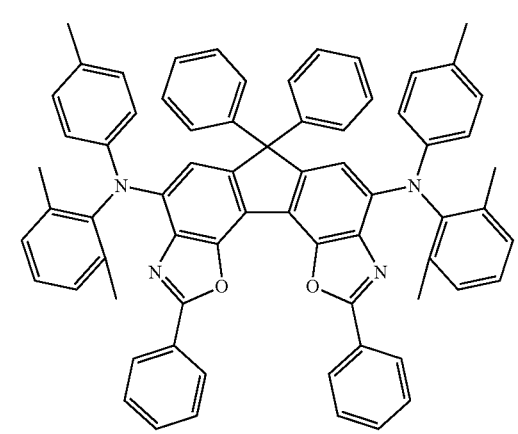
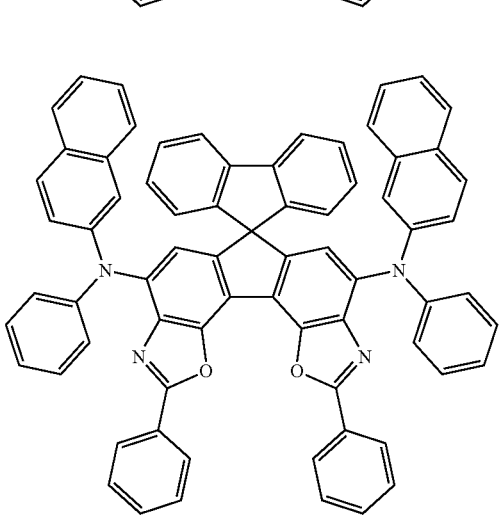

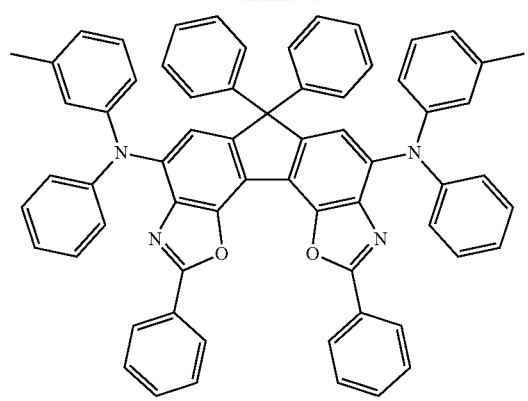
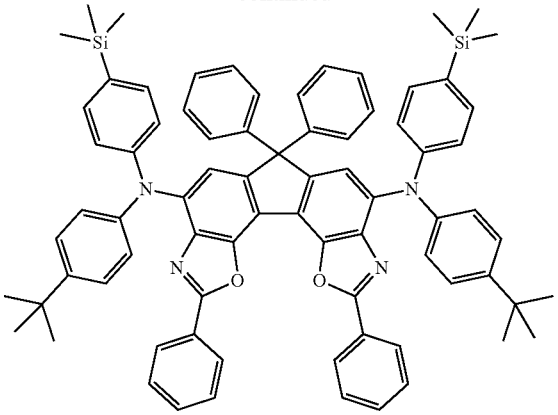 [SMILES: Cc1cccc(C)c1-c1nc2c(N(c3ccc(C(C)(C)C)cc3)c3ccc(C(C)(C)C)cc3)cc3c(c2o1)-c1c(cc(N(c2ccc(C(C)(C)C)cc2)c2ccc(C(C)(C)C)cc2)c2nc(-c4c(C)cccc4C)oc12)C3(c1ccccc1)c1ccccc1]
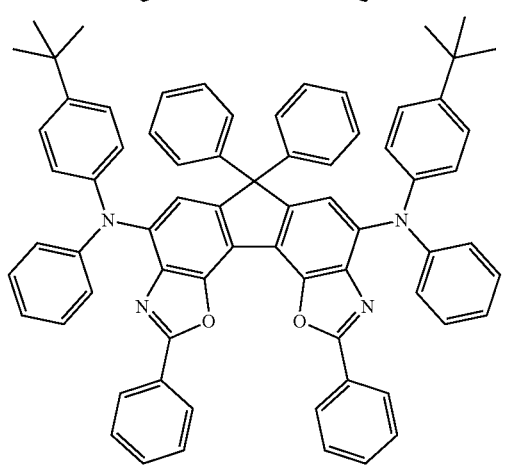
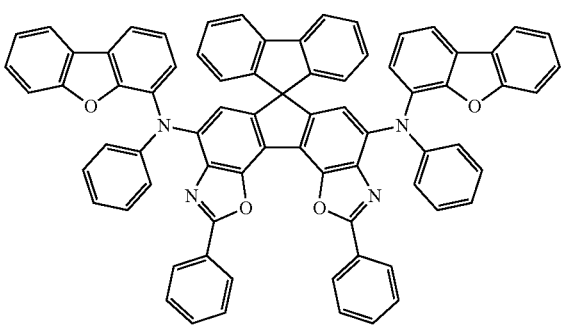
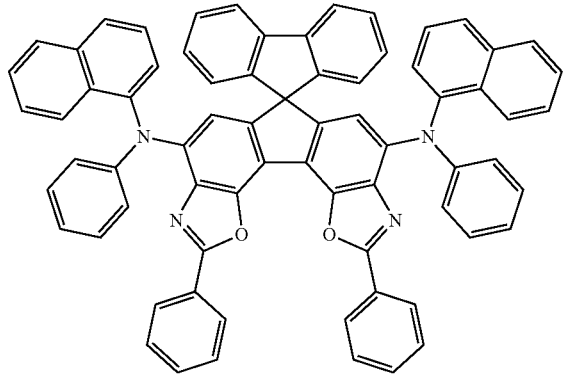
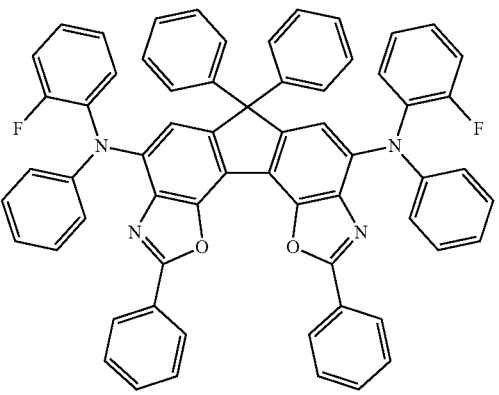
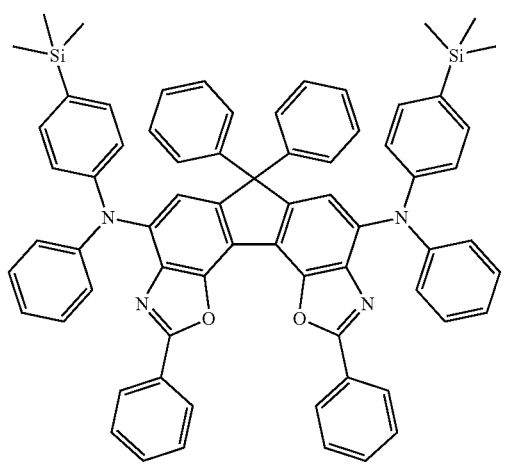
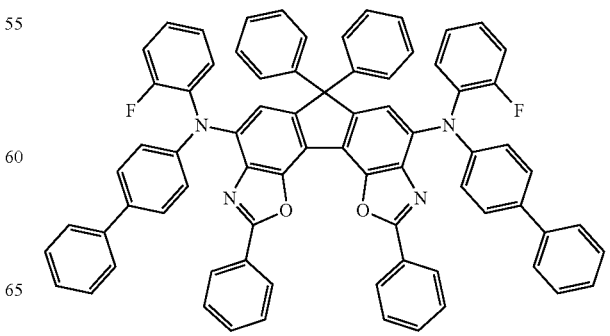

31
-continued
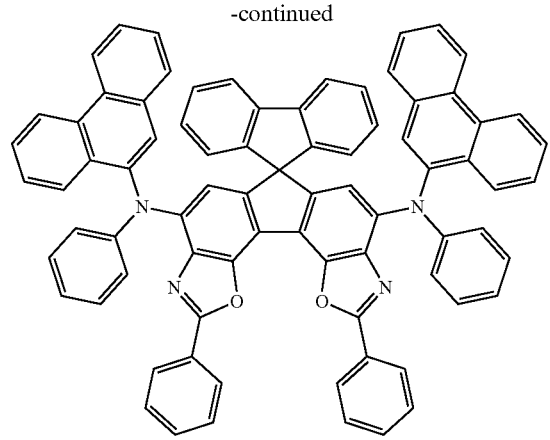
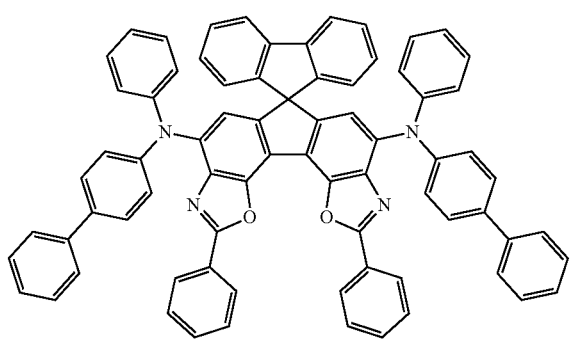
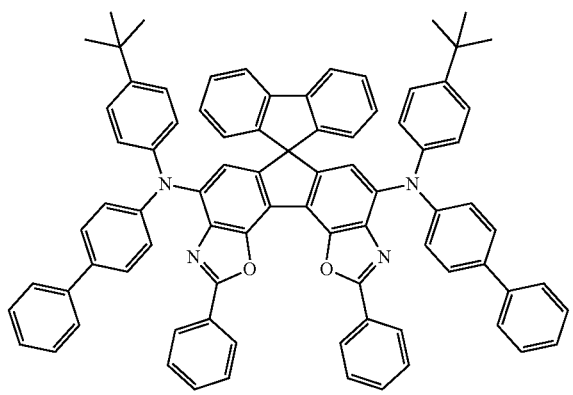
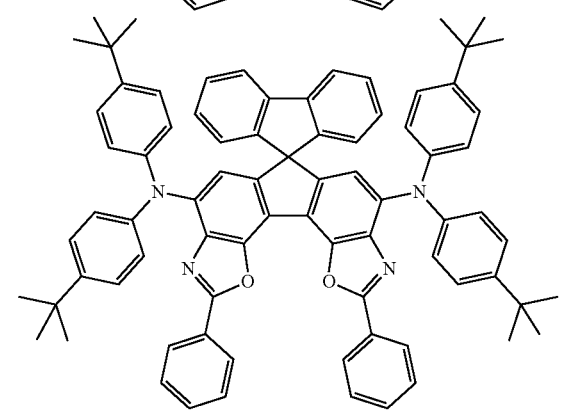
32
-continued
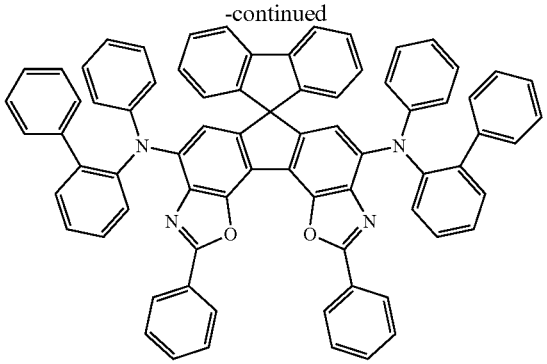
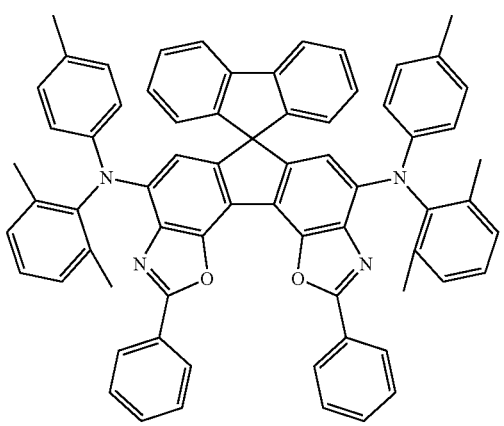
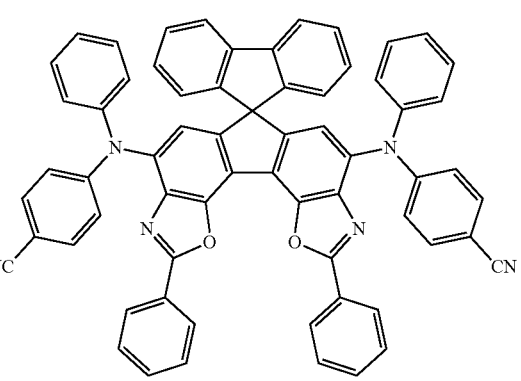
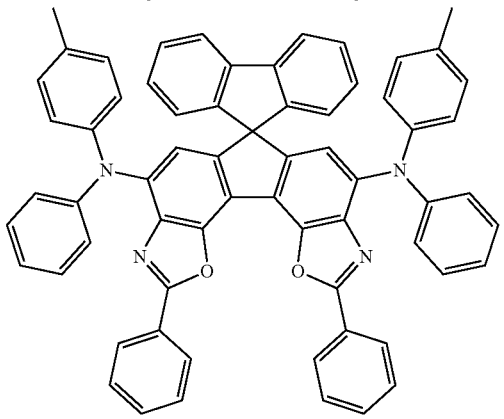

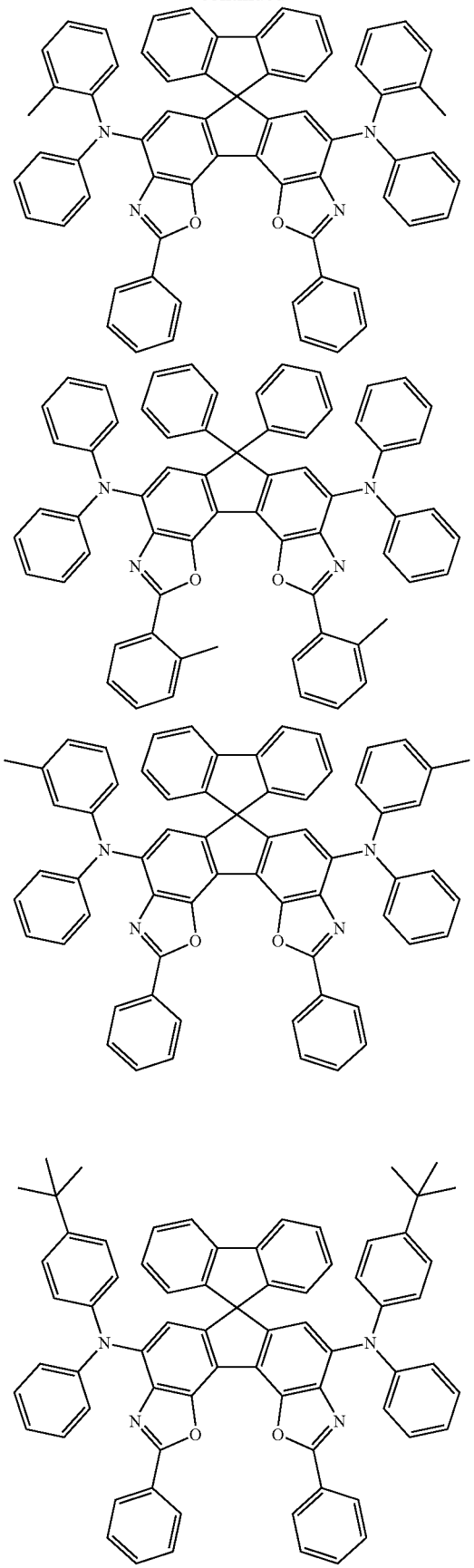
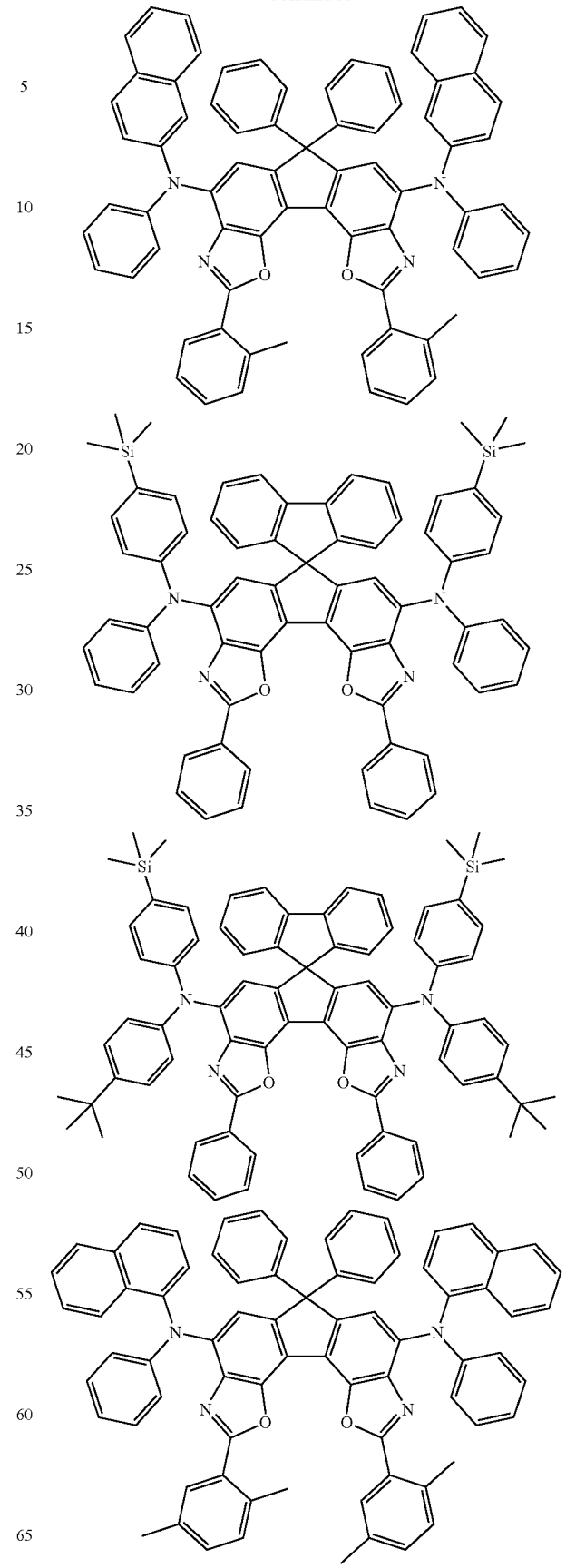

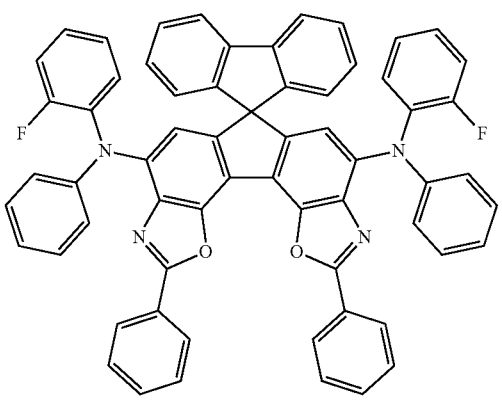 [SMILES: Cc1ccccc1N(c1ccccc1)c1cc2c(c3oc(-c4ccccc4F)nc13)-c1c(cc(N(c3ccccc3)c3ccccc3C)c3nc(-c4ccccc4F)oc13)C2(c1ccccc1)c1ccccc1]
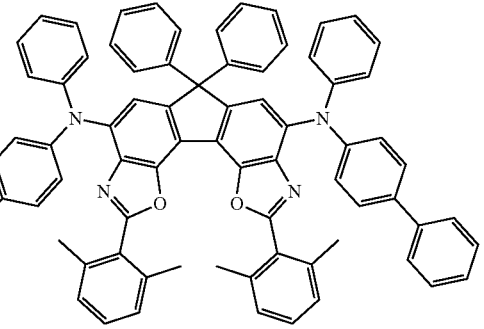
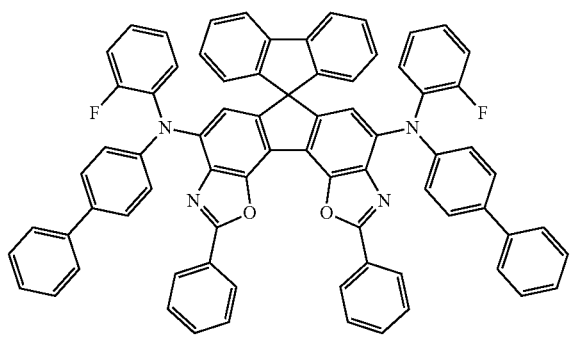
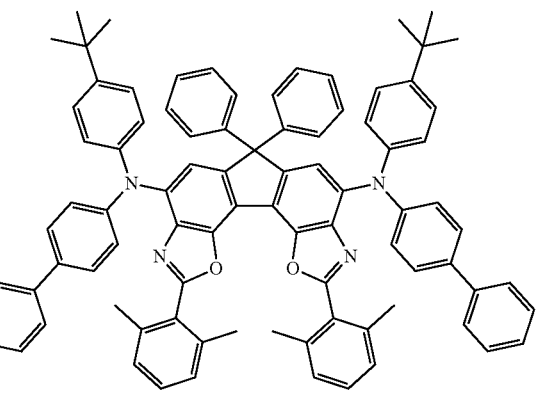
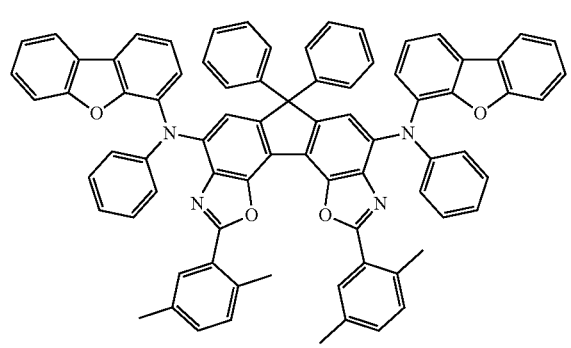
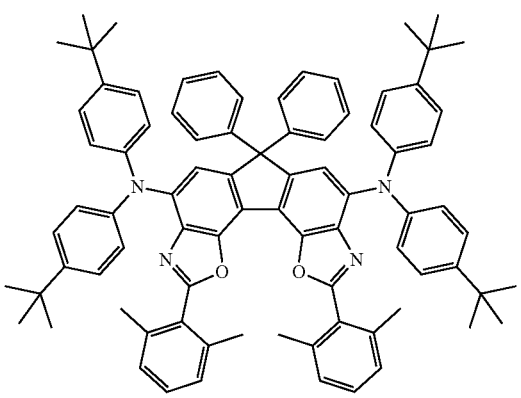
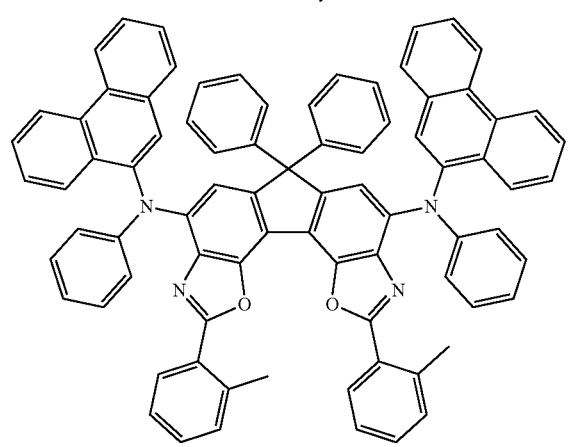
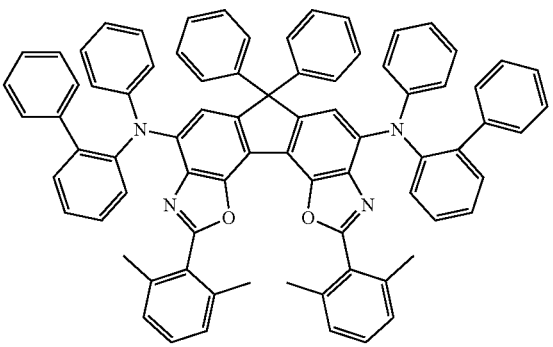

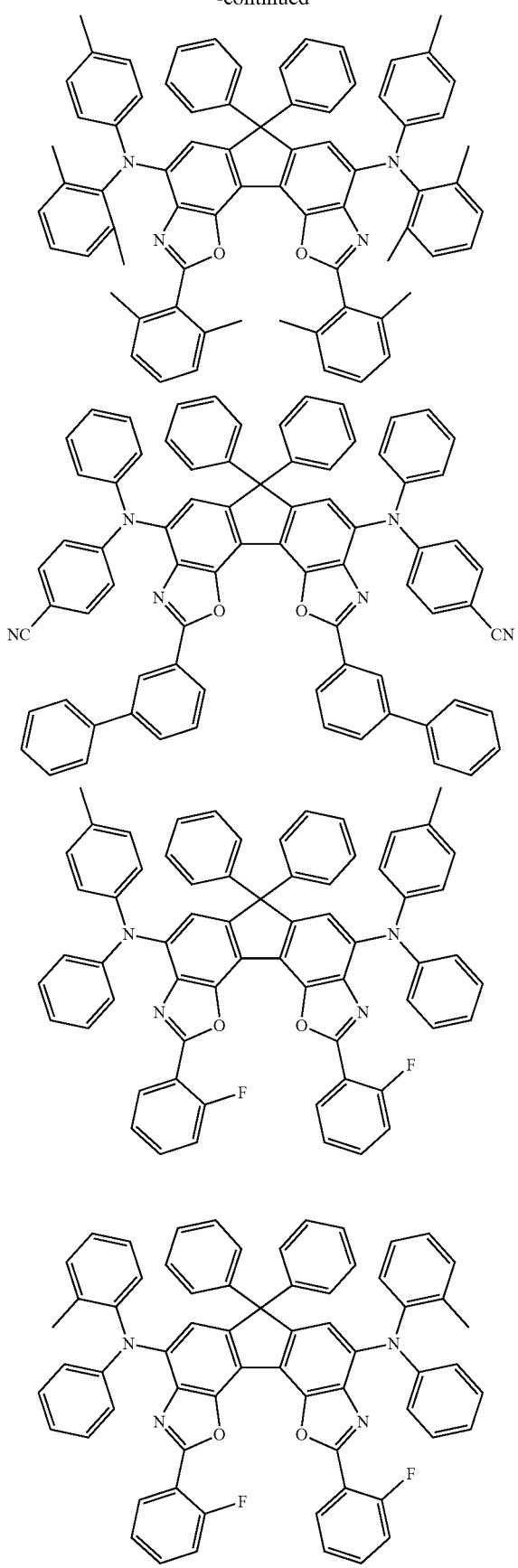
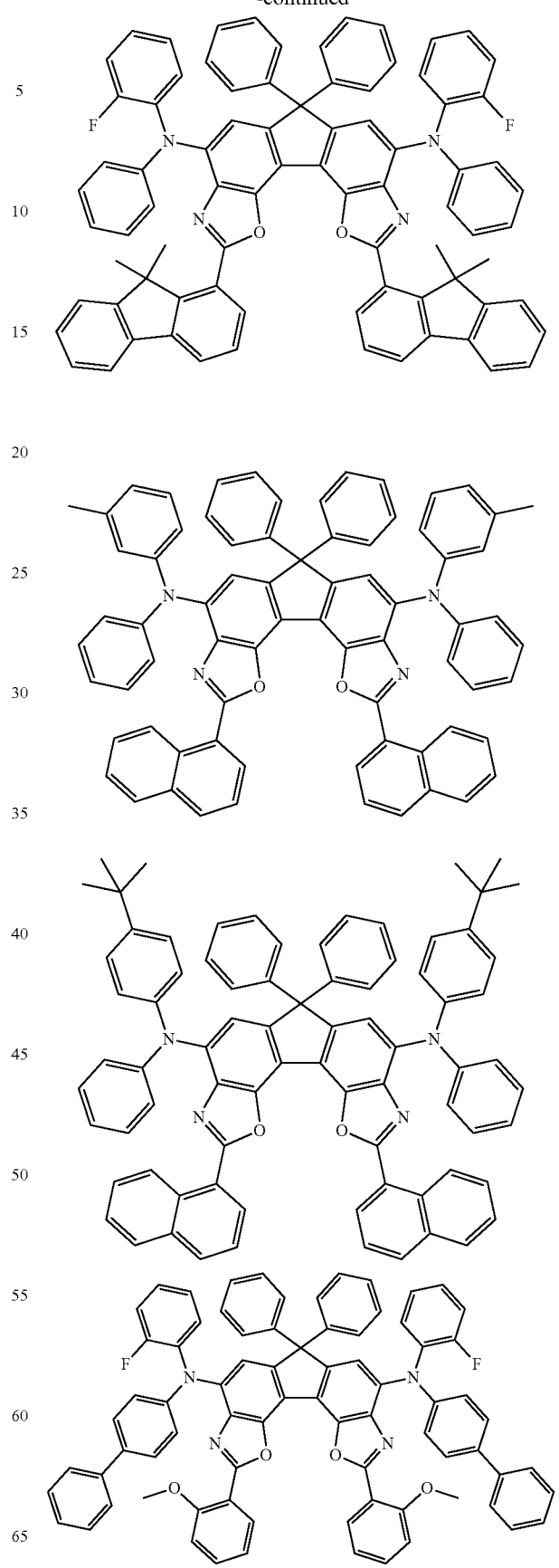

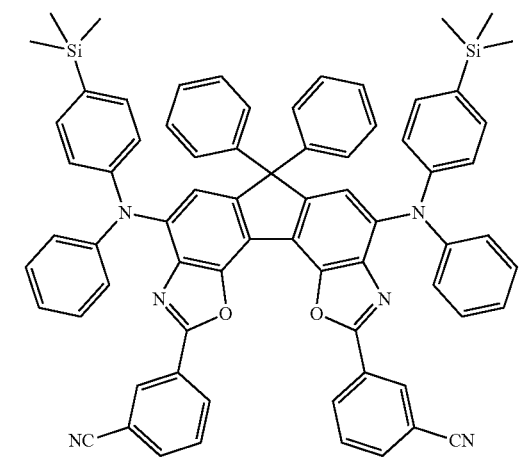
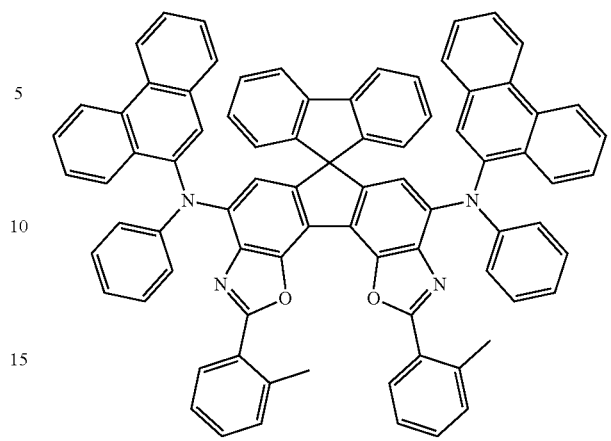
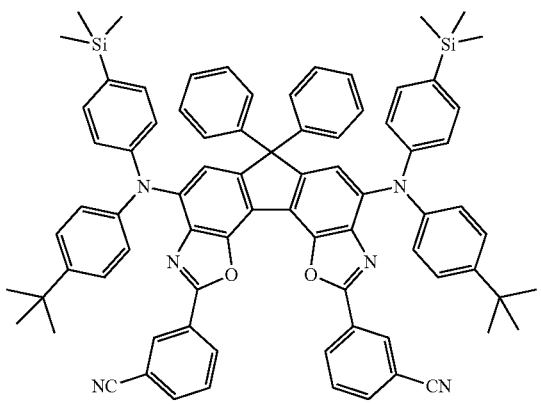
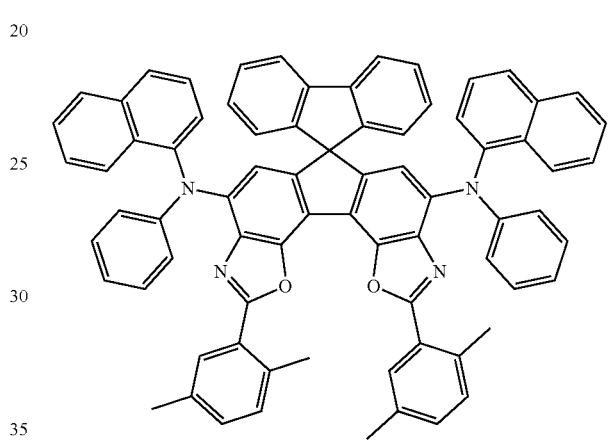
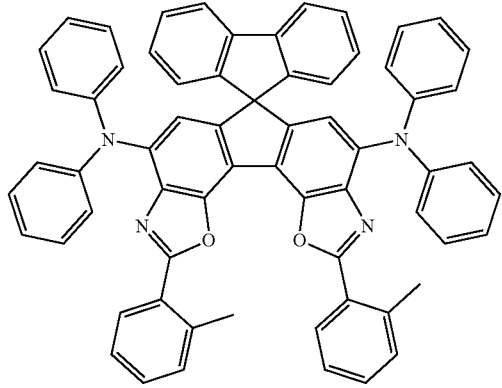
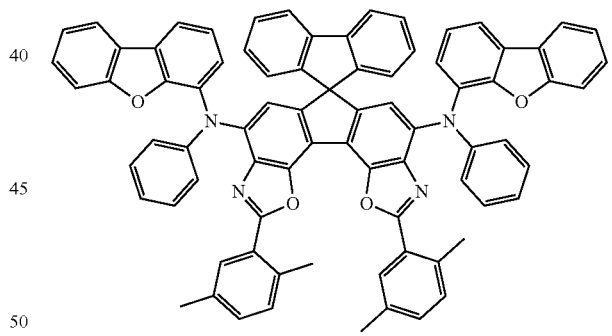
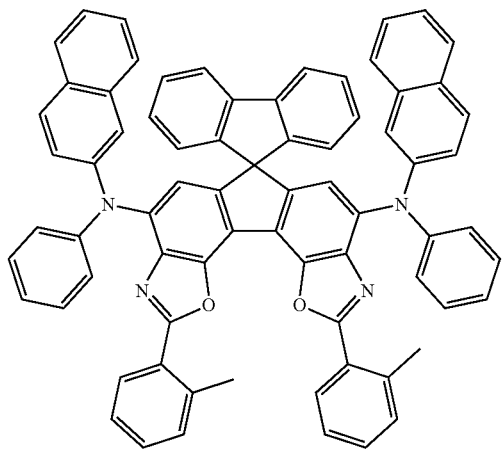
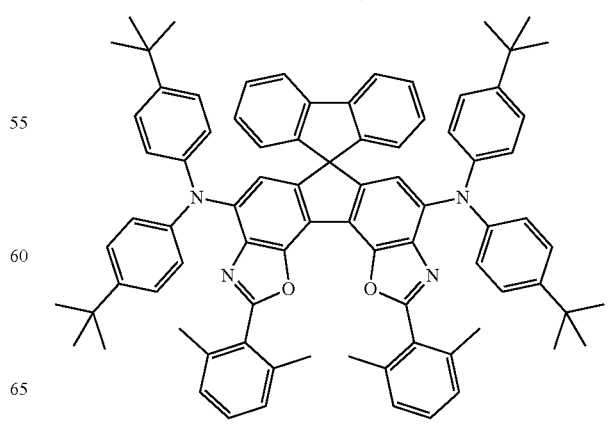

-continued
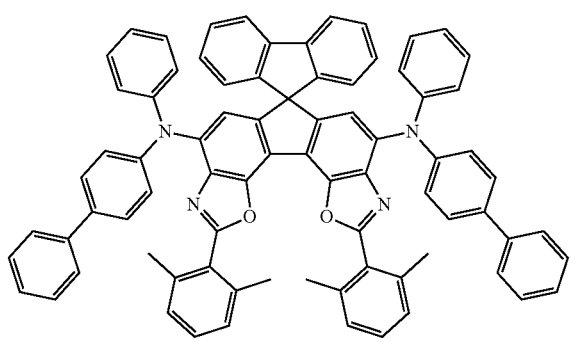
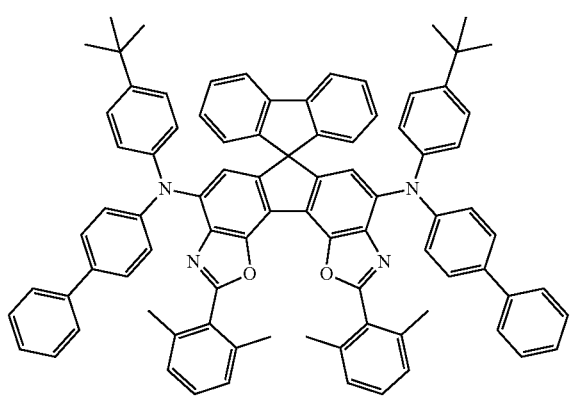
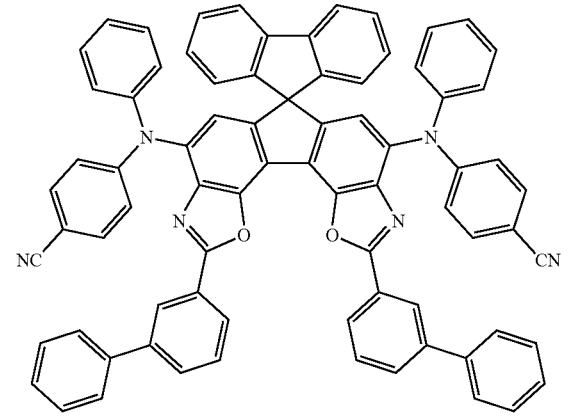
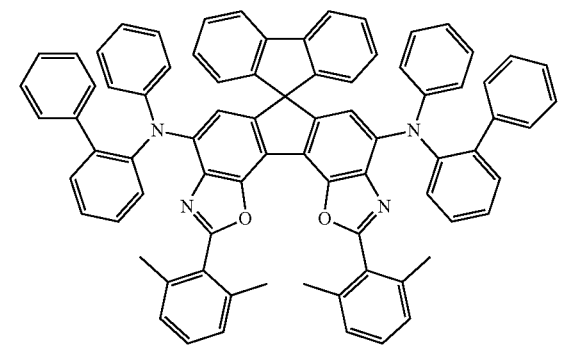
-continued
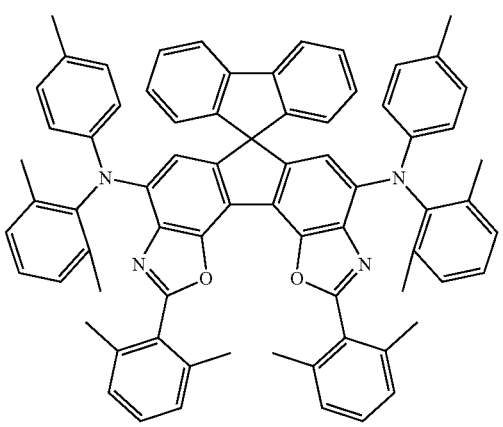
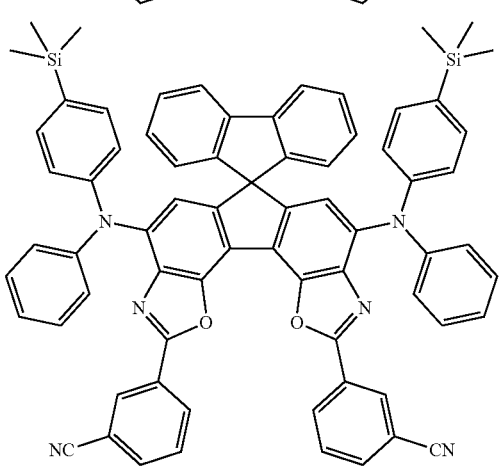
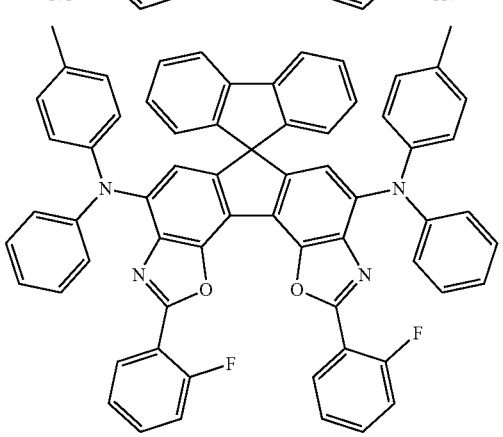
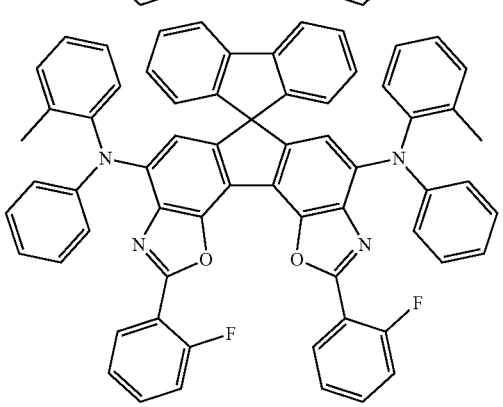

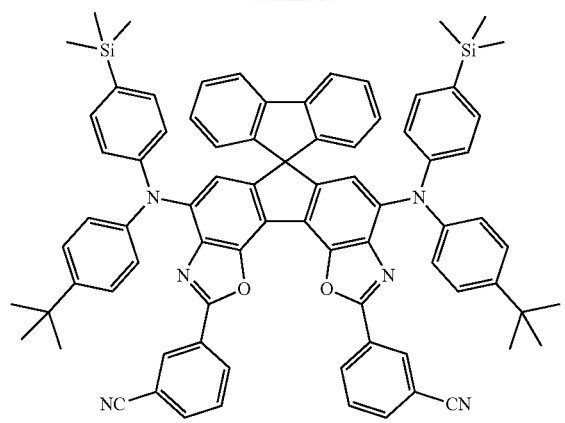
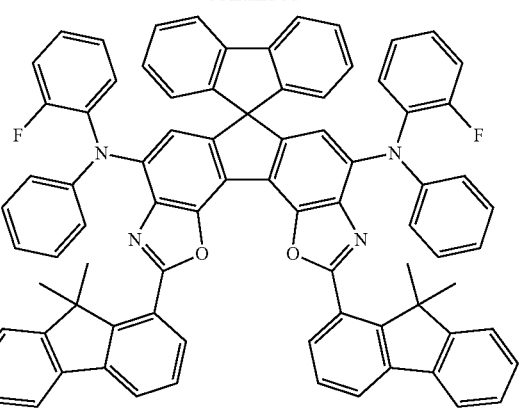
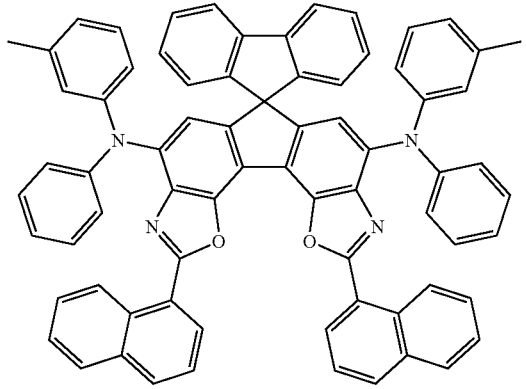
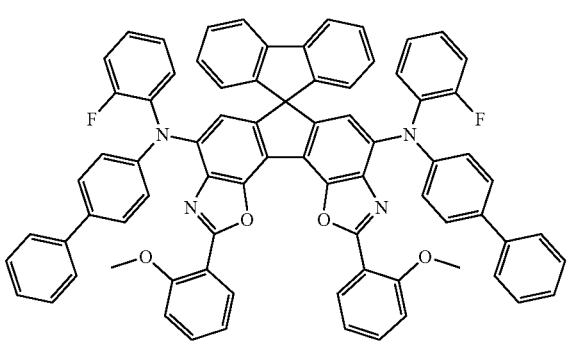
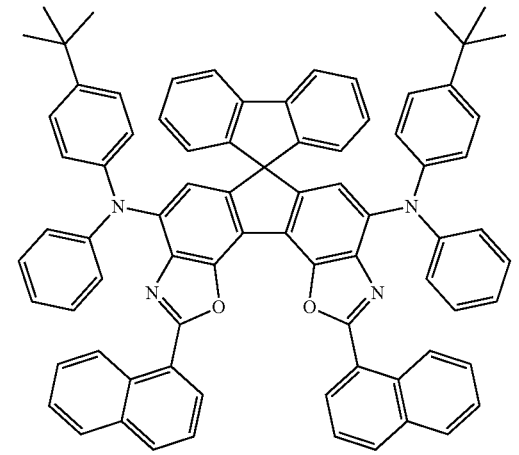
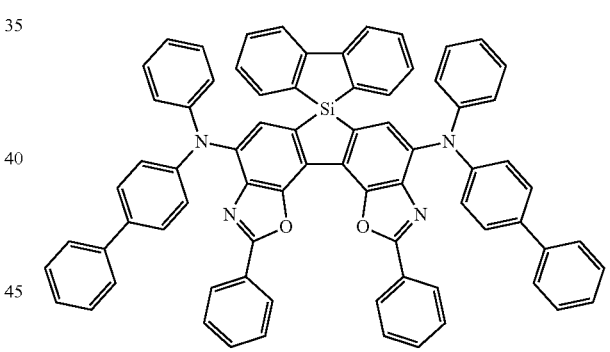
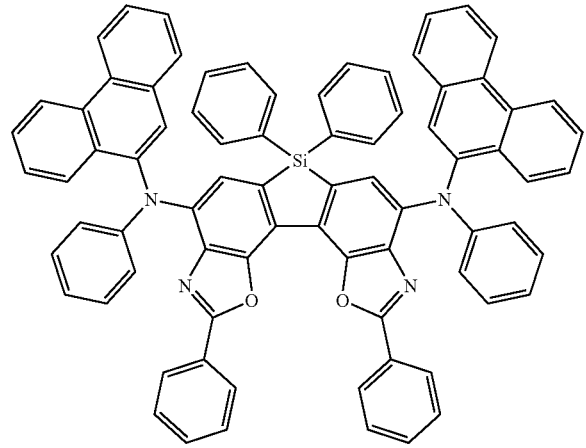
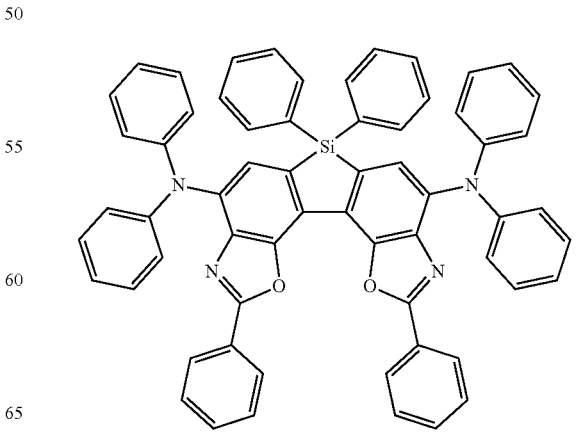

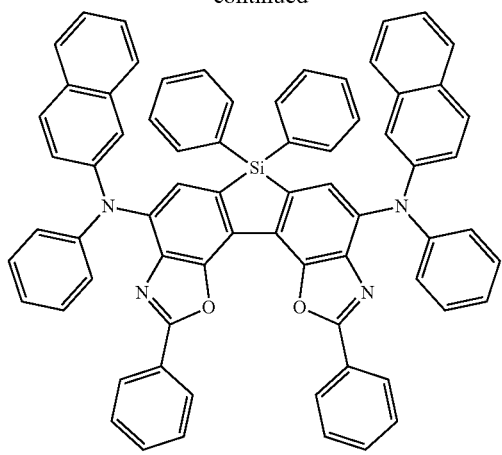
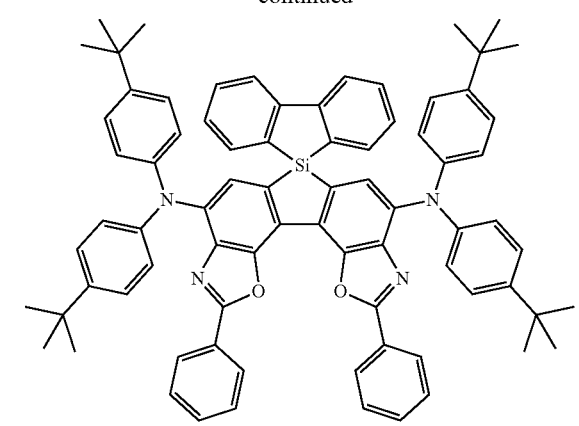
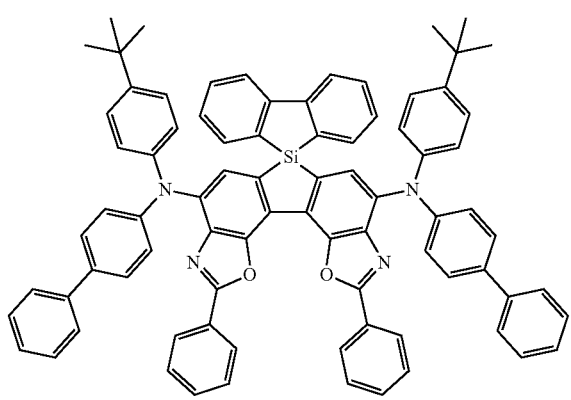
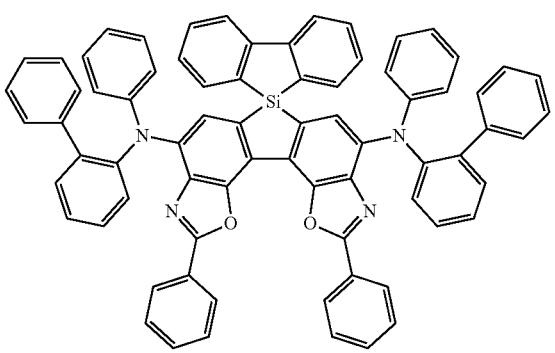
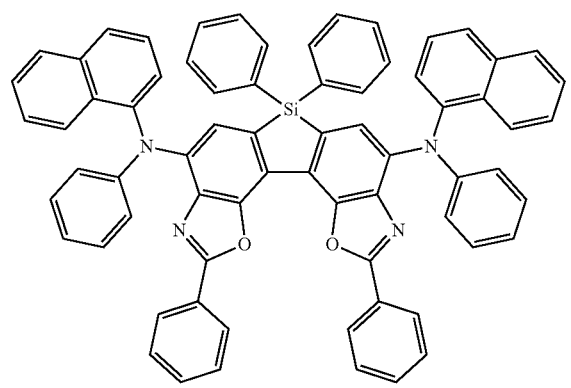
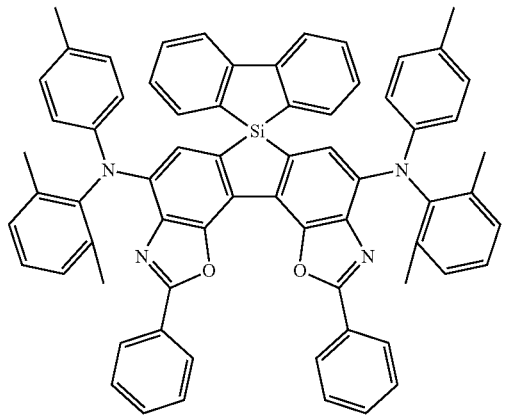
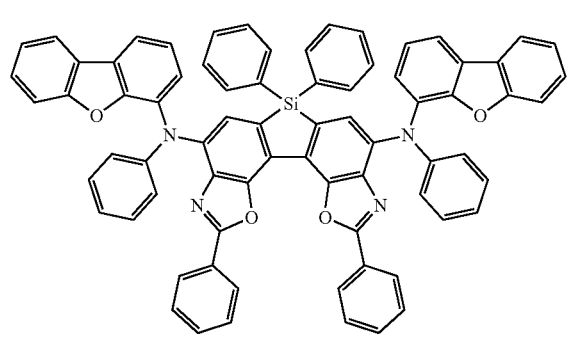
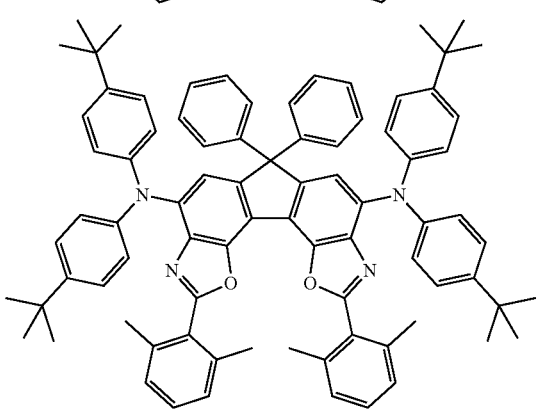

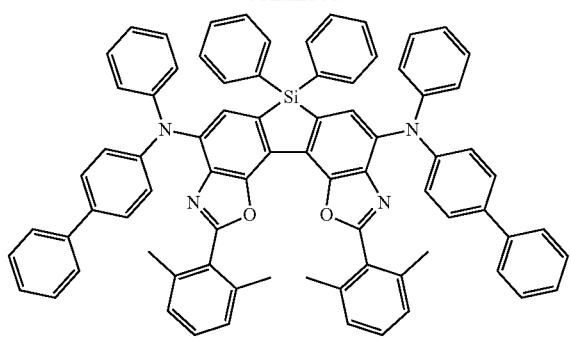
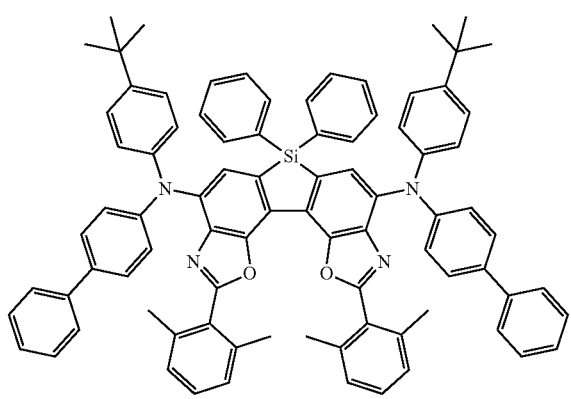
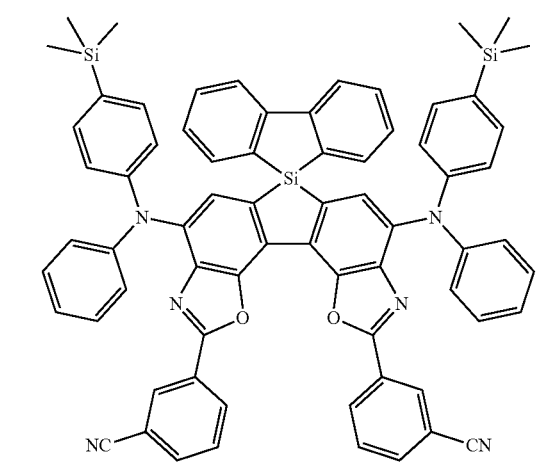
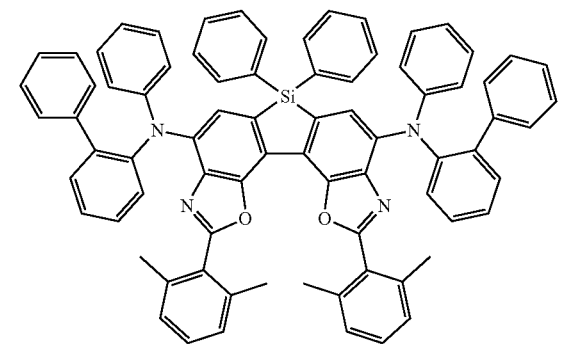
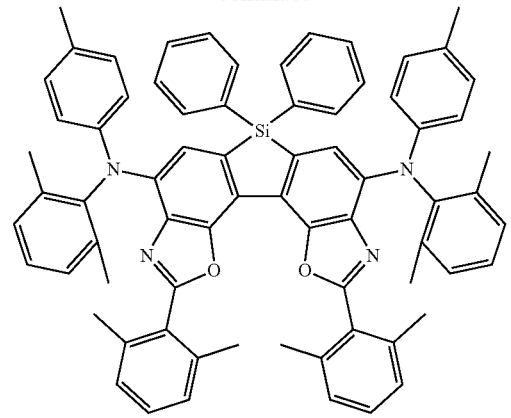
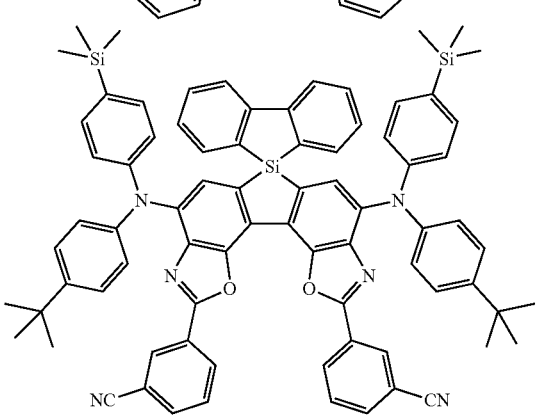
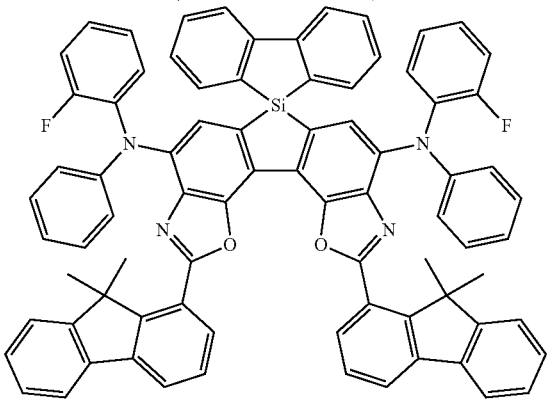
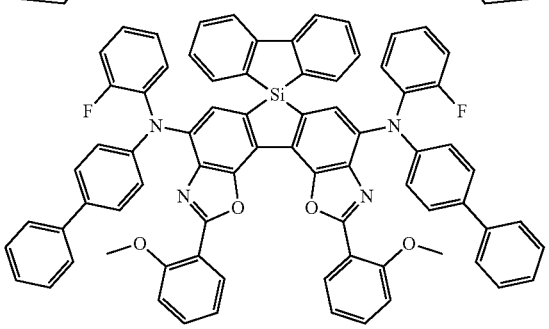
The core structure of Chemical Formula 1 according to one embodiment of the present specification may be prepared as in the synthesis methods of specific compounds to describe below.
Substituents of the heterocyclic compound of Chemical Formula 1 may bond using methods known in the art, and types, positions or the number of the substituents may vary depending on technologies known in the art.

A conjugation length of a compound and an energy band gap thereof are closely related. Specifically, as a conjugation length of a compound increases, an energy band gap thereof decreases.

By introducing various substituents to the core structure as above, compounds having various energy band gaps may be synthesized in the present disclosure. In addition, by introducing various substituents to the core structure having structures as above, HOMO and LUMO energy levels of the compound may also be controlled in the present disclosure.

In addition, by introducing various substituents to the core structure having structures as above, compounds having unique properties of the introduced substituents may be synthesized. For example, by introducing substituents normally used in a hole injection layer material, a material for hole transfer, a light emitting layer material and an electron transfer layer material used for manufacturing an organic light emitting device to the core structure, materials satisfying needs required from each organic material layer may be synthesized.

In addition, an organic light emitting device according to the present disclosure includes a first electrode; a second electrode provided to face the first electrode; and one or more organic material layers provided between the first electrode and the second electrode, wherein one or more layers of the one or more organic material layers include the heterocyclic compound of Chemical Formula 1.

The organic light emitting device of the present disclosure may be prepared using common methods and materials for preparing an organic light emitting device except that one or more organic material layers are formed using the compound described above.

The compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, but may be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

In the organic light emitting device of the present disclosure, the organic material layer may include an electron transfer layer or an electron injection layer, and the electron transfer layer or the electron injection layer may include the heterocyclic compound represented by Chemical Formula 1.

In the organic light emitting device of the present disclosure, the organic material layer may include a hole injection layer or a hole transfer layer, and the hole injection layer or the hole transfer layer may include the heterocyclic compound represented by Chemical Formula 1.

In another embodiment, the organic material layer includes a light emitting layer, and the light emitting layer includes the heterocyclic compound represented by Chemical Formula 1. As one example, the heterocyclic compound represented by Chemical Formula 1 may be included as a dopant of the light emitting layer.

According to another embodiment, the organic material layer includes a light emitting layer, and the light emitting layer includes the heterocyclic compound represented by Chemical Formula 1 as a dopant and includes other organic compounds as a host. In this case, the dopant may be included in 0.1 parts by weight to 10 parts by weight and preferably in 1 parts by weight to 5 parts by weight based on 100 parts by weight of the host in the light emitting layer.

As another example, the organic material layer including the heterocyclic compound represented by Chemical Formula 1 includes the heterocyclic compound represented by Chemical Formula 1 as a dopant, and may include a fluorescent host or a phosphorescent host.

In another embodiment, the organic material layer including the heterocyclic compound represented by Chemical Formula 1 includes the heterocyclic compound represented by Chemical Formula 1 as a dopant, includes a fluorescent host or a phosphorescent host, and may include other organic compounds, metals or metal compounds as a dopant.

As another example, the organic material layer including the heterocyclic compound represented by Chemical Formula 1 includes the heterocyclic compound represented by Chemical Formula 1 as a dopant, includes a fluorescent host or a phosphorescent host, and may be used together with an iridium (Ir)-based dopant.

The structure of the organic light emitting device of the present disclosure may be as illustrated in FIG. 1 and FIG. 2, but is not limited thereto.

FIG. 1 illustrates a structure of the organic light emitting device in which an anode (2), a light emitting layer (3) and a cathode (4) are consecutively laminated on a substrate (1). In such a structure, the heterocyclic compound may be included in the light emitting layer (3).

FIG. 2 illustrates a structure of the organic light emitting device in which an anode (2), a hole injection layer (5), a hole transfer layer (6), a light emitting layer (7), an electron transfer layer (8) and a cathode (4) are consecutively laminated on a substrate (1). In such a structure, the heterocyclic compound may be included in the hole injection layer (5), the hole transfer layer (6), the light emitting layer (7) or the electron transfer layer (8).

For example, the organic light emitting device according to the present disclosure may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

The organic material layer may have a multilayer structure including a hole injection layer, a hole transfer layer, a light emitting layer, an electron transfer layer and the like, however, the structure is not limited thereto, and the organic material layer may have a single layer structure. In addition, the organic material layer may be prepared to have less numbers of layers through a solvent process such as spin coating, dip coating, doctor blading, screen printing, inkjet printing or a thermal transfer method instead of a deposition method using various polymer materials.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

The hole injection material is a material favorably receiving holes from an anode at a low voltage, and the highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer material is a material capable of receiving holes from an anode or a hole injection layer and transferring the holes to a light emitting layer, and materials having high mobility for the holes are suited. Specific examples thereof include arylamine-based organic materials, conductive polymers, block copolymers having conjugated parts and non-conjugated parts together, and the like, but are not limited thereto, and the hole transfer material may be formed into one or more layers.

The light emitting layer may emit light of red, green or blue, and may be formed with phosphorescent materials or fluorescent materials. The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes (Alq$_3$); carbazole-based compounds; dimerized styryl compounds; BAlq; 10-hydroxybenzo quinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

The host material of the light emitting layer includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto.

The iridium-based complex used as a dopant of the light emitting layer is as follows, but is not limited thereto.

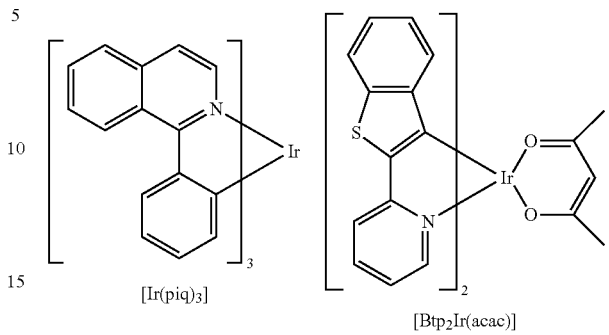

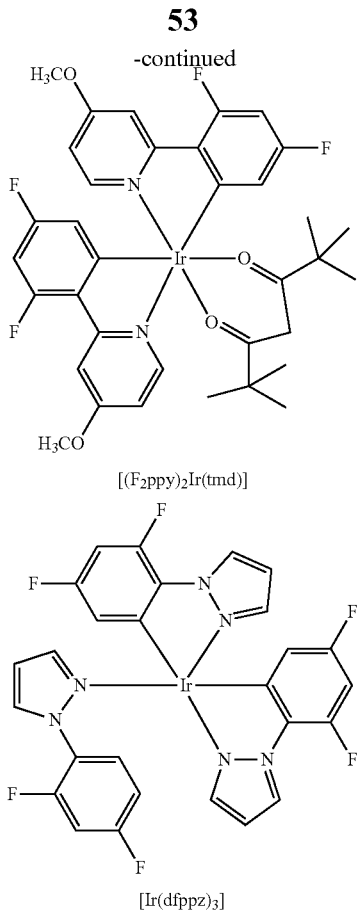

[(F₂ppy)₂Ir(tmd)]

[Ir(dfppz)₃]

The electron transfer material is a material favorably receiving electrons from a cathode and transferring the electrons to a light emitting layer, materials having high mobility for the electrons are suited. Specific examples thereof include Al complexes of 8-hydroxyquinoline; complexes including Alq₃; organic radical compounds; hydroxy-flavon-metal complexes, and the like, but are not limited thereto.

The organic light emitting device according to the present disclosure may be a top-emission type, a bottom-emission type or a dual-emission type depending on the materials used.

SYNTHESIS EXAMPLE

Synthesis Example 1. Synthesis of Compound 1

1) Synthesis of 2,2'-dimethoxy-3,3'-dinitro-1,1'-biphenyl

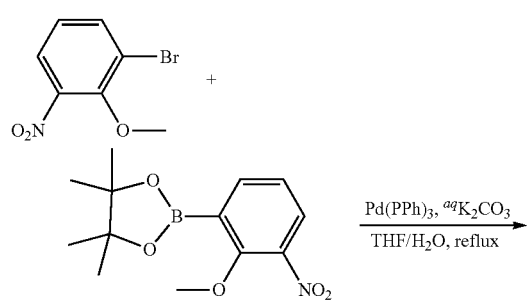

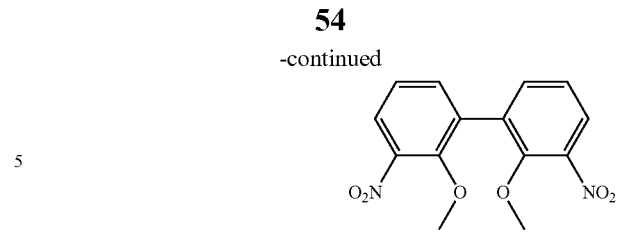

Compound 1-1

After completely dissolving 1-bromo-2-methoxy-3-nitrobenzene (0.43 mol, 100.0 g) in tetrahydrofuran (THF, 1 L), 2-(2-methoxy-3-nitrophenyl)-4,4,5,5-tetramethyl-1,3,2-dioxaborolane (0.45 mol, 126 g), a 2 M potassium carbonate solution (200 mL) and tetrakis(triphenylphosphine)palladium(0) (0.021 mol, 25 g) were added thereto, and the result was refluxed for 15 hours. After the reaction was finished, the result was cooled to room temperature, concentrated and went through column chromatography (hexane:ethyl acetate=Hex:EA=20:1) to obtain Compound 1-1 (104.7 g, 80%). MS [M]=304

2) Synthesis of 2,2'-dimethoxy-[1,1'-biphenyl]-3,3'-diamine

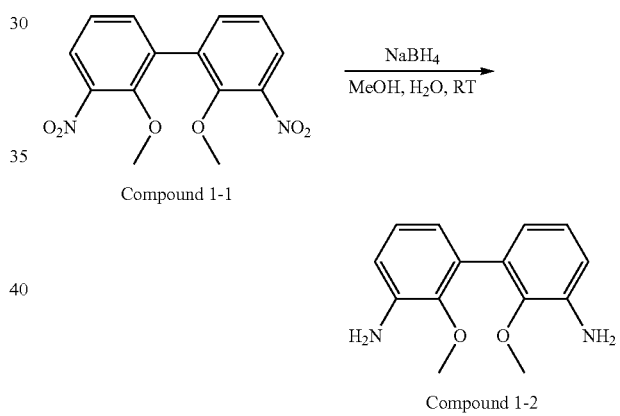

Compound 1-2

After dissolving Compound 1-1 (0.3 mol, 91.0 g) in MeOH/H₂O (1 L), NaBH₄ (4 g) was slowly added thereto. The result was stirred for 5 hours at room temperature, and went through column chromatography (Hex:EA=10:1) to obtain Compound 1-2 (51.3 g, 70%). MS [M]=244

3) Synthesis of Compound 1-3

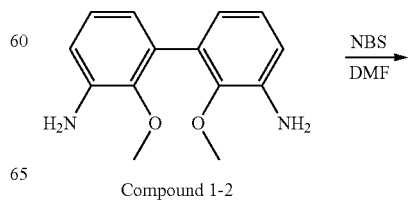

Compound 1-2

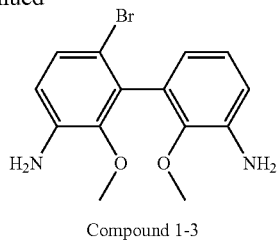

Compound 1-3

After dissolving Compound 1-2 (0.2 mol, 49.0 g) in dimethylformamide (DMF, 0.5 L, 0° C.), N-bromosuccinimide (NBS) (0.2 mol, 35.6 g) slowly dissolved in DMF (0.1 L) was slowly added thereto. After stirring the result for 2 hours at room temperature, H$_2$O was added dropwise thereto to solidify, and the result was filtered. The solids were dissolved in ethyl acetate (EA), then treated with an aqueous Na$_2$S$_2$O$_4$ solution, and the result was treated with MgSO$_4$ to remove water, concentrated, and went through column chromatography (Hex:EA=10:1) to obtain Compound 1-3 (58.1 g, 90%). MS [M]=323.19

4) Synthesis of 3,3'-diamino-6-bromo-[1,1'-biphenyl]-2,2'-diol

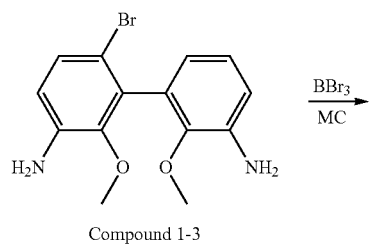

Compound 1-3

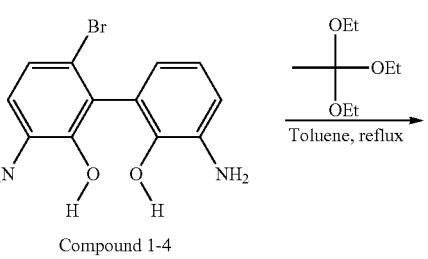

Compound 1-4

After dissolving Compound 1-3 (0.5 mol, 161.6 g) in methylene chloride (MC, 1 L, 0° C.), BBr$_3$ (0.6 mol, 37 mL) was slowly added thereto. After stirring the result for 1 hour at room temperature, H$_2$O was added dropwise thereto to terminate the reaction, and the result was concentrated and went through column chromatography (Hex:EA=3:1) to obtain Compound 1-4 (113 g, 77%). MS [M]=295

5) Synthesis of Compound 1-5

Compound 1-5

After dissolving Compound 1-4 (0.4 mol, 118 g) in toluene (0.5 L) and adding triethyl orthoacetate (0.4 mol, 73 mL) thereto, the result was reacted under reflux for 12 hours in a dean-stock reactor. After the reaction was terminated, the result was concentrated and went through column chromatography (Hex:EA=10:1) to obtain Compound 1-5 (76.9 g, 56%). MS [M]=343

6) Synthesis of 2',10'-dimethylspiro[fluorene-9,6'-fluoreno[3,4-d:6,5-d']bis(oxazole)]

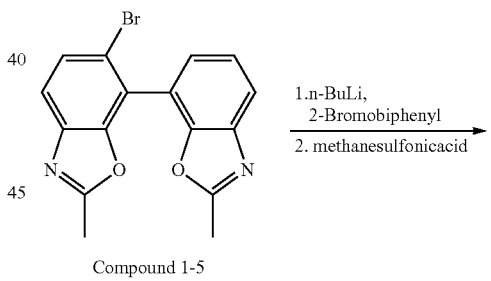

Compound 1-5

Compound 1-6

After dissolving Compound 1-5 (0.3 mol, 103 g) in tetrahydrofuran (THF, 0.5 L) under N$_2$ and lowering the temperature to −78° C., 1 M n-BuLi (0.3 L) was slowly added dropwise thereto. Fluorenone (0.31 mol, 55.8 g) was introduced to the reactor, and the temperature was raised to room temperature. The reaction was terminated with H₂O, and after removing water with MgSO₄ and concentrating the result, methanesulfonic acid (0.5 L) was introduced thereto, the temperature was raised to 80° C., and the reaction was progressed for 1 hour. After slowly introducing the reactant to H₂O (2 L), the result was stirred for 0.5 hours, and solids were filtered. The produced solids went through column chromatography (Hex:EA=10:1) to obtain Compound 1-6 (86 g, 62%). MS [M]=462

7) Synthesis of 4',8'-dibromo-2',10'-dimethylspiro [fluorene-9,6'-fluoreno[3,4-d:6,5-d']bis(oxazole)]

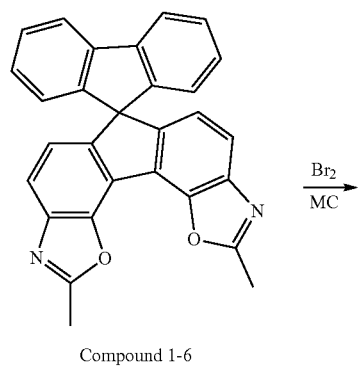

Compound 1-6

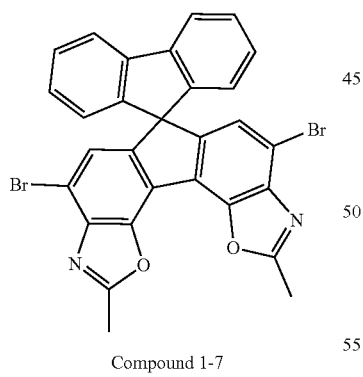

Compound 1-7

After dissolving Compound 1-6 (0.2 mol, 46.2 g) in methylene chloride (MC, 0.5 L, 0° C.) and lowering the temperature to 0° C., Br₂ (0.4 mol, 20.5 mL) was slowly added thereto, and the temperature was raised to room temperature. The reaction solution was treated with an aqueous Na₂S₂O₄ solution, then treated with MgSO₄ to remove water, concentrated and went through column chromatography (Hex:EA=10:1) to obtain Compound 1-7 (99.3 g, 85%). MS [M]=584

8) Synthesis of Compound 1

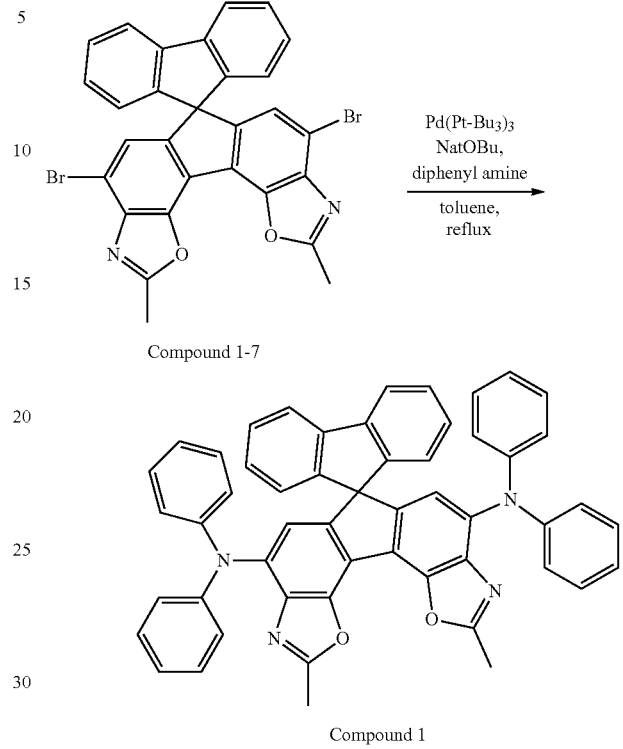

After dissolving Compound 1-7 (0.01 mol, 5.8 g), diphenylamine (0.025 mol, 4.23 g) and NaOtBu (0.03 mol, 2.9 g) in toluene (50 mL), the result was refluxed, and bis[tri-tert-butylphosphine]palladium (0.0001 mol, 0.05 g) was slowly added dropwise thereto. After the reaction was terminated, the result was treated with H₂O to remove NaOtBu, treated with MgSO₄ to remove water, and concentrated, and then went through column chromatography (Hex:EA=7:1) to obtain Compound 1 (5.32 g, 70%). MS [M]=761

Synthesis Example 2. Synthesis of Compound 2

Synthesis of N4,N8-di([1,1'-biphenyl]-4-yl)-N4,N8-bis(4-(tert-butyl)phenyl)-2,10-dimethyl-6,6-diphenyl-6H-fluoreno[3,4-d:6,5-d']bis(oxazole)-4,8-diamine

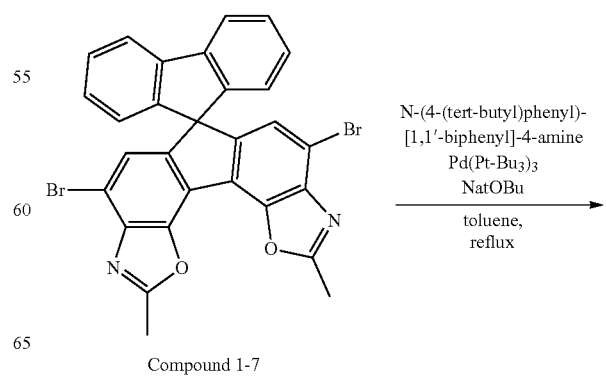

Compound 1-7

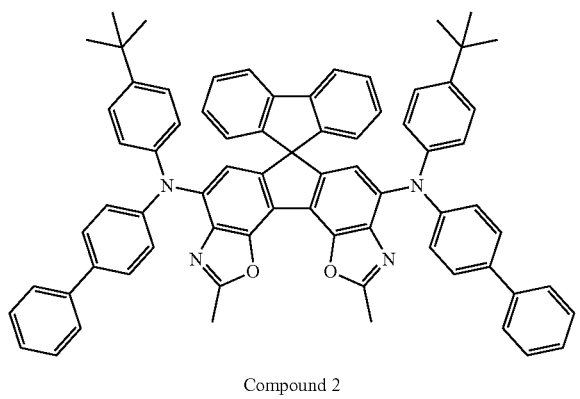

Compound 2

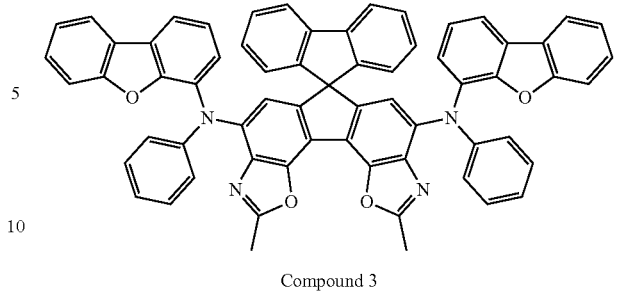

Compound 3

After dissolving Compound 1-7 (0.01 mol, 5.8 g), N-(4-(tert-butyl)phenyl)-[1,1'-biphenyl]-4-amine (0.025 mol, 7.54 g) and NaOtBu (0.03 mol, 2.9 g) in toluene (50 mL), the result was refluxed, and bis[tri-tert-butylphosphine]palladium (0.0001 mol, 0.05 g) was slowly added dropwise thereto. After the reaction was terminated, the result was treated with H₂O to remove NaOtBu, treated with MgSO₄ to remove water, and concentrated, and then went through column chromatography (Hex:EA=6:1) to obtain Compound 2 (5.02 g, 49%). MS [M]=1027

1H NMR data of Compound 2: δ=1.30 (s, 18H), 2.64 (s, 6H), 7.06-7.24 (m, 18H), 7.30-7.40 (m, 6H), 7.44 (t, 2H), 7.49-7.56 (m, 8H), 7.74 (d, 4H)

The 1H NMR spectrum was recorded with a Varian Mercury NMR 300 MHz spectrometer using deuterated chloroform purchased from Cambridge Isotope Laboratories, Inc.

After dissolving Compound 1-7 (0.01 mol, 5.8 g), N-phenyldibenzo[b,d]furan-4-amine (0.025 mol, 6.5 g) and NaOtBu (0.03 mol, 2.9 g) in toluene (50 mL), the result was refluxed, and bis[tri-tert-butylphosphine]palladium (0.0001 mol, 0.05 g) was slowly added dropwise thereto. After the reaction was terminated, the result was treated with H₂O to remove NaOtBu, treated with MgSO₄ to remove water, and concentrated, and then went through column chromatography (Hex:EA=6:1) to obtain Compound 3 (4.22 g, 45%). MS [M]=943

1H NMR data of Compound 3: δ=2.58 (s, 6H), 6.94-7.10 (m, 12H), 7.18-7.30 (m, 12H), 7.34-7.40 (m, 6H), 7.50-7.66 (m, 4H), 7.92 (d, 2H)

The 1H NMR spectrum was recorded with a Varian Mercury NMR 300 MHz spectrometer using deuterated chloroform purchased from Cambridge Isotope Laboratories, Inc.

Synthesis Example 4. Synthesis of Compound 4

Synthesis of 2,10-dimethyl-N4,N8,6,6-tetraphenyl-N4,N8-di-o-tolyl-6H-fluoreno[3,4-d:6,5-d']bis(oxazole)-4,8-diamine Synthesis Example 3. Synthesis of Compound 3

Synthesis of N4,N8-bis(dibenzo[b,d]furan-4-yl)-2,10-dimethyl-N4,N8,6,6-tetraphenyl-6H-fluoreno[3,4-d:6,5-d']bis(oxazole)-4,8-diamine

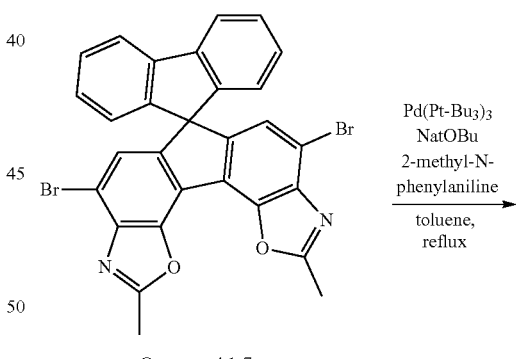

Compound 1-7

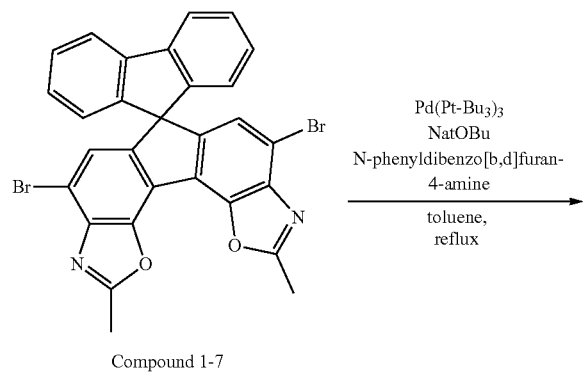

Compound 1-7

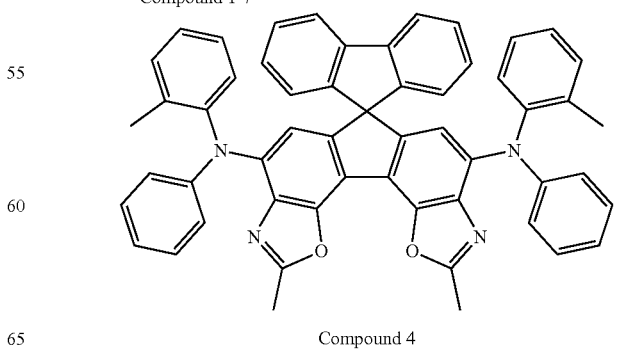

Compound 4

Compound 4 was synthesized in the same manner as in Synthesis Example 3 except that 2-methyl-N-phenylaniline was used instead of N-phenyldibenzo[b,d]furan-4-amine.

EXAMPLE

Example 1

A glass substrate (corning 7059 glass) on which indium tin oxide (ITO) was coated as a thin film to a thickness of 1,000 Å was placed in dispersant-dissolved distilled water and ultrasonic cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol in this order, and dried.

On the transparent ITO electrode prepared as above, a hole injection layer was formed by thermal vacuum depositing the following Compound HAT to a thickness of 50 Å. The following Compound HT-A (1000 Å) was vacuum deposited thereon as a hole transfer layer, and subsequently, the following Compound HT-B (100 Å) was deposited. As a light emitting layer, BH-1 as a host and BD-1 as a dopant in 2% by weight were vacuum deposited to a thickness of 200 Å.

Then, the following Compound ET-A and the following Compound Liq were deposited in a ratio of 1:1 to 300 Å, and thereon, a cathode was formed by consecutively depositing 10% by weight of silver (Ag)-doped magnesium (Mg) having a thickness of 150 Å and aluminum having a thickness of 1,000 Å to manufacture an organic light emitting device.

In the above-mentioned process, the deposition rates of the organic materials were maintained at 1 Å/sec, and the deposition rates of the LiF and the aluminum were maintained at 0.2 Å/sec, and 3 Å/sec to 7 Å/sec, respectively.

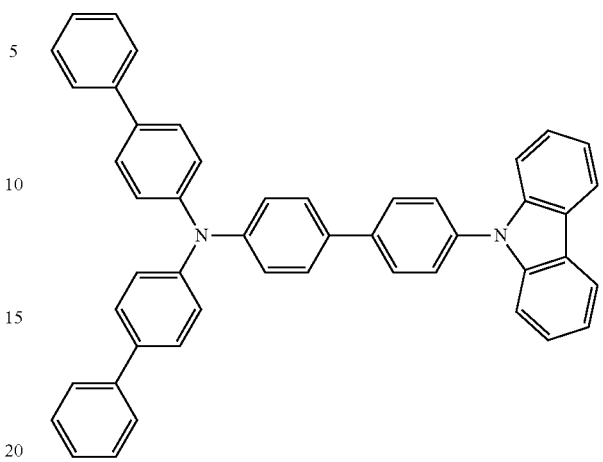
HT-B

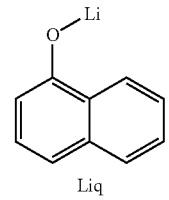
Liq

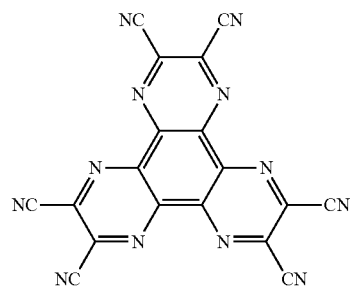
HAT

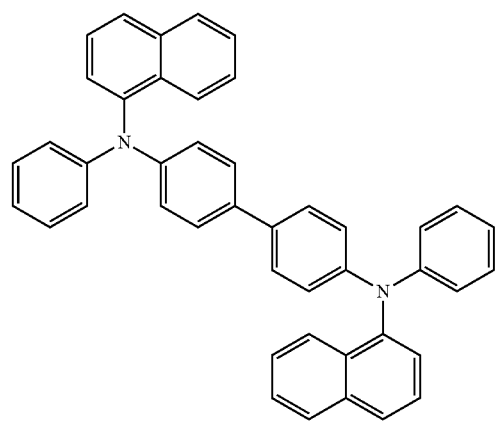
HT-A

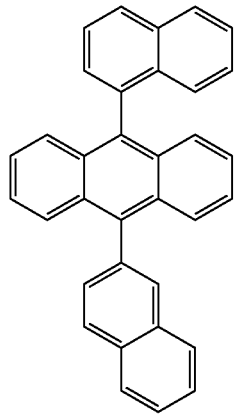
BH-1

BH-2

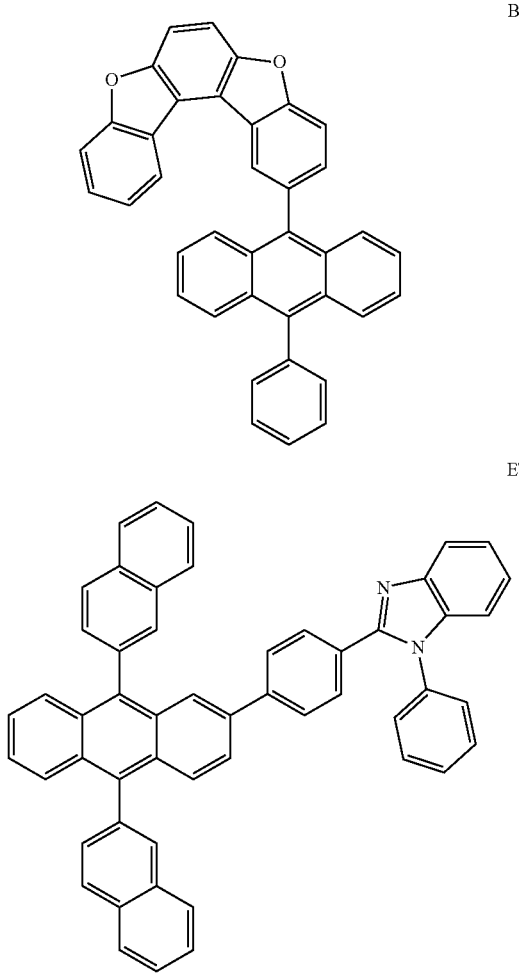

ET-A

BD-1

BD-2

BD-3

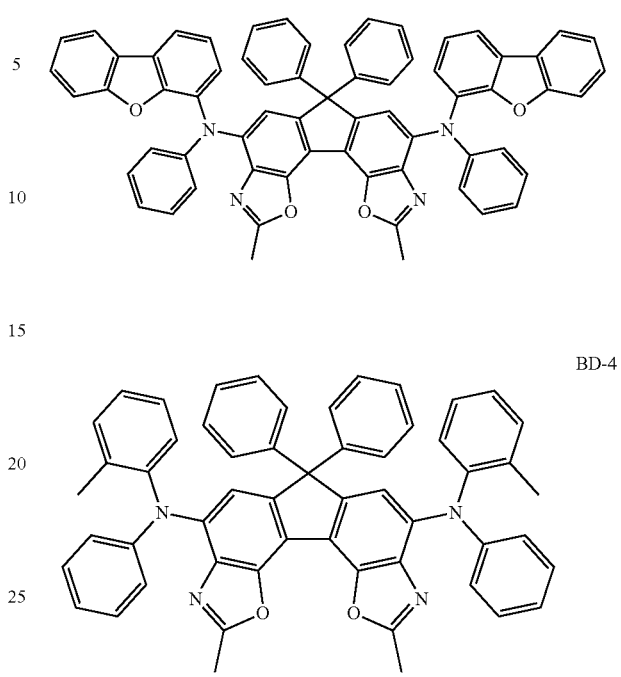

BD-4

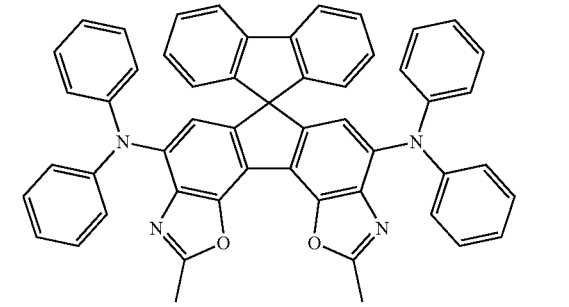

Example 2

An organic light emitting device was manufactured in the same manner as in Example 1 except that Compound BD-2 was used instead of Compound BD-1.

Example 3

An organic light emitting device was manufactured in the same manner as in Example 1 except that Compound BD-3 was used instead of Compound BD-1.

Example 4

An organic light emitting device was manufactured in the same manner as in Example 1 except that Compound BD-4 was used instead of Compound BD-1.

Example 5

An organic light emitting device was manufactured in the same manner as in Example 1 except that Compound BH-2 was further included (weight ratio of BH-1 and BH-2: 1:1).

COMPARATIVE EXAMPLE

Comparative Example 1

An organic light emitting device was manufactured in the same manner as in Example 1 except that the following Compound D-1 was used instead of Compound BD-1.

[D-1]

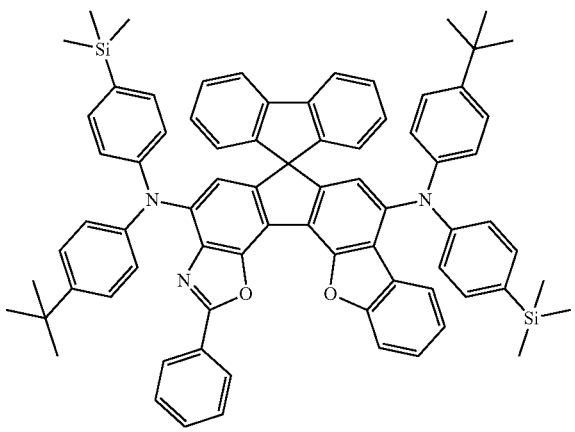

Comparative Example 2

An organic light emitting device was manufactured in the same manner as in Example 1 except that the following Compound D-2 was used instead of Compound BD-1.

[D-2]

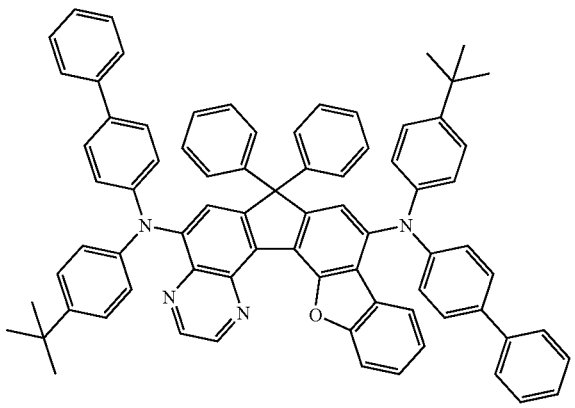

Comparative Example 3

An organic light emitting device was manufactured in the same manner as in Example 1 except that the following Compound D-3 was used instead of Compound BD-1.

[D-3]

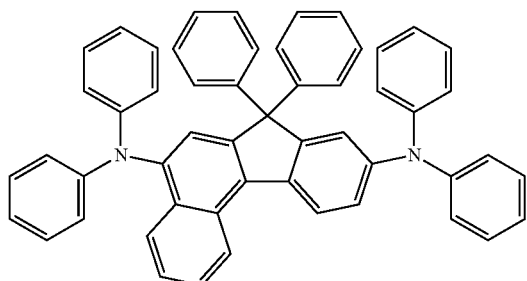

Comparative Example 4

An organic light emitting device was manufactured in the same manner as in Example 1 except that the following Compound D-4 was used instead of Compound BD-1.

[D-4]

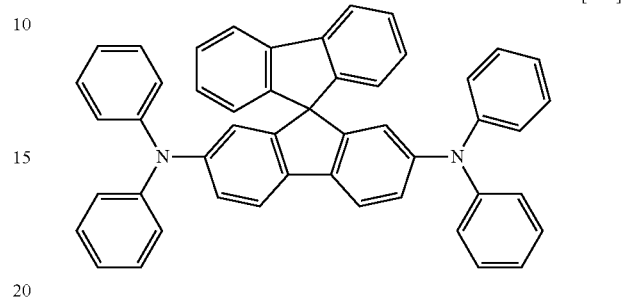

For the organic light emitting devices of Examples 1 to 5 and Comparative Examples 1 to 4, driving voltage, light emission efficiency and color coordinate were measured at current density of 10 mA/cm$^2$, and time (LT95) taken for the luminance becoming 95% from its initial luminance was measured at current density of 20 mA/cm$^2$. The results are shown in the following Table 1.

TABLE 1

| Example | Host | Dopant | 10 mA/cm$^2$ | | | LT95 at 20 mA/cm$^2$ Lifetime (hr) |
| | | | Driving Voltage (v) | Efficiency (cd/A) | CIEy | |
|---|---|---|---|---|---|---|
| Example 1 | BH-1 | BD-1 | 4.4 | 6.0 | 0.092 | 215 |
| Example 2 | BH-1 | BD-2 | 4.6 | 6.1 | 0.093 | 210 |
| Example 3 | BH-1 | BD-3 | 4.5 | 6.2 | 0.096 | 224 |
| Example 4 | BH-1 | BD-4 | 4.5 | 6.2 | 0.096 | 224 |
| Example 5 | BH-1 + BH-2 | BD-1 | 4.6 | 6.3 | 0.093 | 200 |
| Comparative Example 1 | BH-1 | D-1 | 4.3 | 2.9 | 0.097 | 112 |
| Comparative Example 2 | BH-1 | D-2 | 4.6 | 4.8 | 0.094 | 108 |
| Comparative Example 3 | BH-1 | D-3 | 4.3 | 4.2 | 0.097 | 118 |
| Comparative Example 4 | BH-1 | D-4 | 4.6 | 4.8 | 0.094 | 88 |

From Table 1, it was identified that Examples 1 to 5 using the compound of Chemical Formula 1 of the present application had excellent efficiency and lifetime properties compared to Comparative Examples 1 and 2 having different structures fused to the fluorene core structure; Comparative Example 3 using a compound having a benzofluorene core structure; and Comparative Example 4 using a compound having a spirobifluorene core structure.

The invention claimed is:

1. A heterocyclic compound represented by the following Chemical Formula 1:

[Chemical Formula 1]

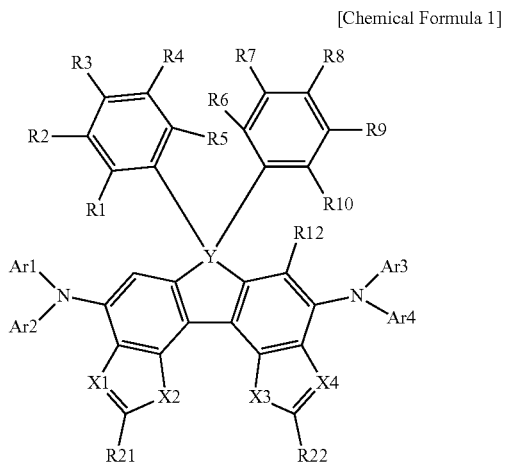

wherein, in Chemical Formula 1,

Y is C,

R11 and R12 are the same as or different from each other, and each independently hydrogen; deuterium; a cyano group; a halogen group; a silyl group; a boron group; a substituted or unsubstituted alkyl group; a substituted or unsubstituted alkoxy group; a substituted or unsubstituted cycloalkyl group; a substituted or unsubstituted aryl group; a substituted or unsubstituted alkylamine group; a substituted or unsubstituted arylamine group; a substituted or unsubstituted heteroarylamine group; or a substituted or unsubstituted heterocyclic group, X1 and X4 are N, X2 and X3 are O, R21 and R22 are the same as or different from each other, and each independently an alkyl group having 1 to 10 carbon atoms; a cycloalkyl group having 3 to 30 carbon atoms; or a phenyl group which is substituted by a cyano group, a halogen group or an alkyl group having 1 to 10 carbon atoms, Ar1 to Ar4 and R1 to R10 are the same as or different from each other, and each independently hydrogen; deuterium; a cyano group; a halogen group; a silyl group; a boron group; a substituted or unsubstituted alkyl group; a substituted or unsubstituted alkoxy group; a substituted or unsubstituted cycloalkyl group; a substituted or unsubstituted aryl group; a substituted or unsubstituted alkylamine group; a substituted or unsubstituted arylamine group; a substituted or unsubstituted heteroarylamine group; or a substituted or unsubstituted heterocyclic group, or adjacent substituents bond to each other to form a substituted or unsubstituted ring.

2. The heterocyclic compound of claim 1, wherein Chemical Formula 1 is represented by the following Chemical Formula 2 or Chemical Formula 3:

[Chemical Formula 2]

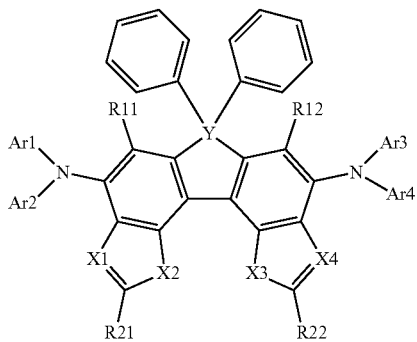

[Chemical Formula 3]

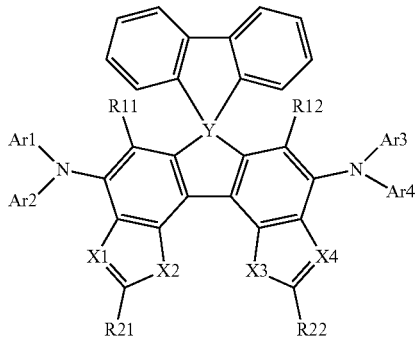

in Chemical Formulae 2 and 3,

Ar1 to Ar4, R11, R12, X1 to X4, Y, R21 and R22 have the same definitions as in Chemical Formula 1.

3. The heterocyclic compound of claim 1, wherein Ar1 to Ar4 are the same as or different from each other, and each independently a substituted or unsubstituted aryl group; or a substituted or unsubstituted heterocyclic group.

4. The heterocyclic compound of claim 1, wherein the compound of Chemical Formula 1 is represented by any one of the following compounds:

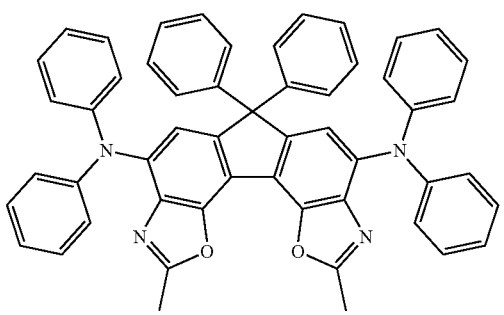

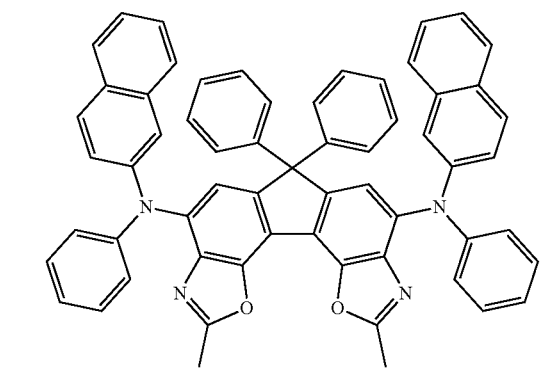
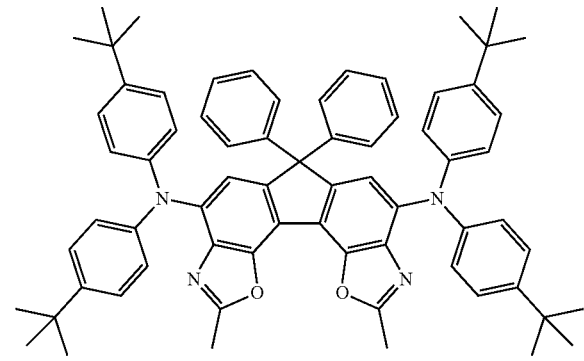
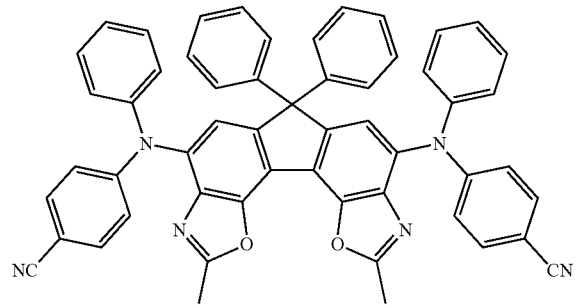
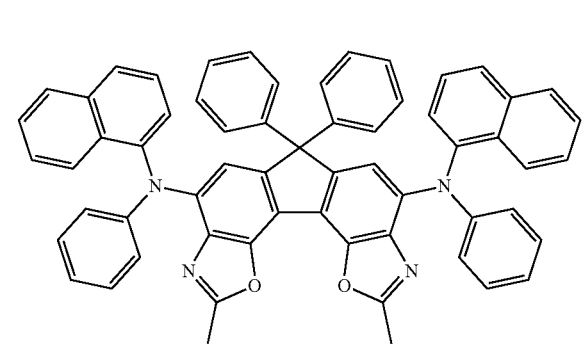
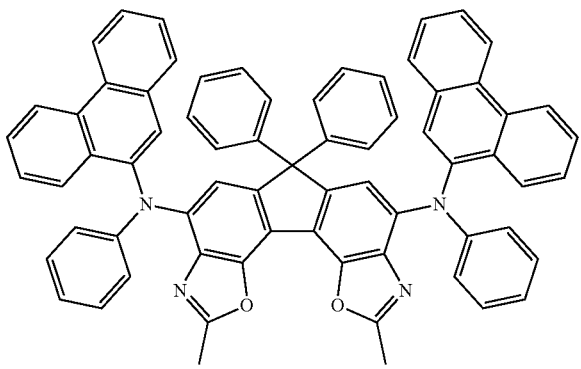
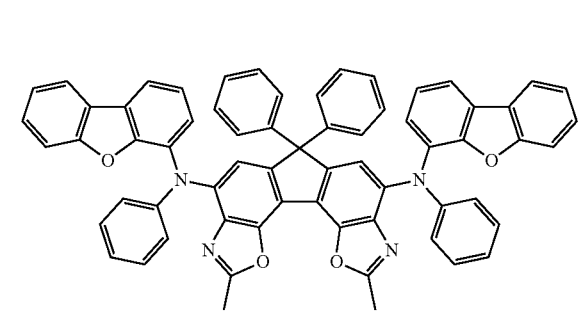
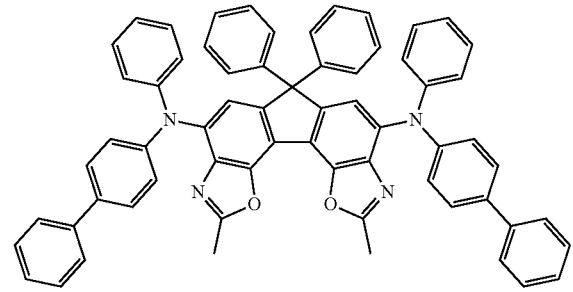
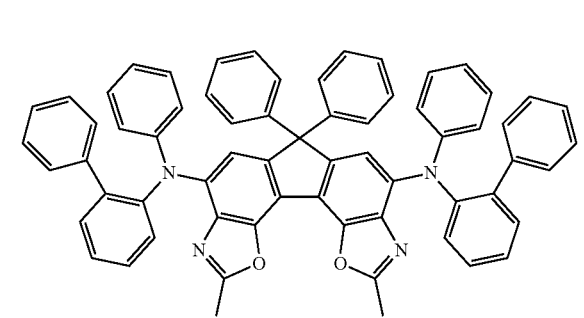
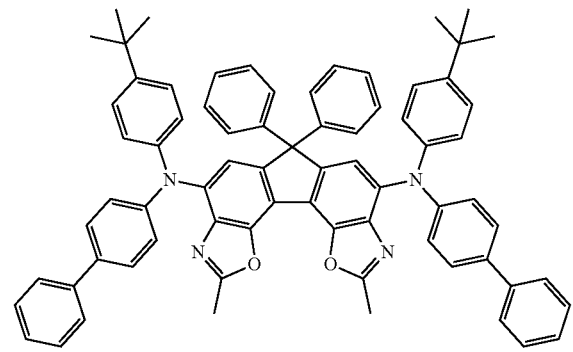
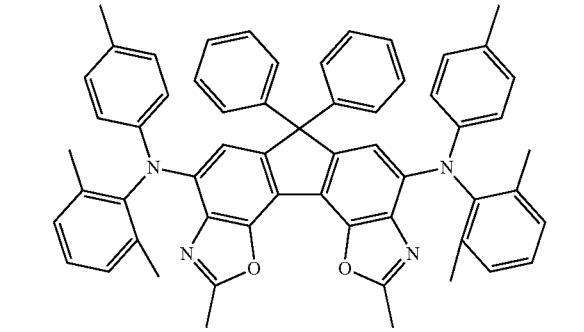

71
-continued
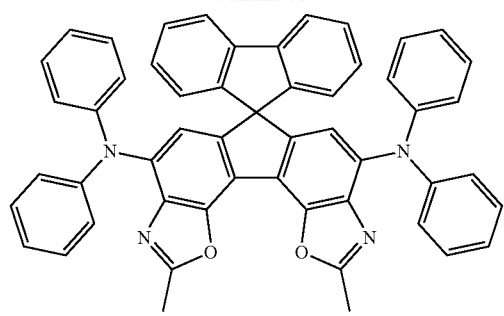
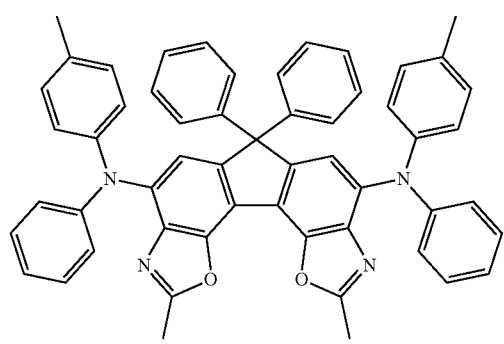
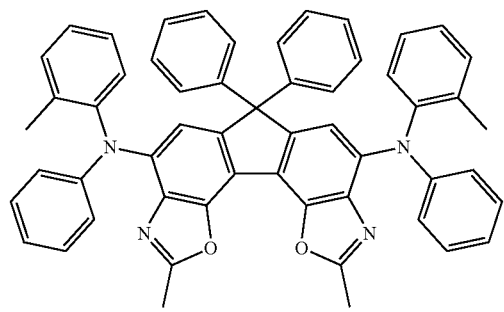
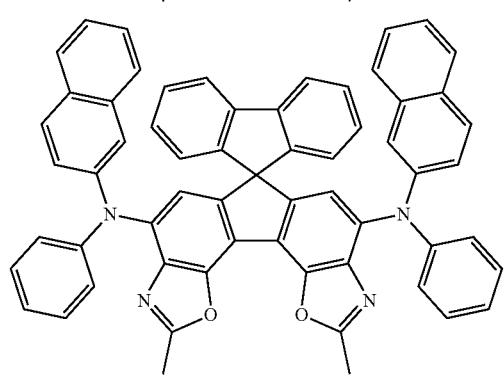
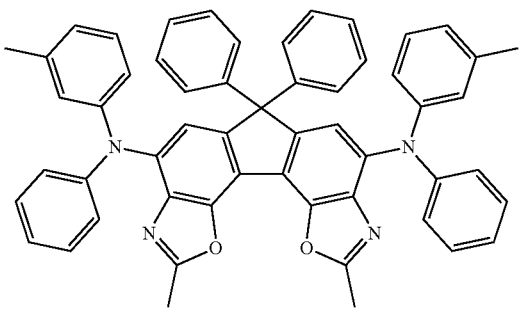
72
-continued
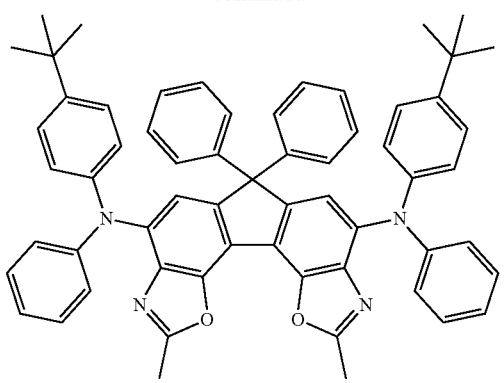 [SMILES: Cc1nc2c(N(c3ccccc3)c3ccc(C(C)(C)C)cc3)cc3c(c2o1)-c1c(cc(N(c2ccccc2)c2ccc(C(C)(C)C)cc2)c2nc(C)oc12)C3(c1ccccc1)c1ccccc1]
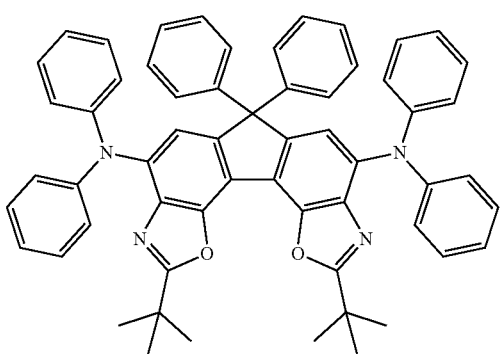
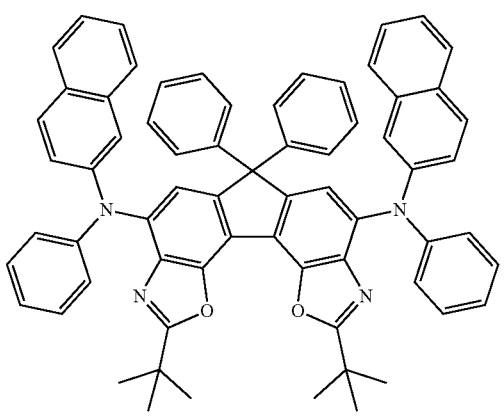

73
-continued
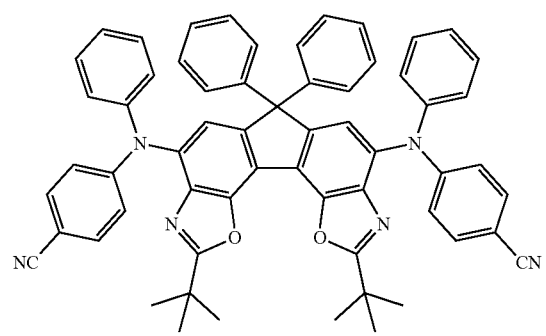
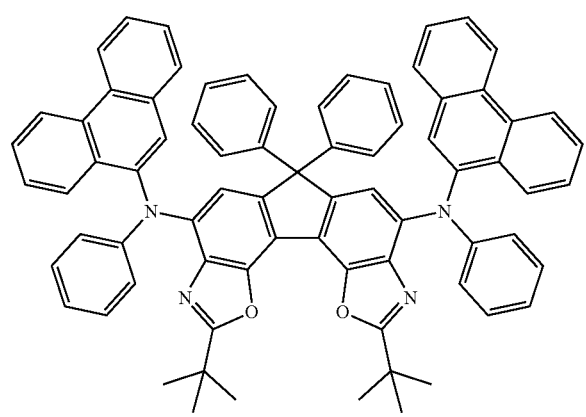
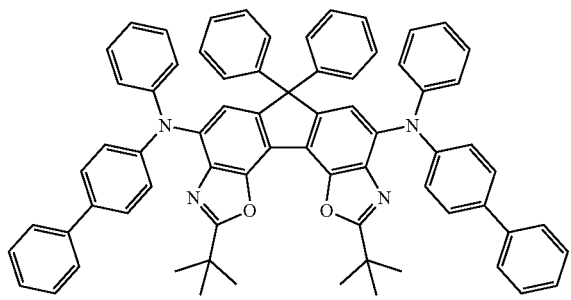
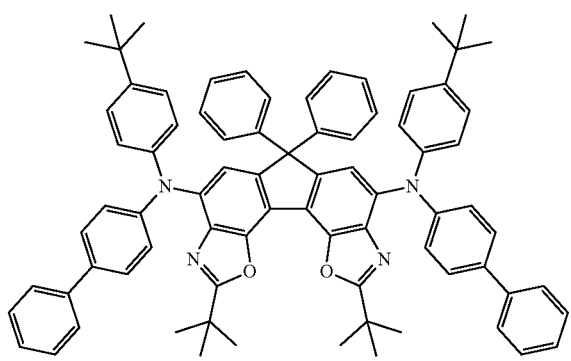
74
-continued
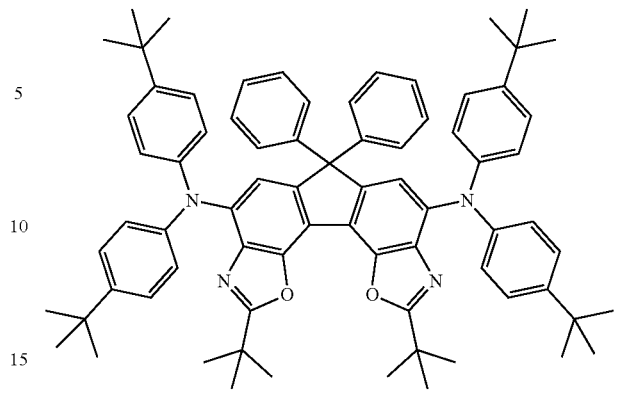
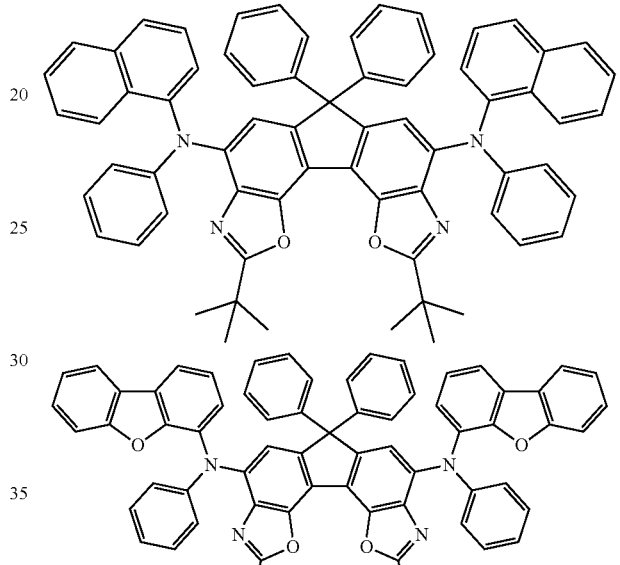
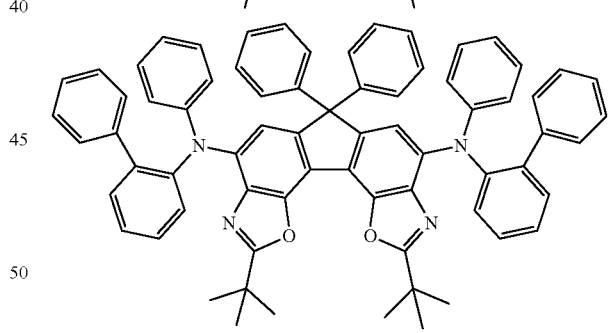
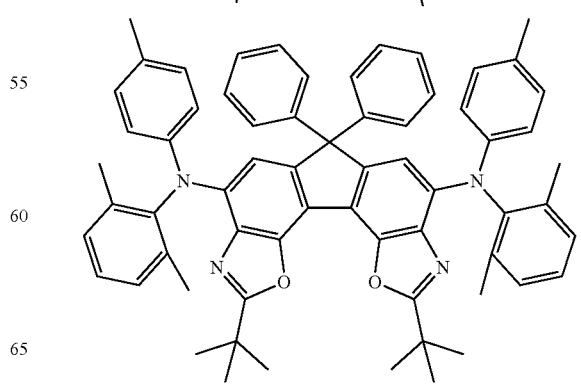

75
-continued
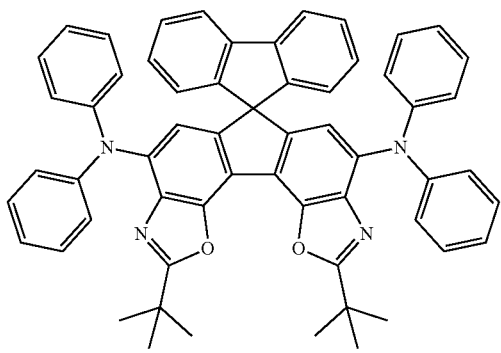
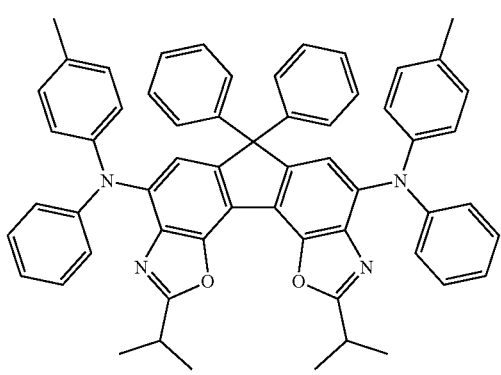
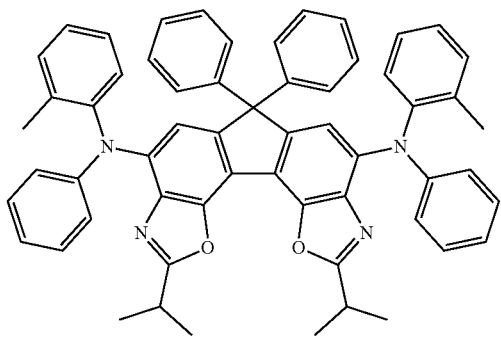
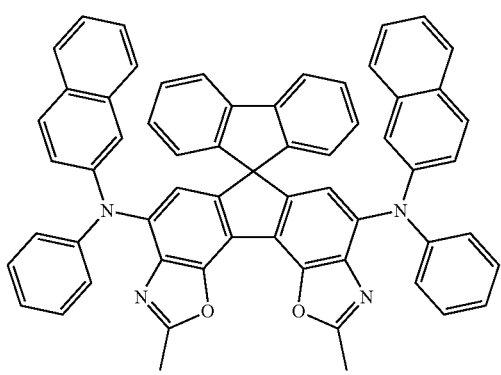
76
-continued
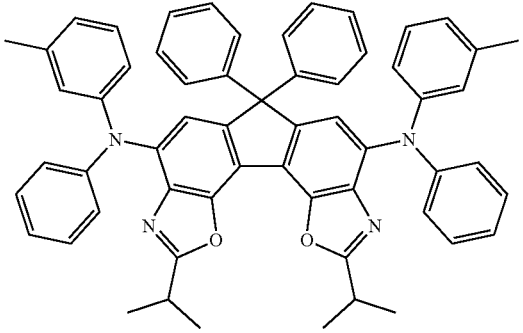
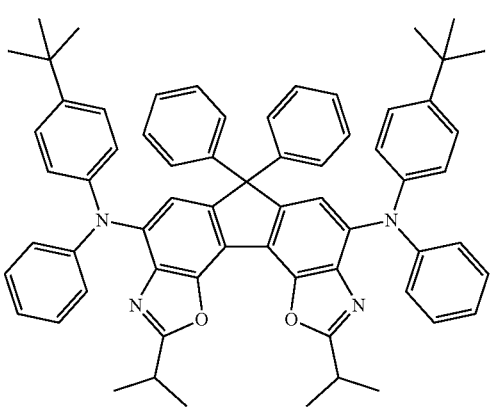
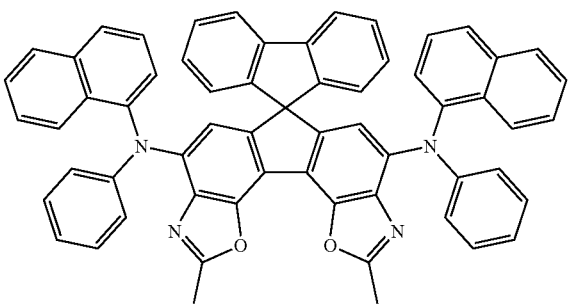 [SMILES: Cc1nc2c(N(c3ccccc3)c3cccc4ccccc34)cc3c(c2o1)-c1c(cc(N(c2ccccc2)c2cccc4ccccc24)c2nc(C)oc12)C31c2ccccc2-c2ccccc21]
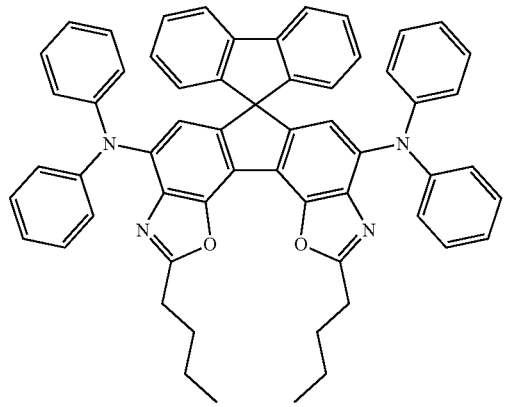

77
-continued
78
-continued
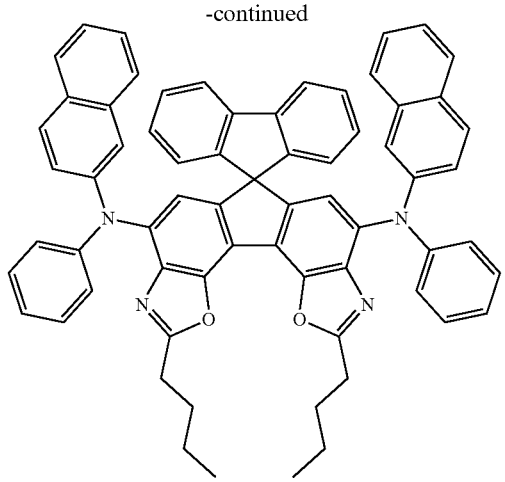
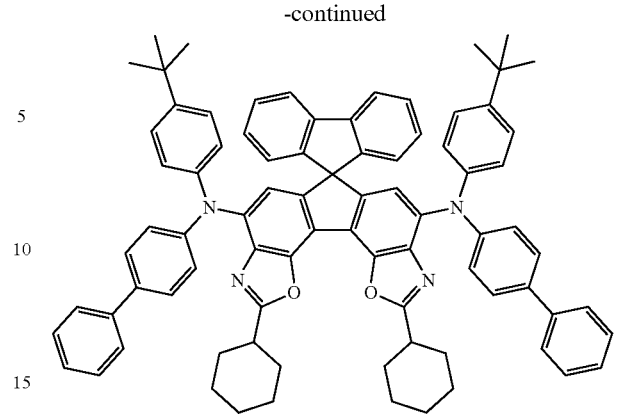
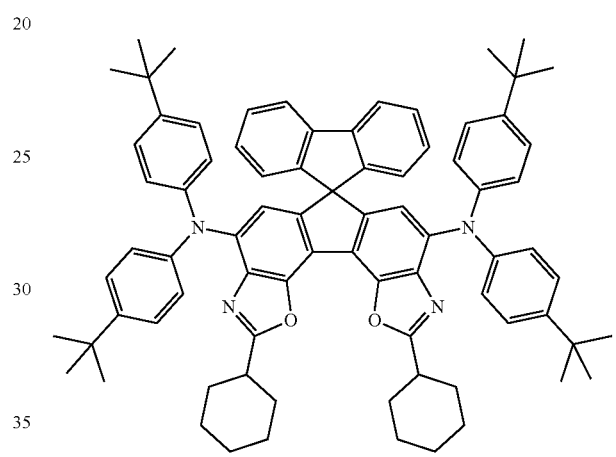
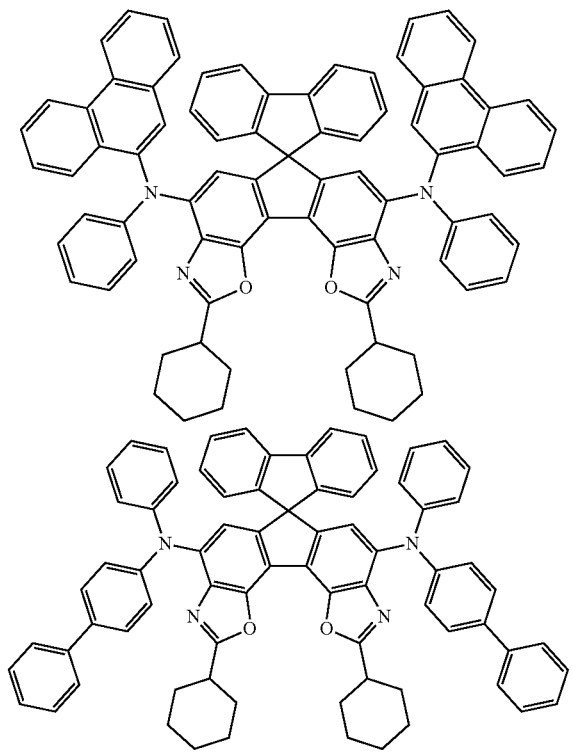
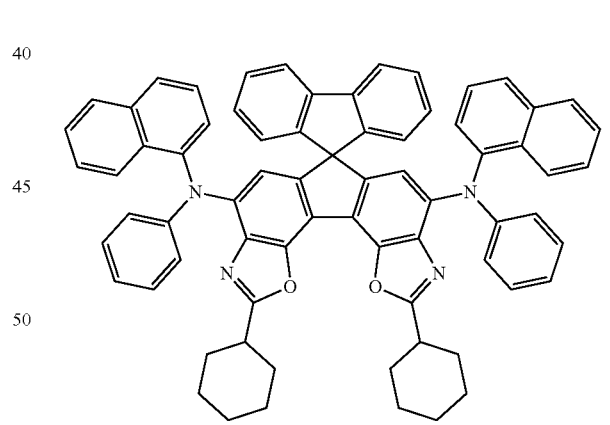
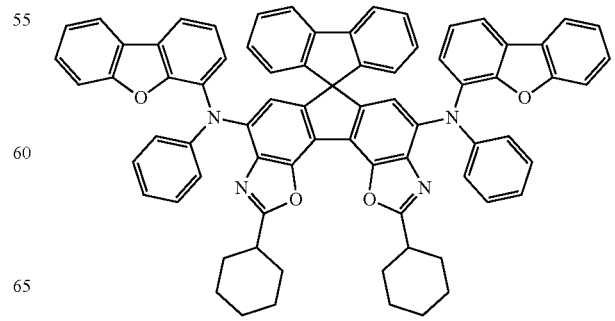

-continued
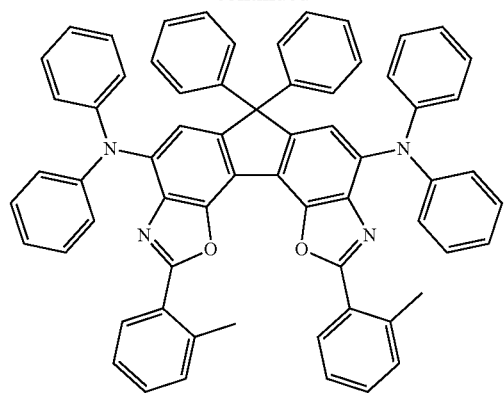 [SMILES: Cc1ccccc1-c1nc2c(N(c3ccccc3)c3ccccc3)cc3c(c2o1)-c1c(cc(N(c2ccccc2)c2ccccc2)c2nc(-c4ccccc4C)oc12)C3(c1ccccc1)c1ccccc1]
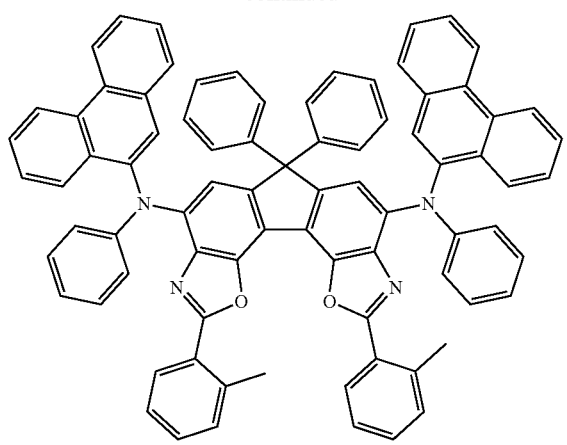
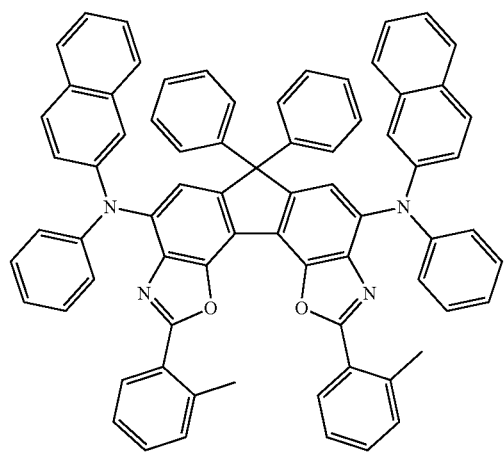 [SMILES: Cc1ccccc1-c1nc2c(N(c3ccccc3)c3ccc4ccccc4c3)cc3c(c2o1)-c1c(cc(N(c2ccccc2)c2ccc4ccccc4c2)c2nc(-c4ccccc4C)oc12)C3(c1ccccc1)c1ccccc1]
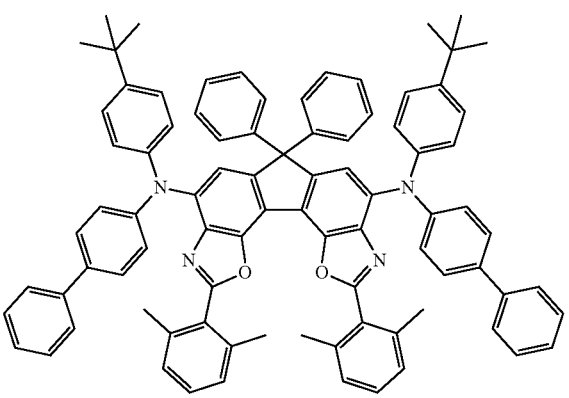
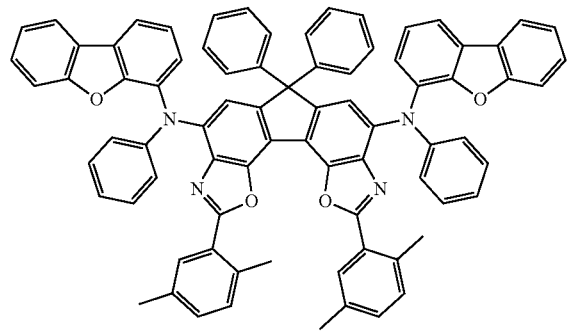
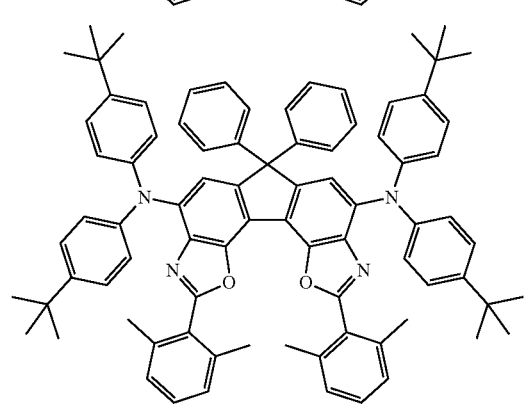

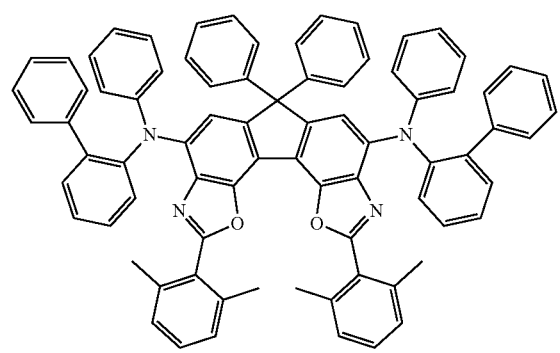
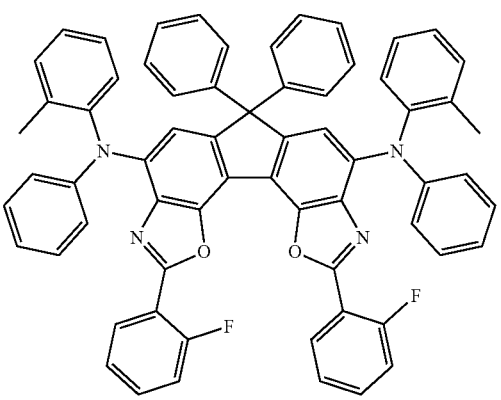
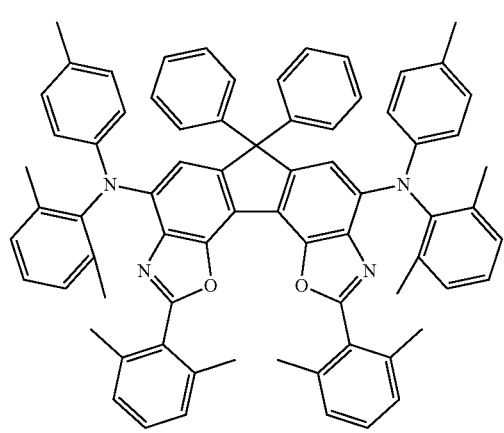
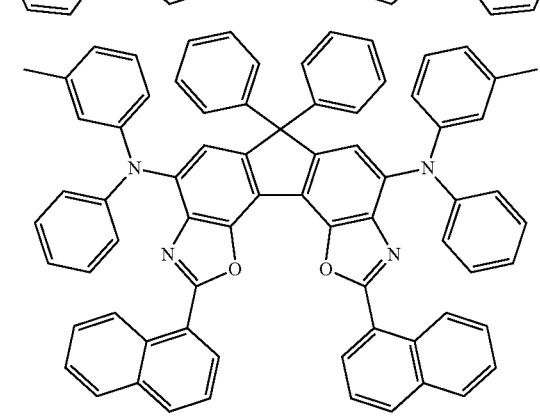
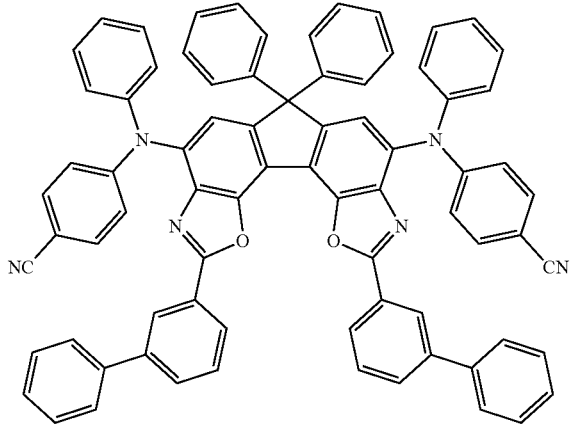
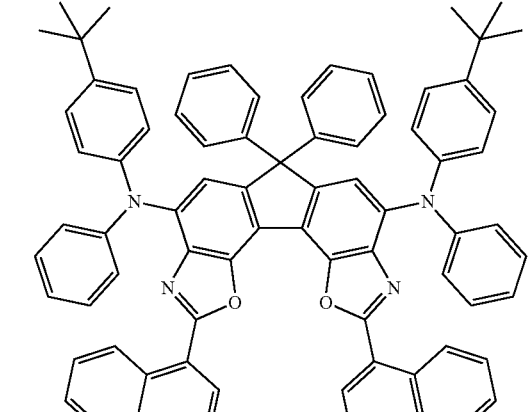
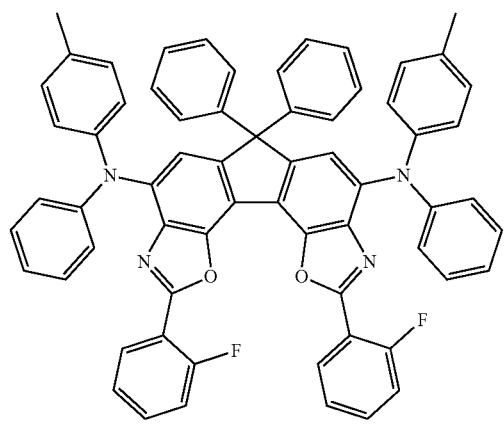

-continued
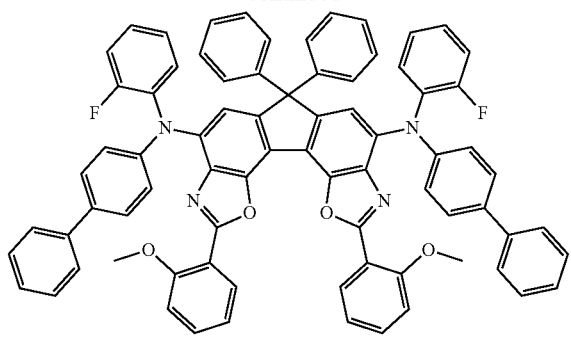
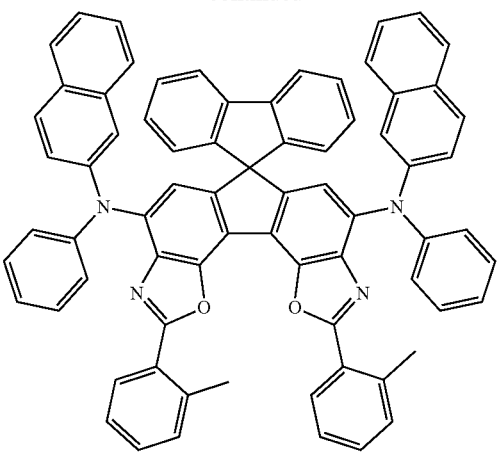
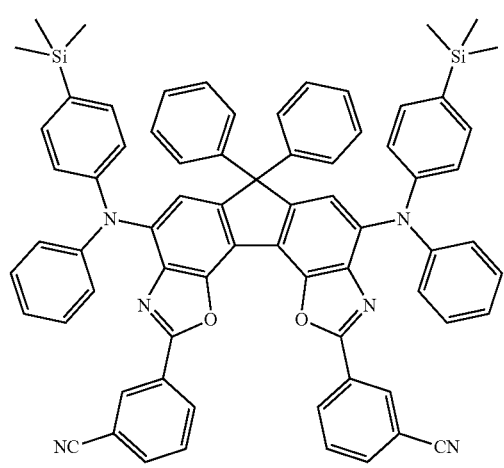
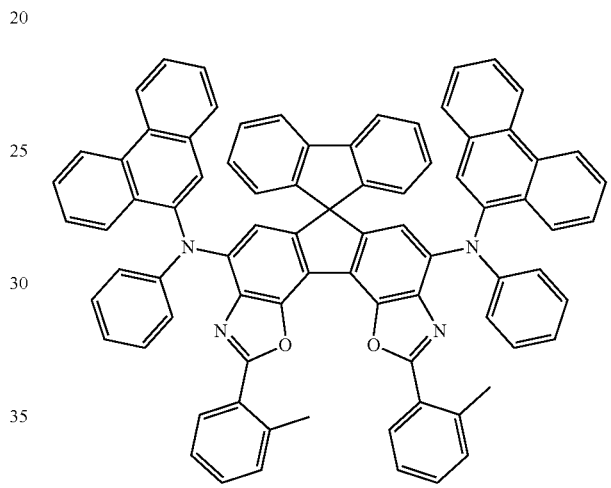
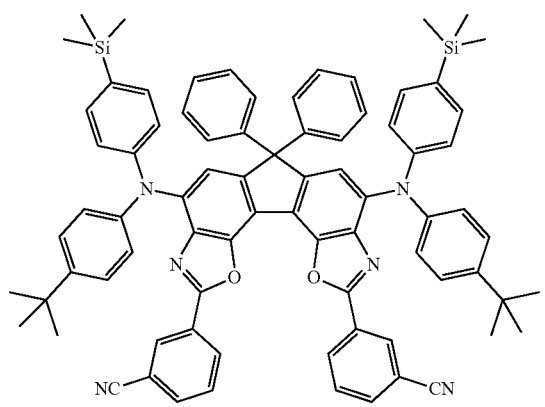
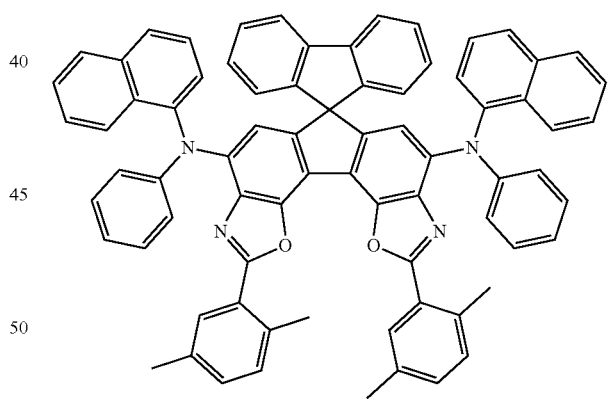
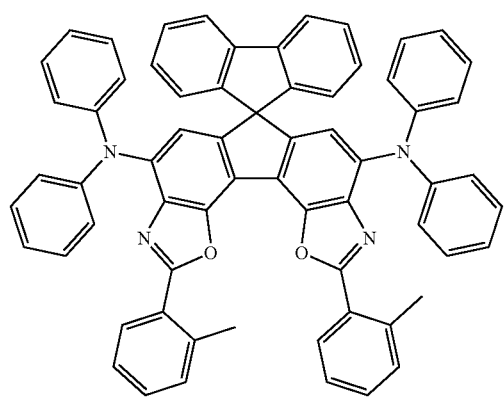
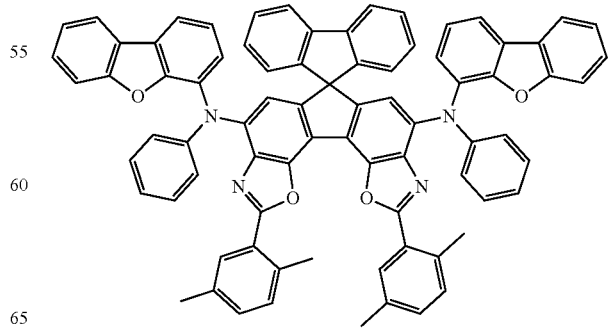

85
-continued
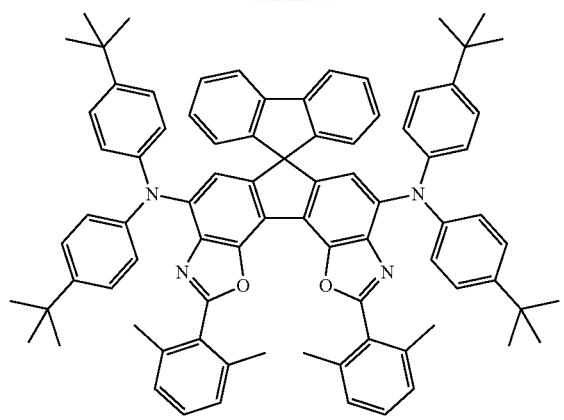
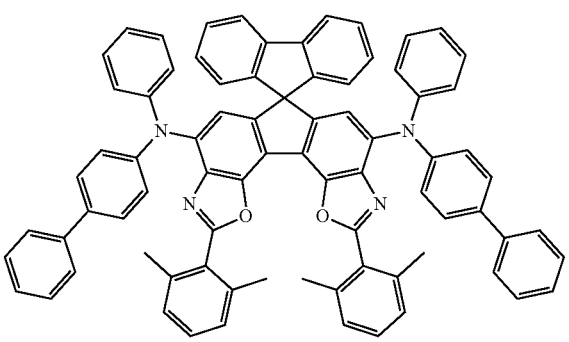
86
-continued
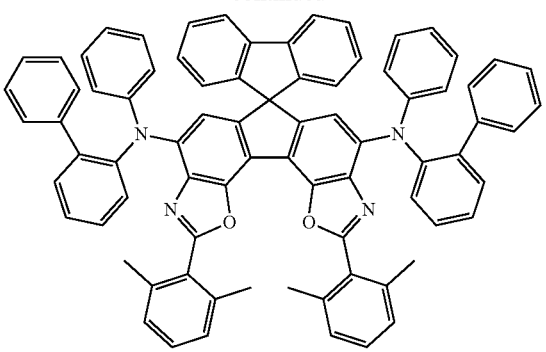
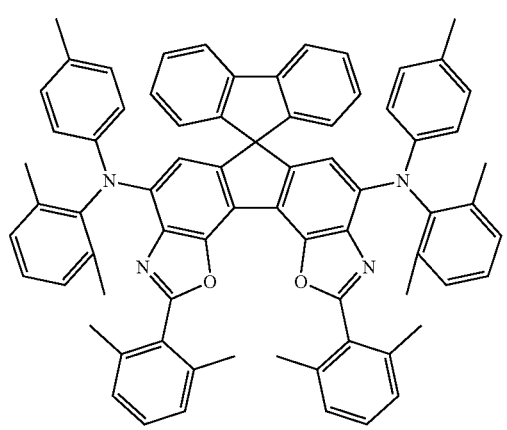
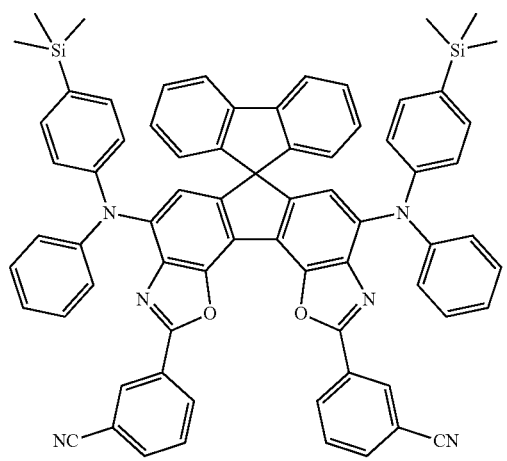
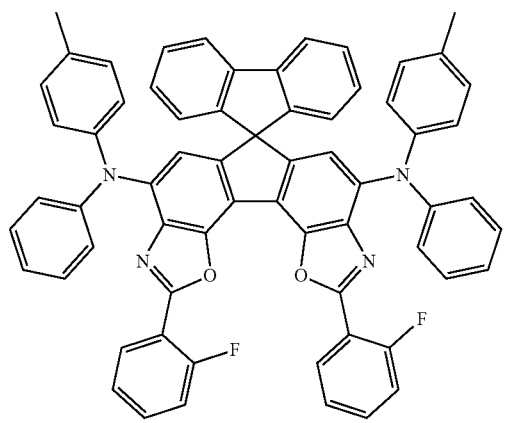

87
-continued

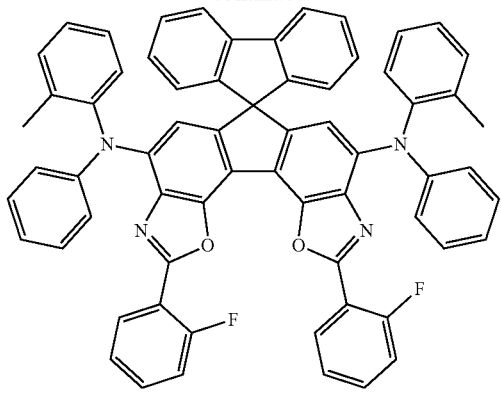 [SMILES: Cc1ccccc1N(c1ccccc1)c1cc2c(c3oc(-c4ccccc4F)nc13)-c1c(cc(N(c3ccccc3)c3ccccc3C)c3nc(-c4ccccc4F)oc13)C2(c1ccccc1)c1ccccc1]

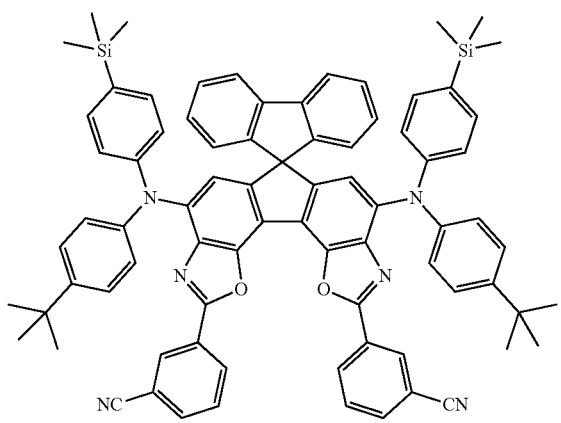

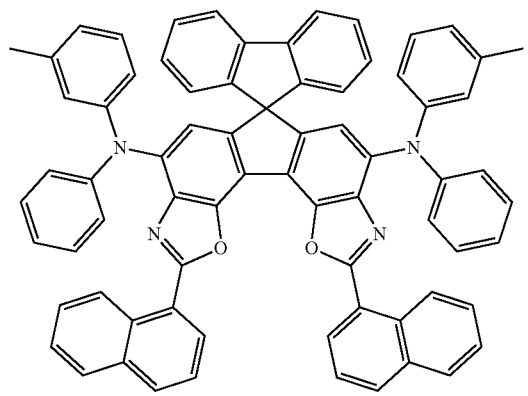

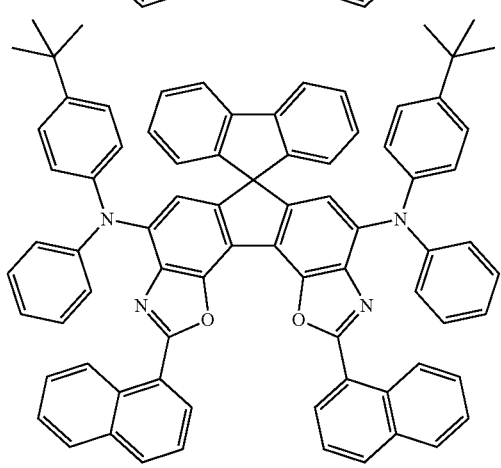

88
-continued

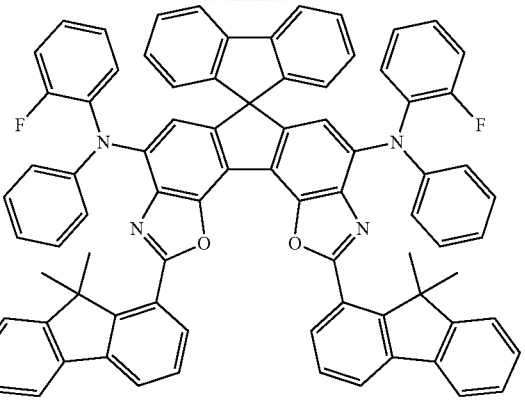

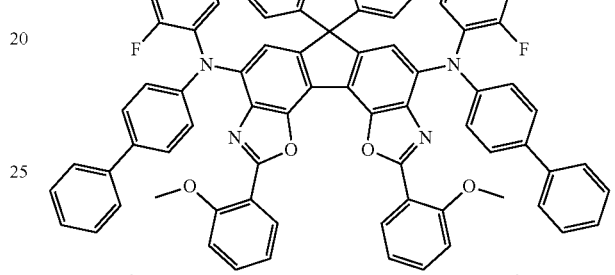

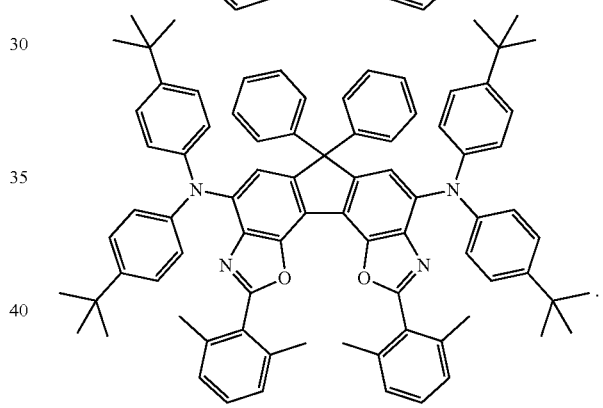

5. An organic light emitting device comprising:
a first electrode;
a second electrode provided to face the first electrode; and
one or more organic material layers provided between the first electrode and the second electrode,
wherein one or more layers of the one or more organic material layers comprise the heterocyclic compound of claim 1.

6. The organic light emitting device of claim 5, wherein the one or more organic material layers comprise a hole injection layer or a hole transfer layer, and the hole injection layer or the hole transfer layer comprises the heterocyclic compound.

7. The organic light emitting device of claim 5, wherein the one or more organic material layers comprise an electron transfer layer or an electron injection layer, and the electron transfer layer or the electron injection layer comprises the heterocyclic compound.

8. The organic light emitting device of claim 5, wherein the one or more organic material layers comprise a light emitting layer, and the light emitting layer comprises the heterocyclic compound.

9. A heterocyclic compound represented by the following Chemical Formula 1-1:

[Chemical Formula 1-1]

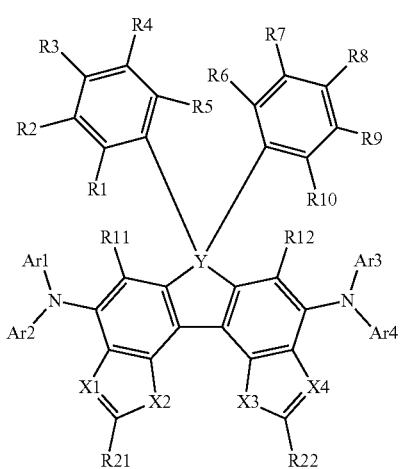

wherein, in Chemical Formula 1-1,

Y is Si,

R11 and R12 are the same as or different from each other, and each independently hydrogen; deuterium; a cyano group; a halogen group; a silyl group; a boron group; a substituted or unsubstituted alkyl group; a substituted or unsubstituted alkoxy group; a substituted or unsubstituted cycloalkyl group; a substituted or unsubstituted aryl group; a substituted or unsubstituted alkylamine group; a substituted or unsubstituted arylamine group; a substituted or unsubstituted heteroarylamine group; or a substituted or unsubstituted heterocyclic group;

X1 and X4 are N;

X2 and X3 are O; and

R21, R22, Ar1 to Ar4 and R1 to R10 are the same as or different from each other, and each independently hydrogen; deuterium; a cyano group; a halogen group; a silyl group; a boron group; a substituted or unsubstituted alkyl group; a substituted or unsubstituted alkoxy group; a substituted or unsubstituted cycloalkyl group; a substituted or unsubstituted aryl group; a substituted or unsubstituted alkylamine group; a substituted or unsubstituted arylamine group; a substituted or unsubstituted heteroarylamine group; or a substituted or unsubstituted heterocyclic group, or adjacent substituents bond to each other to form a substituted or unsubstituted ring.

10. The heterocyclic compound of claim 9, wherein the compound of Chemical Formula 1-1 is represented by the following Chemical Formula 2-1 or Chemical Formula 3-1:

[Chemical Formula 2-1]

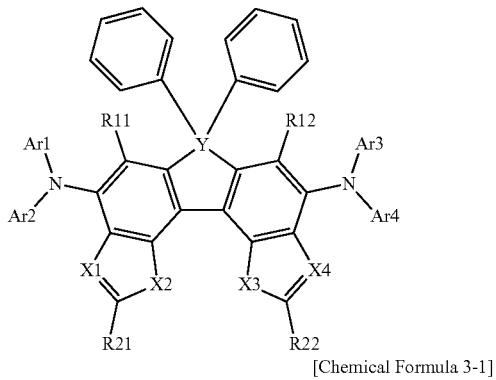

[Chemical Formula 3-1]

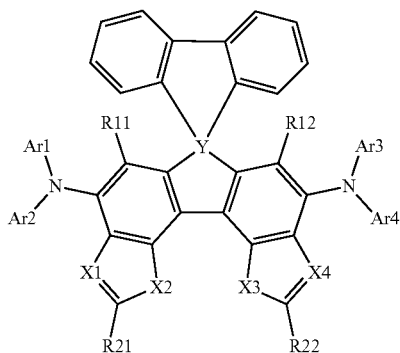

in Chemical Formulae 2-1 and 3-1,

Ar1 to Ar4, R11, R12, X1 to X4, Y, R21 and R22 have the same definitions as in Chemical Formula 1-1.

11. The heterocyclic compound of claim 9, wherein Ar1 to Ar4 are the same as or different from each other, and each independently a substituted or unsubstituted aryl group; or a substituted or unsubstituted heterocyclic group.

12. The heterocyclic compound of claim 9, wherein R21 and R22 are the same as or different from each other, and each independently a substituted or unsubstituted alkyl group having 1 to 10 carbon atoms; a substituted or unsubstituted cycloalkyl group having 3 to 30 carbon atoms; or a substituted or unsubstituted aryl group having 6 to 30 carbon atoms.

13. The heterocyclic compound of claim 9, wherein the compound of Chemical Formula 1-1 is represented by any one of the following compounds:

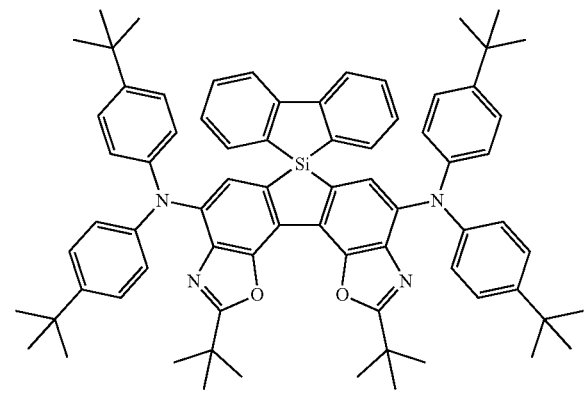

91
-continued
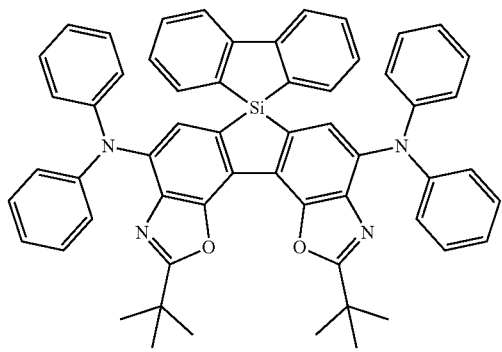
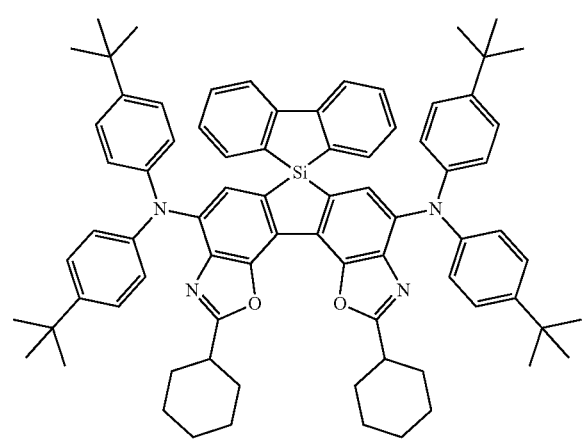
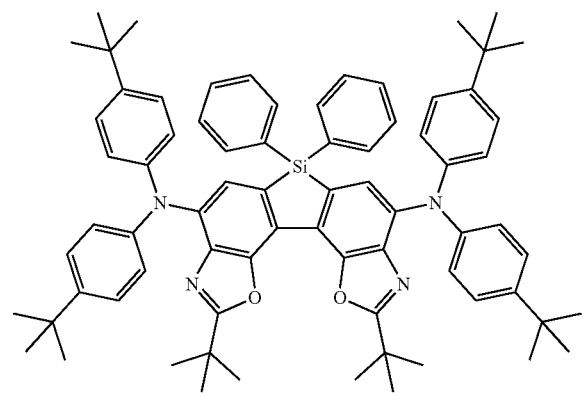
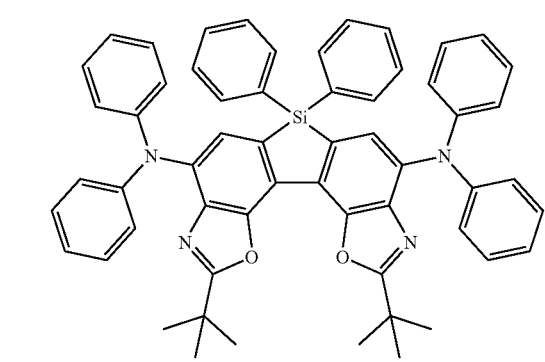
92
-continued
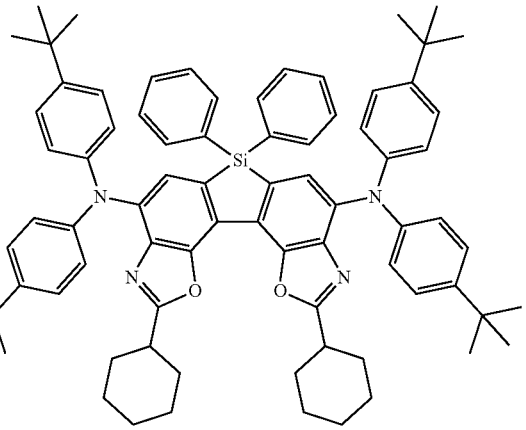
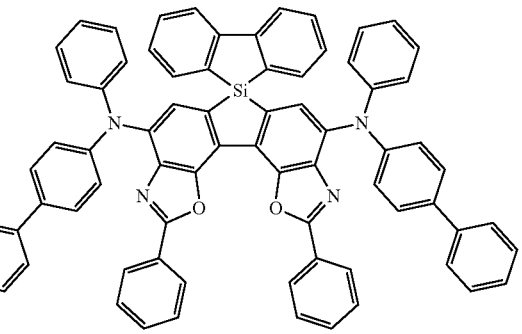
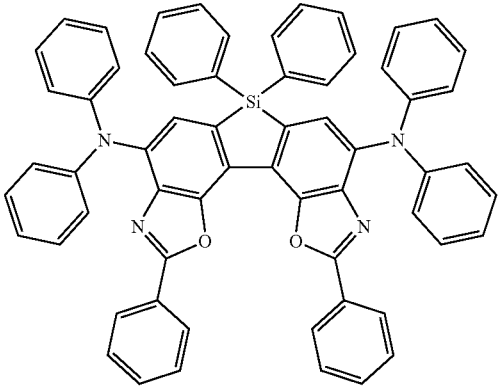

93
-continued
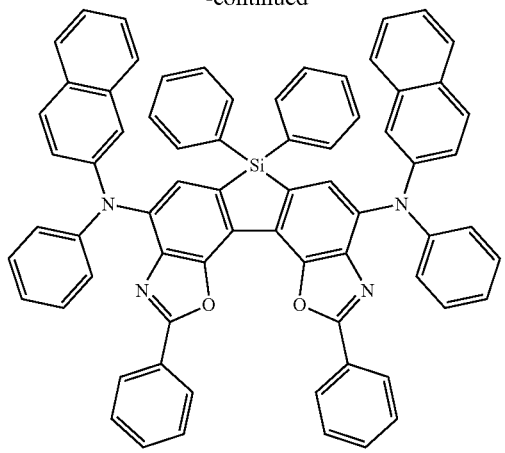
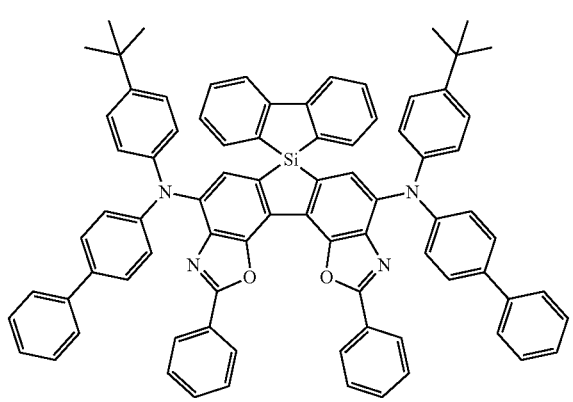
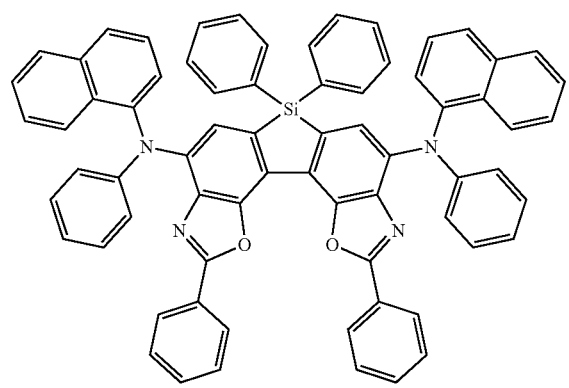
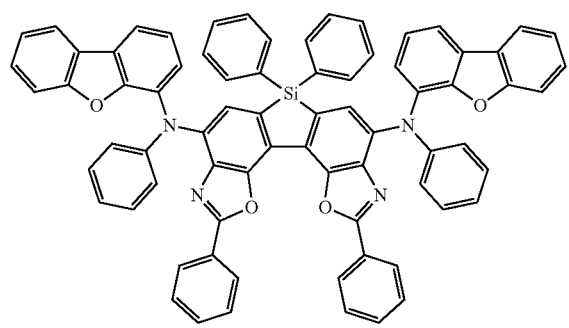
94
-continued
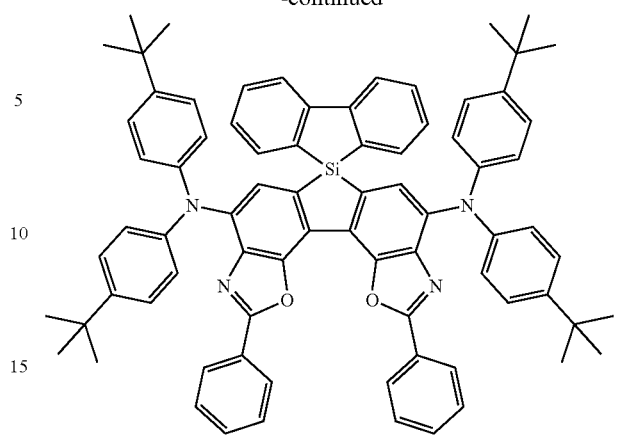
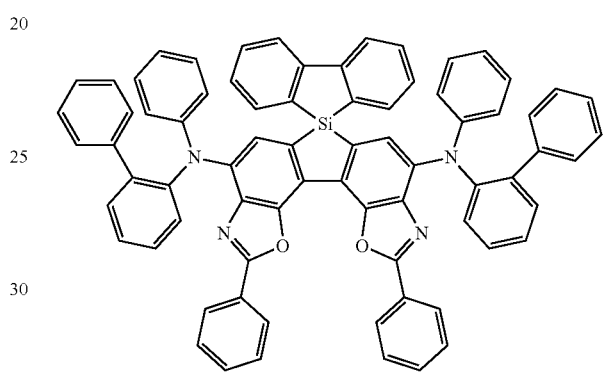
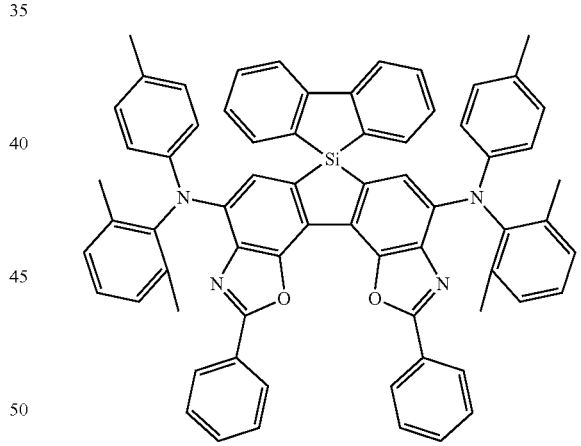
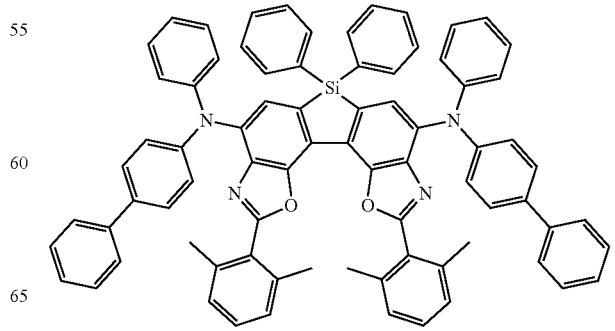

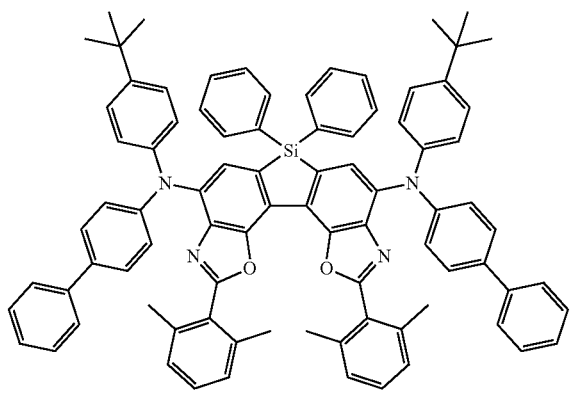

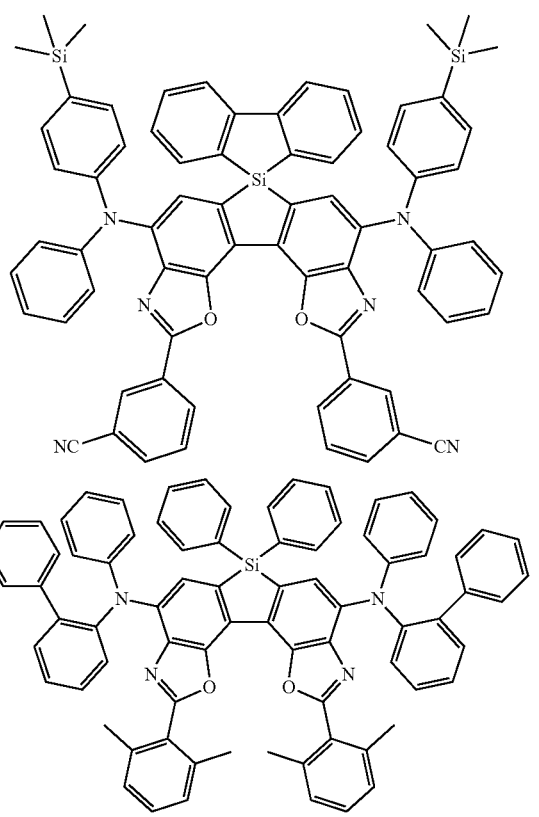

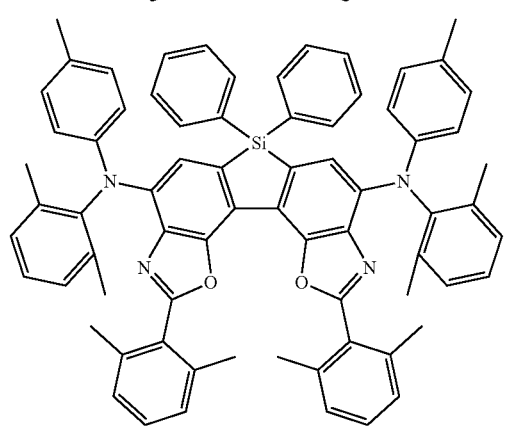

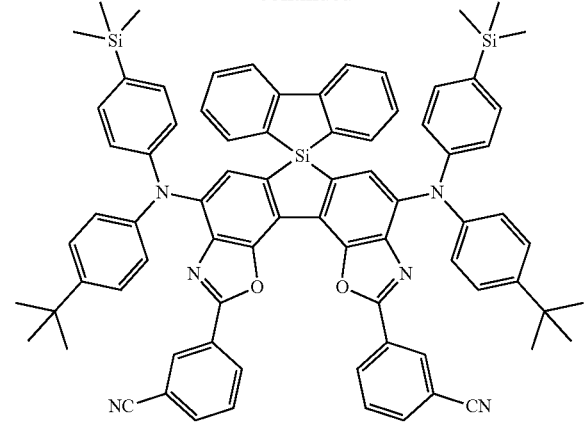

14. An organic light emitting device comprising:
a first electrode;
a second electrode provided to face the first electrode; and
one or more organic material layers provided between the first electrode and the second electrode,
wherein one or more layers of the one or more organic material layers comprise the heterocyclic compound of claim 9.

15. The organic light emitting device of claim 14, wherein the one or more organic material layers comprise a hole injection layer or a hole transfer layer, and the hole injection layer or the hole transfer layer comprises the heterocyclic compound.

16. The organic light emitting device of claim 14, wherein the one or more organic material layers comprise an electron transfer layer or an electron injection layer, and the electron transfer layer or the electron injection layer comprises the heterocyclic compound.

17. The organic light emitting device of claim 14, wherein the one or more organic material layers comprise a light emitting layer, and the light emitting layer comprises the heterocyclic compound.

\* \* \* \* \*